(12) United States Patent
Agoston et al.

(10) Patent No.: US 7,371,741 B2
(45) Date of Patent: May 13, 2008

(54) ESTRADIOL DERIVATIVES AND PHARMACEUTICAL COMPOSITIONS USING SAME

(75) Inventors: Gregory E. Agoston, Germantown, MD (US); Theresa M. LaVallee, Rockville, MD (US); Victor S. Pribluda, Silver Spring, MD (US); Jamshed H. Shah, Brookeville, MD (US); Anthony M. Treston, Rockville, MD (US)

(73) Assignee: EntreMed, Inc., Rockville, MD (US)

( * ) Notice: Subject to any disclaimer, the term of this patent is extended or adjusted under 35 U.S.C. 154(b) by 303 days.

(21) Appl. No.: 10/856,340

(22) Filed: May 28, 2004

(65) Prior Publication Data

US 2005/0014737 A1 Jan. 20, 2005

Related U.S. Application Data

(60) Provisional application No. 60/474,288, filed on May 28, 2003.

(51) Int. Cl.
- A61K 31/56 (2006.01)
- C07J 31/00 (2006.01)
- C07J 13/00 (2006.01)
- C07J 41/00 (2006.01)
- C07J 3/00 (2006.01)

(52) U.S. Cl. .................. 514/169; 514/177; 514/178; 514/182; 552/521; 552/530; 552/531; 552/532; 552/610; 552/611; 552/625; 552/626

(58) Field of Classification Search .............. 514/169, 514/177, 178, 182; 552/500, 521, 530, 531, 552/532, 610, 611, 625, 626

See application file for complete search history.

(56) References Cited

U.S. PATENT DOCUMENTS

| | | |
|---|---|---|
| 2,584,271 A | 2/1952 | Huffman |
| 2,846,453 A | 8/1958 | Hoehn |
| 3,166,577 A | 1/1965 | Ringold et al. |
| 3,410,879 A | 11/1968 | Smith et al. |
| 3,470,218 A | 9/1969 | Farah |
| 3,492,321 A | 1/1970 | Crabbe |
| 3,496,272 A | 2/1970 | Kruger |
| 3,562,260 A | 2/1971 | De Ruggieri et al. |
| 3,956,348 A | 5/1976 | Hilscher |
| 4,172,132 A | 10/1979 | Draper et al. |
| 4,212,864 A | 7/1980 | Tax |
| 4,307,086 A | 12/1981 | Tax |
| 4,444,767 A | 4/1984 | Torelli et al. |
| 4,522,758 A | 6/1985 | Ward et al. |
| 4,552,758 A | 11/1985 | Murphy et al. |
| 4,634,705 A | 1/1987 | DeBernardis et al. |
| 4,743,597 A | 5/1988 | Javitt et al. |
| 4,808,402 A | 2/1989 | Leibovich et al. |
| 4,994,443 A | 2/1991 | Folkman et al. |
| 5,001,116 A | 3/1991 | Folkman et al. |
| 5,135,919 A | 8/1992 | Folkman et al. |
| 5,504,074 A | 4/1996 | D'Amato et al. |
| 5,521,168 A | 5/1996 | Clark |
| 5,621,124 A | 4/1997 | Seilz et al. |
| 5,629,327 A | 5/1997 | D'Amato |
| 5,629,340 A | 5/1997 | Kuwano et al. |
| 5,639,725 A | 6/1997 | O'Reilly et al. |
| 5,643,900 A | 7/1997 | Fotsis et al. |
| 5,646,136 A | 7/1997 | Petrow |
| 5,661,143 A | 8/1997 | D'Amato et al. |
| 5,716,981 A | 2/1998 | Hunter et al. |
| 5,733,876 A | 3/1998 | O'Reilly et al. |
| 5,763,432 A | 6/1998 | Tanabe et al. |
| 5,776,704 A | 7/1998 | O'Reilly et al. |
| 5,792,845 A | 8/1998 | O'Reilly et al. |
| 5,837,682 A | 11/1998 | O'Reilly |
| 5,854,205 A | 12/1998 | O'Reilly et al. |
| 5,854,221 A | 12/1998 | Cao et al. |
| 5,861,372 A | 1/1999 | Folkman et al. |
| 5,885,795 A | 3/1999 | O'Reilly et al. |
| 5,892,069 A | 4/1999 | D'Amato et al. |

(Continued)

FOREIGN PATENT DOCUMENTS

DE 1907330 10/1969

(Continued)

OTHER PUBLICATIONS

Gian Tondury et al., Zur Wirkung Der Sexualhormone Auf Wachstum und Differenzierung (See English Summary p. 55), *Cambridge Philosophical Society*, pp. 28-58, Dec. 17, 1955.

(Continued)

*Primary Examiner*—Barbara P. Badio
(74) *Attorney, Agent, or Firm*—King & Spalding LLP

(57) ABSTRACT

Compositions and methods for treating mammalian disease characterized by undesirable angiogenesis by administering compounds of the general formula:

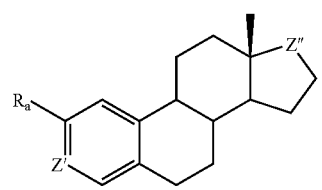

wherein the variables are defined in the specification.

9 Claims, No Drawings

U.S. PATENT DOCUMENTS

| | | | |
|---|---|---|---|
| 5,919,459 A | 7/1999 | Nacy et al. | |
| 5,958,892 A | 9/1999 | Mukhopadhyay et al. | |
| 5,962,445 A | 10/1999 | Stewart | |
| 6,011,023 A | 1/2000 | Clark et al. | |
| 6,011,024 A | 1/2000 | Reed | |
| 6,046,186 A | 4/2000 | Tanabe et al. | |
| 6,051,726 A | 4/2000 | Sachdeva et al. | |
| 6,054,598 A | 4/2000 | Sachdeva et al. | |
| 6,136,992 A | 10/2000 | Ram et al. | |
| 6,200,966 B1 | 3/2001 | Stewart | |
| 6,239,123 B1 | 5/2001 | Green et al. | |
| 6,284,789 B1 | 9/2001 | LaLonde et al. | |
| 6,346,510 B1 | 2/2002 | O'Reilly et al. | |
| 6,358,940 B1 | 3/2002 | Conney | |
| 6,399,773 B1 | 6/2002 | Liu et al. | |
| 6,410,029 B1 | 6/2002 | Mukhopadhyay et al. | |
| 6,413,513 B1 | 7/2002 | Holaday | |
| 6,448,419 B1 | 9/2002 | Paaren et al. | |
| 6,514,971 B1 | 2/2003 | Thomas et al. | |
| 6,528,676 B1 | 3/2003 | D'Amato et al. | |
| 6,593,321 B2 | 7/2003 | Rao et al. | |
| 6,605,622 B2 | 8/2003 | Green et al. | |
| 6,723,858 B2 | 4/2004 | D'Amato et al. | |
| 6,730,665 B1 | 5/2004 | Maran et al. | |
| 6,953,785 B2 | 10/2005 | Ino et al. | |
| 2002/0002294 A1 | 1/2002 | D'Amato et al. | |
| 2002/0035098 A1 | 3/2002 | Slaga et al. | |
| 2002/0068724 A1 | 6/2002 | Slaga et al. | |
| 2002/0082433 A1 | 6/2002 | Agoston et al. | |
| 2002/0119959 A1 | 8/2002 | D'Amato et al. | |
| 2002/0147183 A1 | 10/2002 | Agoston et al. | |
| 2002/0165212 A1 | 11/2002 | D'Amato et al. | |
| 2003/0027803 A1 | 2/2003 | Slaga et al. | |
| 2003/0036539 A1 | 2/2003 | Slaga et al. | |
| 2003/0050294 A1 | 3/2003 | Jackson et al. | |
| 2003/0073674 A1 | 4/2003 | Slaga et al. | |
| 2003/0096799 A1 | 5/2003 | Rao et al. | |
| 2003/0096800 A1 | 5/2003 | D'Amato et al. | |
| 2003/0229061 A1 | 12/2003 | Rao et al. | |
| 2003/0236408 A1 | 12/2003 | D'Amato et al. | |
| 2004/0053906 A1 | 3/2004 | Slaga et al. | |
| 2004/0072813 A1 | 4/2004 | D'Amato et al. | |
| 2004/0082558 A1 | 4/2004 | Tofovic et al. | |
| 2004/0097479 A1 | 5/2004 | Agoston et al. | |
| 2004/0116397 A1 | 6/2004 | Slaga et al. | |
| 2004/0186086 A1 | 9/2004 | Bunschoten et al. | |
| 2004/0186086 A1 | 10/2004 | Bunschoten et al. | |
| 2004/0209855 A1 | 10/2004 | Tofovic et al. | |
| 2005/0070488 A1 | 3/2005 | Bennik et al. | |
| 2005/0148565 A1 | 7/2005 | Cooperwood | |
| 2005/0182038 A1 | 8/2005 | Cooperwood | |
| 2005/0192258 A1 | 9/2005 | Agoston et al. | |
| 2005/0203075 A1 | 9/2005 | Agoston et al. | |
| 2006/0025393 A1 | 2/2006 | Liao et al. | |
| 2006/0079576 A1 | 4/2006 | D'Amato et al. | |
| 2006/0116360 A1 | 6/2006 | Fogler et al. | |
| 2006/0135796 A1 | 6/2006 | Agoston et al. | |
| 2006/0183727 A1 | 8/2006 | D'Amato et al. | |
| 2007/0004689 A1 | 1/2007 | Agoston et al. | |
| 2007/0010505 A1 | 1/2007 | Agoston et al. | |

FOREIGN PATENT DOCUMENTS

| | | |
|---|---|---|
| DE | 2 004 516 | 9/1970 |
| DE | 27 57 157 | 12/1977 |
| DE | 3625315 | 1/1988 |
| EP | 0166937 A2 | 8/1986 |
| EP | 0657175 A2 | 6/1995 |
| GB | 857080 | 12/1960 |
| GB | 857081 | 12/1960 |
| GB | 1570597 | 7/1980 |
| GB | 2252498 A | 8/1992 |
| JP | 39-5480 B | 4/1939 |
| JP | 41 000100 A | 1/1966 |
| JP | 42-928 B | 1/1967 |
| JP | 58-131978 | 8/1983 |
| JP | 62-135472 | 6/1987 |
| JP | 63090763 A | 4/1988 |
| JP | 63-119500 | 5/1988 |
| JP | 04-046120 | 2/1992 |
| JP | 09316000 A | 9/1997 |
| JP | 11-209322 | 8/1999 |
| SU | 1240038 A1 | 10/1996 |
| WO | WO 87/02367 A3 | 4/1987 |
| WO | WO 88/03151 A2 | 5/1988 |
| WO | WO 88/08002 A1 | 10/1988 |
| WO | WO 90/15816 A1 | 12/1990 |
| WO | WO 93/03729 A1 | 3/1993 |
| WO | WO 93/10805 A1 | 6/1993 |
| WO | WO 93/19746 A1 | 10/1993 |
| WO | WO 95/04535 A1 | 2/1995 |
| WO | WO 98/32763 A1 | 7/1998 |
| WO | WO 98/40398 | 9/1998 |
| WO | WO 99/01142 A1 | 1/1999 |
| WO | WO 99/22728 A1 | 5/1999 |
| WO | WO 99/33858 * | 7/1999 |
| WO | WO 99/33858 A3 | 7/1999 |
| WO | WO 99/33859 A2 | 7/1999 |
| WO | WO 99/35150 A3 | 7/1999 |
| WO | WO 99/45018 A1 | 9/1999 |
| WO | WO 00/07576 A2 | 2/2000 |
| WO | WO 00/10552 A2 | 3/2000 |
| WO | WO 00/66095 A2 | 11/2000 |
| WO | WO 00/68246 A1 | 11/2000 |
| WO | WO 01/27132 A1 | 4/2001 |
| WO | WO 01/85755 A1 | 11/2001 |
| WO | WO 02/15910 A1 * | 2/2002 |
| WO | WO 2004/101595 A1 | 11/2004 |

OTHER PUBLICATIONS

Mollendorff, W. Von, Wachstumsstorungen durch Geschlechtshormone, nach Untersuchungen an Gewebekulturen, pp. 187-202, Jun. 12, 1941.

Staples et al., Structural Requirements for Steroid Inhibition of Sheep Lymphocyte Mitogenesis in vitro, *Steroids* vol/Iss: 44 (5), pp. 419-433, Nov. 1984.

U.S. Appl. No. 09/641,327, filed Aug. 18, 2000.

U.S. Appl. No. 09/644,387, filed Aug. 23, 2000.

U.S. Appl. No. 10/635,846, filed Aug. 5, 2003.

U.S. Appl. No. 10/789,471, filed Feb. 27, 2004.

Lilopristone/(1-[4-(Dimethylamino)phenyl]-17-hydroxy-17-(3-hydroxy-1-propenyl) estra-4,9-diene-3-one; AK 98734, *Dictionary of Drugs (1990), Dict. of Steroids (1991), Dict. of Org. Cmpds (6th Ed) (1996), Dict. of Pharm Agents (1997)*, 1990.

(Paragraphs 583-584), *The Merck Index 11th Edition*, p. 88, 1989.

*Research Plus Catalog*, pp. 50-58, 1993.

News Article: Hoffman-La Roche Signs $70 Million Deal with Millenium on Genomics Technology, *Genetic Engineering News*, Apr. 15, 1994.

News Article: Advanced Drug Delivery Systems Peak Interest of Pharmaceutical & Biotech Firms, *Genetic Engineering News*, Apr. 15, 1994.

News Article: Nasal Spray for Treating Bleeding Disorders, *Genetic Engineering News*, Apr. 15, 1994.

2-Methoxystradiol—An Orally Active Endogenous Inhibitor of Angiogenesis, *EntreMed Website Article*, pp. 1-10, Jul. 11, 2000.

Aboulwafa et al., Synthesis and evaluation for uterotrophic and antiimplantation activities of 2-substituted estradiol derivatives, *Steriods*, vol. 57, pp. 199-204, Apr. 1992.

Adams, E.F. et al., Steroidal regulation of oestradiol-17B dehydrogenase activity of the human breast cancer cell line MCF-7 (Chemical Abstracts Doc. No. 109:32325, 1988) (Abstract Only), *Journal of Endocrinology*, vol. 118(1), pp. 149-154, Jul. 1988.

Aizu-Yokota et al., Natural Estrogens Induce Modulation of Microtubules in Chinese Hamster V79 Cells in Culture, *Cancer Research*, vol. 55, pp. 1863-1868, May 1, 1995.

Algire, G.H. et al., Vascular reactions of normal and malignant tumors in vivo. I. Vascular reactions of mice to wounds and to normal and neoplastic transplants, *Journal of the National Cancer Institute* vol. 6, pp. 73-85, Aug. 1945.

Aliev et al., 54929q Synthesis of cycloalkyl derivatives of dihydric phenols and their ethers, *Chemical Abstracts*, vol. 72, p. 370, 1970.

Anstead et al., The Estradiol Pharmacophore: Ligand Structure-Estrogen Receptor Binding Affinity Relationships and a Model for the Receptor Binding Site, *Steroids*, vol. 62, pp. 268-303, 1997.

Arnoldi et al., Sweet Isovanillyl Derivatives: Synthesis and Structure-Taste Relationships of Conformationally Restricted Analogs (Abstract only), *Journal of Agric, Food Chem.*, vol. 46(10), pp. 4002-4010, 1998.

Attalla et al., 2-Methoxyestradiol Arrests Cells in Mitosis without Depolymerizing Tubulin, *Biochemical and Biophysical Research Communications*, vol. 228, pp. 467-473, 1996.

Attalla et al., 2-Methoxyestradiol-Induced Phosphorylation of Bcl-2: Uncoupling from JNK/SAPK Activation (Abstract only), *Biochemical and Biophysical Research Communications*, vol. 247 (3), pp. 616-619, Jun. 29, 1998.

Audier et al., Orientation de la fragmentation en spectrometrie de masse par introduction de groupements fonctionnels. VII.—Etheylenecetals de ceto-2 steroides, *Bulletin De La Societe Chimique De France*, vol. 10, pp. 3088-3090, 1965.

Ayala et al., The Induction of Accelerated Thymic Programmed Cell Death During Polymicrobial Sepsis: Control by Corticosteroids but not Tumor Necrosis Factor (Abstract only), *Shock*, vol. 3 (4), pp. 259-267, Apr. 1995.

Banik et al., Orally Active Long-Acting Estrogen (AY-20,121) (3-(2-propynyloxy)-estra-1,3,5,(10)-triene-17. beta.-ol trimethylacetate) (Identifier only), *Steroids*, vol. 16 (3), pp. 289-296, 1970.

Bardon et al., Steroid Receptor-Mediated Cytotoxicity of an Antiestrogen and an Antiprogestin in Breast Cancer Cells (Abstract only), *Cancer Research*, vol. 47 (5), pp. 1441-1448, Mar. 1, 1987.

Barnes et al., Tumor Necrosis Factor Production in Patients with Leprosy, *Infection and Immunity*, vol. 60 (4), pp. 1441-1446, Apr. 1992.

Bhat et al., Estradiol-induced Mitotic Inhibition in the Bursa of Fabricius of Male Domestic Duckling (Chemical Abstracts Doc. No. 98:31837, 1982), *Mikroskopie*, vol. 39, pp. 113-117, May 1982.

Bindra et al., Studies in Antifertility Agents.8.Seco Steroids. 2. 5,6-Secoestradiol and Some Related Compounds, *Journal of Medicinal Chemistry*, vol. 18 (9), pp. 921-925, 1975.

Blagosklonny et al., Raf-1/bcl-2 Phosphorylation: A Step from Microtubule Damage to Cell Death, *Cancer Research*, vol. 57, pp. 130-135, Jan. 1, 1997.

Blickenstaff et al., Estrogen-Catharanthus (Vinca) Alkaloid Conjugates (Chemical Abstracts Doc. No. 94:114277, 1981), *Cytotoxic Estrogens in Hormone Receptive Tumors*, pp. 89-105, 1980.

Blickenstaff et al., Synthesis of Some Analogs of Estradiol, *Steroids*, vol. 46 (4,5), pp. 889-902, Oct. 1985.

Boyce et al., Some Preliminary Synthetical Studies with 5,6,7,8-Tetra-hydro-8-methylindane-1,5-dione, *Unknown*, pp. 4547-4553, 1960.

Boye et al., 185. Deaminocolchinyl Methyl Ether: Synthesis from 2,3,4,4'-Tetramethoxybiphenyl- 2-carbaldehyde. Comparison of Antitubulin Effects of Deaminocolchinyl Methyl Ether and Dehydro Analogs, *Helvitica Chimica Acta*, vol. 72, pp. 1690-1696, 1989.

Brandi et al., Bone endothelial cells as estrogen targets (Abstract only), *Calcif. Tissue Int.*, vol. 53 (5), pp. 312-317, 1993.

Brem, H. et al., Interstitial chemotherapy with drug polymer implants for the treatment of recurrent gliomas, *Journal of Neurosurgery*, vol. 74, pp. 441-446, Mar. 1, 1991.

Brodie, A.M., Aromatase Inhibitors in the Treatment of Breast Cancer (Abstract only), *Journal of Steroid Biochemistry and Molecular Biology*, vol. 49 (4-6), pp. 281-287, Jun. 1994.

Brosens et al., Comparative Study of the Estrogenic Effect of Ethinylestradiol and Mestranol on the Endometrium, *Laboratory for Gynecological Physiopathology*, vol. 14 (6), pp. 679-685, Dec. 1, 1976.

Brueggemeier et al., 2-Methoxymethylestradiol: a new 2-methoxy estrogen analog that exhibits antiproliferative activity and alters tubulin dynamics, *Journal of Steroid Biochemistry & Molecular Biology*, vol. 78, pp. 145-156, 2001.

Burrows, N.P., Thalidomide Modifies Disease, *British Medical Journal*, vol. 307 (6909), pp. 939-940, Oct. 9, 1993.

Cambie et al., Aromatic Steroids. Part II. Chromium Trioxide Oxidation of Some Oestra-1,3-5(10)-trienes, *Journal of the Chemical Society*, vol. 9, pp. 1234-1240, 1969.

Cambie et al., Aromatic Steroids. Part I. Oxidation Products of 3-Methoxyestra-1,3,5(10)-triene- 17β-yl Acetate, *J. Chem. Soc.*, pp. 2603-2608, 1968.

Castagnetta, L. et al., Simple Approach to Measure Metabolic Pathways of Steroids in Living Cells, *Journal of Chromatography*, vol. 572, pp. 25-39, Dec. 6, 1991.

Chasserot-Golaz et al., Biotransformation of 17.beta.-hydroxy-11.beta.-(4-dimethylaminophenyl) 17.alpha. 1-propynyl-estra-4,9-diene-3-one (RU486) in Rat Hepatoma Variants (Identifier only), *Biochemical Pharmacology*, vol. 46 (11), pp. 2100-2103, 1993.

Chen et al., A New Synthetic Route to 2- and 4-Methoxystradiols by Nucleophilic Substitution, *Steroids*, vol. 47 (1), pp. 63-66, Jan. 1986.

Chen et al., Synthesis of 11.beta.-(4-dimethylaminophenyl)-17.beta-hydroxy-17.alpha.- (1-propynyl) estra-4, 9-dien-3-one (RU486) (Identifier only), *Nanjing Yaoxueyuan Xuebao*, vol. 17 (4), pp. 282-285, 1986.

Cohen et al., Novel Total Synthesis of (+)-Estrone 3-Methyl Ether, (+)-13βEthyl-3-methoxygona-1,3,5(10)-trien-17-one, and (+)-Equilenin 3-Methyl Ether, *The Journal of Organic Chemistry*, vol. 40 (6), pp. 681-685, Mar. 21, 1975.

Collins et al., The Structure and Function of Estrogens. XI. Synthesis of (+/−)-7(8-11α) abeo-Estradiol and its 9,11-Didehydro Derivative, *Aust. Journal of Chemistry*, vol. 45 (1), pp. 71-97, 1992.

Corey et al., Applications of N,N-Dimethylhydrazones to Synthesis. Use in Efficient, Positionally and Stereochemically Selective C-C Bond Formation; Oxidative Hydrolysis to Carbonyl Compounds, *Tetrahedon Letters*, vol. 1, pp. 3-6, 1976.

Corey et al., Facile Conversion of N,N-Dimethylhydrazones to Cabonyl Compounds by Cupric Ion-Catalyzed Hydrolysis, *Tetrahedron Letters*, vol. 41, pp. 3678-3668, 1976.

Crabbe, P., Cotton effect of the styrene chromophore (Abstract only), *Chem. Ind.*, vol. 27, pp. 917-918, 1969.

Crum, R. et al., A New Class of Steroids Inhibits Angiogenesis in the Presence of Heparin or a Heparin Fragment, *Science*, vol. 230, pp. 1375-1378, Dec. 20, 1985.

Cummings et al., Apoptosis, *The American Journal of Surgical Pathology*, vol. 21 (1), pp. 88-101, 1997.

Cushman et al., Synthesis, Antitubulin and Antimitotic Activity, and Cytotoxicity of Analogs of 2-Methoxyestradiol, an Endogenous Mammalian Metabolite of Estradiol that Inhibits Tubulin Polymerization by Binding to the Colchicine Binding Site, *Journal of Medicinal Chemistry*, vol. 38 (12), pp. 2041-2049, Jun. 9, 1995.

Cushman et al., Synthesis of Analogs of 2-Methoxyestradiol with Enhanced Inhibitory Effects on Tubulin Polymerization and Cancer Cell Growth, *Journal of Medicinal Chemistry*, vol. 40 (15), pp. 2323-2334, 1997.

D'Amato et al., 2-Methoxyestradiol, an Endogenous Mammalian Metabolite, Inhibits Tubulin Polymerization by Interacting at the Colchicine Site, *Proceedings of the National Academy of Science USA*, vol. 91, pp. 3964-3968, Apr. 26, 1994.

D'Amato, R.J. et al., Thalidomide is an Inhibitor of Angiogenesis, *Proceedings of the National Academy of Science USA*, vol. 91, pp. 4082-4085, Apr. 1, 1994.

Ding et al., Sex Hormone-Binding Globulin Mediates Prostate Androgen Receptor Action via a Novel Signaling Pathway (Abstract only), *Endocrinology*, vol. 139 (1), pp. 213-218, 1998.

Dubey et al., Methoxyestradiols Mediate the Antimitogenic Effects of Estradiol on Vascular Smooth Muscle Cells via Estrogen Receptor-Independent Mechanisms, *Biochemical and Biophysical Research Communications*, vol. 278, pp. 27-33, 2000.

Durani et al., Seco-Oestradiols and Some Non-Steroidal Oestrogens: Structural Correlates of Oestrogenic Action, *Journal of Steroid Biochemistry*, vol. 11, pp. 67-77, 1979.

Dvir et al., Thin-layer Chromatography of DANSYL-oestrogens, *Journal of Chromatography*, vol. 52, pp. 505-506, Nov. 4, 1970.

Eder et al., Synthesis von Ostradiol (in German—No translation available), *Chem. Ber.*, vol. 109, pp. 2948-2953, 1976.

El-Tombary ., Synthesis, Uterotropic, And Antiuterotrophic Activities for Some Estradiol Derivatives Containing Thiadiazole, Thiazoline, and Thiazolidinone Moieties, *Arch. Pharm. Pharm. Med. Chem.*, vol. 330 (9-10), pp. 295-302, 1997.

Emons et al., Modulation der hypophysaren Sekretion von Luteinisierendem Hormon (LH) durch Ostrogene, *Focus MHL*, vol. 3, pp. 221-228, 1986.

Enjyoji, K. et al., Effect of Heparin on the Inhibition of Factor Xa by Tissue Factor Pathway Inhibitor: A Segment, Gly$^{213}$-Phe$^{243}$, of the third Kunitz Domain is a Heparin-Binding Site, *Biochemistry*, vol. 34 (17), pp. 5725-5735, 1995.

Epe et al., Microtubular Proteins as Cellular Targets for Carcinogenic Estrogens and Other Carcinogens, *Mechanisms of Chromosome Distribution and Aneuploidy*, pp. 345-351, 1989.

Evans et al., A Convergent Total Synthesis of +/− Colchicine and +/− Desacetamidoisocolchicine, *Journal of the American Chemical Society*, vol. 103, pp. 5813-5821, Sep. 23, 1981.

Fanchenko et al., Characteristics of the guinea pig uterus estrogen receptor system (Abstract only), *Byull. Eksp, Biol. Med.*, vol. 85 (4), pp. 467-470, 1978.

Fetizon et al., Synthesis of 2-keto steroids (Abstract only), *Bull. Soc. Chim. FR.*, vol. 8, pp. 3301-3306, 1968.

Fevig et al., A Short, Stereoselective Route to 16α(Substituted-alkyl)estradiol Derivatives, *Journal of Organic Chemistry*, vol. 52, pp. 247-251, 1987.

Field et al., Effect of Thalidomide on the Graft versus Host Reaction, *Nature*, vol. 211 (5055), pp. 1308-1310, Sep. 17, 1966.

Fieser et al., N-Methylformanilide, *Organic Synthesis Collective Vol. 3*, vol. 3, pp. 590-591, 1955.

Fishman, J., Synthesis of 2-Methoxyestrogens, *Journal of the American Chemical Society*, vol. 80, pp. 1213-1216, Mar. 5, 1958.

Fitzgerald, Molecular Features of Colchicine Associated with Antimitotic Activity and Inhibition of Tubulin Polymerization, *Biochemical Pharmacology*, vol. 25 (12), pp. 1383-1387, Jun. 15, 1976.

Flohe et al., Studies on the Hypothetical Relationship of Thalidomide-induced Embryopathy and Collagen Biosynthesis, *Arzneimitte/Forschung (Germany West)*, vol. 31 (2), pp. 315-320, Jan. 1, 1981.

Folkman et al., Angiogenesis Inhibition and Tumor Regression Caused by Heparin or a Heparin Fragment in the Presence of Cortisone, *Science*, vol. 221, pp. 719-725, Aug. 19, 1983.

Folkman, J., Tumor Angiogenesis: Therapeutic Implications, *New England Journal of Medicine*, vol. 285 (21), pp. 1182-1186, Nov. 18, 1971.

Folkman, J. et al., Induction of Angiogenesis During the Transition from Hyperplasia to Neoplasia, *Nature*, vol. 339, pp. 58-61, May 4, 1989.

Folkman, J. et al., Tumor Behavior in Isolated Perfused Organs in vitro Growth and Metastases of Biopsy Material in Rabbit Thyroid and Canine Intestinal Segment, *Annals of Surgery*, vol. 164(3), pp. 491-502, Sep. 1, 1966.

Fotsis et al., The Endogenous Oestrogen Metabolite 2-Methoxyoestradiol Inhibits Angiogenesis and Suppresses Tumour Growth, *Nature*, vol. 368, 237-239, Mar. 17, 1994.

Fraser et al., Angiogenesis and its control in the femal reproductive system (Abstract only), *British Medical Bulletin*, vol. 56 (3), pp. 787-797, 2000.

Gadosy et al., Generation, Characterization, and Deprotonation of Phenol Radical Cations, *Journal of Physical Chemistry*, vol. 103, pp. 8834-8839, 1999.

Gandhi et al., Mannich Reaction of Estrone (Abstract Only), *Journal of Indian Chem. Soc.*, vol. 39, pp. 306-308, 1962.

Gaslini et al., Reaction of Eugenol with Synthesis Gas. Synthesis of 5,6,7,8-Tetrahydro-3-methoxy-2-napthol, *Journal of Organic Chemistry*, vol. 29 (5), pp. 1177-1180, May 1964.

Getahun et al., Synthesis of Alkoxy-Substituted Diaryl Compounds and Correlation of Ring Separation with Inhibition of Tubulin Polymerization: Differential Enhancement of Inhibitory Effects Under Suboptimal Polymerization Reaction Conditions, *Journal of Medicinal Chemistry*, vol. 35 (6), pp. 1058-1067, Mar. 20, 1992.

Gimbrone, M.A. et al., Tumor Growth and Neovascularization: An Experimental Model Using the Rabbit Cornea, *Journal of the National Cancer Institute*, vol. 52(2), pp. 413-427, Feb. 1974.

Gimbrone, M.A. et al., Tumor dormancy in vivo by Prevention of Neovascularization, *Journal of Experimental Medicine*, vol. 136, pp. 261-276, 1972.

Gonzalez et al., Synthesis and Pharmacological Evaluation of 8αEstradiol Derivatives, *Steroids*, vol. 40 (2), pp. 171-187, Sep. 1982.

Gross et al., Inhibition of Tumor Growth, Vascularization, and Collagenolysis in the Rabbit Cornea by Medroxyprogesterone, *Procedings of the National Academy of Science USA*, vol. 78 (2), pp. 1176-1180, Feb. 1981.

Gross, J.L. et al., Modulation of Solid Tumor Growth in vivo by bFGF (Abstract only), *Proceedings of the American Association of Cancer Research*, vol. 31, p. 79, Mar. 1990.

Gujjar et al., The Effect of Estradiol on Candida albicans Growth, *Annals of Clinical and Laboratory Science*, vol. 27 (2), pp. 151-156, 1997.

Gunzler, V., Thalidomide-A Therapy for the Immunological Consequences of HIV Infection?, *Medical Hypothesis*, vol. 30 (2), pp. 105-109, Oct. 1989.

Gupta et al., Antifertility Agents. XIV. Secosteroids. VII. Synthesis of 2α and 2β, 6β-dimethyl- 3β-(p-hydroxyphenyl)-trans-bicyclo[4.3.0]nonan-7-ones and some related compounds (Abstract only), *Indian Journal of Chemistry*, vol. 13 (7), pp. 759-760, 1975.

Gupta et al., Studies in Antifertility Agents. Part XVIII. 2α6β-Diethyl-3β-(p-hydroxyphenyl)-trans-bicyclo[4.3.0]nonan-7β-ol and 6β-methyl-3β-(p-hydroxyphenyl)-2α-propyl- trans-bicyclo[4.3.0]nonan-7β-ol (Abstract only), *Indian Journal of Chemistry*, vol. 19B (10), pp. 886-890, 1980.

Gutierrez-Rodriguez, Treatment of Refractory Rheumatoid Arthritis—The Thalidomide Experience et al., *The Journal of Rheumatology*, vol. 16 (2), pp. 158-163, Feb. 1989.

Gutierrez-Rodriguez, O., Thalidomide—A Promising New Treatment for Rheumatoid Arthritis, *Arthritis and Rheumatism*, vol. 27 (10), pp. 1118-1121, Oct. 1984.

Hahnel et al., The Specificity of the Estrogen Receptor of Human Uterus, *Journal of Steroid Biochemistry*, vol. 4, pp. 21-31, 1973.

Haldar et al., Bc12 is the Guardian of Microtubule Integrity, *Cancer Research*, vol. 57, pp. 229-233, Jan. 15, 1997.

Hamel et al., Interactions of 2-Methoxyestradiol, an Endogenous Mammalian Metabolite, with Unpolymerized Tubulin and with Tubulin Polymers (Abstract only), *Biochemistry*, vol. 35 (4), pp. 1304-1310, 1996.

Han et al., Dehydroepiandrosterone and Dihydrotestosterone Recognition by Human Estrogenic 17β-Hydroxysteroid Dehydrogenase, *Journal of Biological Chemistry*, vol. 275, Iss 2, pp. 1105-1111, Jan. 14, 2000.

Handley et al., Chronic bullons disease of childhood and ulcerative colitis, *British Journal of Dermatology*, vol. 127 (40), pp. 67-68, Jul. 1, 1992.

Hartley-Asp et al., Diethylstilbestrol Induces Metaphase Arrest and Inhibits Microtubule Assembly, *Mutation Research*, vol. 143 (4), pp. 231-235, Aug. 1985.

He et al., A Versatile Synthesis of 2-Methoxyestradiol, an Endogenous Metabolite of Estradiol which Inhibits Tubulin Polymerization by Binding to the Colchicine Biding Site, *Bioorganic & Medicinal Chemistry Letters*, vol. 4 (14), pp. 1724-1728, 1994.

He et al., Novel Cytokine Release Inhibitors. PartII Steroids, *Bioorganic & Medicinal Chemistry Letters*, vol. 8, pp. 2825-2828, 1998.

Hejaz et al., Synthesis and Biological Activity of the Superestrogen (E)-17-Oximino-3-O-sulfamoyl-1,3,5(10)-estratriene: X-ray Crystal Structure of (E)-17-Oximino-3-hydroxy-1,3,5(10)-estratriene, *Journal of Medicinal Chemistry*, vol. 42 (16), pp. 3188-3192, 1999.

Heney et al., Thalidomide treatment for chronic graft-versus-host disease, *British Journal of Haematology*, vol. 78 (1), pp. 23-27, May 1991.

Holker et al., The Reactions of Estrogens with Benzeneseleninic Anhydride and Hexamethyldisilazane, *J. Chem. Soc. Perkin Trans.*, vol. I, pp. 1915-1918, 1982.

Hori, A. et al., Suppression of Solid Tumor Growth by Immunoneutralizing Monoclonal Antibody Against Human Basic Fibroblasts Growth Factor, *Cancer Research*, vol. 51, pp. 6180-6184, Nov. 15, 1991.

Hu, G. Neomycin Inhibits Angiogenin-induced Angiogenesis (abstract Only), *Proceedings of the National Academy of Sciences, USA*, vol. 95 (17), pp. 9791-9795, 1998.

Huang et al., Superoxide Dismutase as a Target for the Selective Killing of Cancer Cells(Abstract only), *Nature*, vol. 407 (6802), pp. 390-395, Sep. 21, 2000.

Huber et al., Tubulin Binding of Conformationally Restricted Bis-Aryl Compounds, *Bioorganic & Medicinal Chemistry Letters*, vol. 1 (5), pp. 243-246, 1991.

Ikegawa et al., Immunoaffinity extraction for liquid chromatographic determination of equilin and its metabolites in plasma (Abstract only), *Biomed. Chromatogr.*, vol. 10 (2), pp. 73-77, 1996.

Imamura et al., Method for Manufacture of Dihydric Phenols (Abstract only), *USPATFULL 76:20259 US 3,950,437*, Apr. 13, 1976.

Ingber, D. et al., Synthetic analogues of fumagillin that inhibit angiogenesis and suppress tumor growth, *Nature*, vol. 348, pp. 555-557, Dec. 6, 1990.

Iriarte et al., Steroids (XCIV). Synthesis of 2-methyl and 1,2-dimethyl estrogens (Abstract only), *Tetrahedron*, vol. 3, pp. 28-36, 1958.

Jaggers et al., Potent Inhibitory Effects of Steroids in an in vitro Model of Angiogenesis (Abstract only), *Journal of Endocrinology*, vol. 150 (3), pp. 457-464, 1996.

Jhingran et al., Studies in Antifertility Agents—Part XLI: Secosteroids-x: Syntheses of Various Stereoisomers of (+−)-2,6β-diethyl-7α-ethynyl-3-(p-hydroxyphenyl)-trans-bicyclo [4.3.0]nonan-7β-ol., *Steroids*, vol. 42 (6), pp. 627-634, 1983.

Josefsson et al., Suppression of Type II Collagen-Induced Arthritis by the Endogenous Estrogen Metabolite 2-Methoxyestradiol, *Arthritis & Rheumatism*, vol. 40 (1), pp. 154-163, Jan. 1997.

Kabarity et al., Further Investigations on the cytological effects of some contraceptives, *Mutation Research*, vol. 135, pp. 181-188, 1984.

Karwat, Separation and Recovery of Hydrogen Sulfide from Hydrocarbon Mixture (Abstract Only), *Caplus DE 1103310*, Sep. 2, 1959.

Kataoka et al., An Agent that Increases Tumor Suppressor Transgene Product Coupled with Systemic Transgene Delivery Inhibits Growth of Metastatic Lung Cancer in Vivo (Abstract only), *Cancer Research*, vol. 58 (21), pp. 4761-4765, Nov. 1998.

Kelly et al., The Stimulation of Prostaglandin Production by Two Antiprogesterone Steroids in Human Endometrial Cells (Abstract only), *Journal of Clinical Endocrinology Metabolism*, vol. 62 (6), pp. 1116-1123, Jun. 1986.

Kim, K.J. et al., Inhibition of Vascular Endothelial Growth Factor-induced Angiogenesis Suppresses Tumor Growth In Vivo, *Nature*, vol. 362, pp. 841-844, Apr. 29, 1993.

Klauber et al., Inhibition of Angiogenesis and Breast Cancer in Mice by the Microtubule Inhibitors 2-Methoxyestradiol and Taxol, *Cancer Research*, vol. 57, pp. 81-86, Jan. 1, 1997.

Knighton, D. et al., Avascular and Vascular Phases of Tumour Growth in the Chick Embyo, *British Journal of Cancer*, vol. 35, pp. 347-356, 1977.

Kole et al., Studies in Antifertility Agents. 11. Secosteroids.5. Synthesis of 9,11-Secoestradiol, *Journal of Medicinal Chemistry*, vol. 18 (7), pp. 765-766, 1975.

Kousteni et al., Reversal of Bone Loss in Mice by Nongenotypic Signaling of Sex Steroids, *Science*, vol. 298, pp. 843-846, Oct. 25, 2002.

Kovacs et al., Steroids. XXIII. Synthesis of 2- 4-hydroxy derivatives of estrone and estradiol (Abstract only), *Acta Phys.Chem.*, vol. 19 (3), pp. 287-290, 1973.

Kurebayashi et al., Paradoxical Hormone Responses KPL-1 Breast Cancer Cells in vivo: a Significant Role of Angiogenesis in Tumor Growth (Abstract only), *Oncology*, vol. 59 (2), pp. 158-165, 2000.

La Vallee et al., 2-Methoxyestradiol Up-Regulates Death Receptor 5 and Induces Apoptosis through Activation of the Extrinsic Pathway, *Cancer Research*, vol. 63, pp. 468-475, Jan. 15, 2003.

Lebras, J. et al., Activation and Regioselective Ortho-Functionalization of the A-Ring of B-Estradiol Promoted by "Cp*Ir": An Efficient Organometallic Procedure for the Synthesis of 2-Methoxyestradiol, *Organometallics* vol. 16, pp. 1765-1771, 1997.

Lewis, Richard J., *Hawley's Condensed Chemical Dictionary*, p. 577, Jan. 1993.

Lewis, Richard, J., *Hawley's Condensed Chemical Dictionary*, pp. 128-129, Jan. 1993.

Li, J., et al., (DN 103:65176) Catechol Formation of Fluoro- and Bromo-substituted Estradiols by Hamster Liver Microsomes. Evidence for Dehalogenation. (Abstract only), *CAPLUS: Molecular Pharmacology*, vol. 27 (5), pp. 559-565, 1985.

Lichtenauer et al., Zur Behandlung des Prostata-Karzinoms, *Deutsches medizinisches Journal*, vol. 23, pp. 248-249, Jan. 1972.

Lien, W. et al., The blood supply of experimental liver metastases. II. A Microcirculatory study of the normal and tumor vessels of the liver with the use of perfused silicone rubber, *Surgery*, vol. 68 (2), pp. 334-340, Aug. 1970.

Limantsev et al., Effect of some estrogen structural analogs on the development of the mouse embyo (Abstract only), *Akush Jinekol.*, vol. 6, pp. 55-56, 1982.

Lin et al., Interactions of Tubulin with Potent Natural and Synthetic Analogs of the Antimitotic Agent Combretastatin: A Structure-Activity Study, *Molecular Pharmacology*, vol. 34 (2), pp. 200-208, Aug. 1988.

Lincoln et al., Conformation of Thiocolchicine and Two B-Ring-Modified Analogues Bound to Tubulin Studied with Optical Spectroscopy, *Biochemistry*, vol. 30 (5), pp. 1179-1187, Feb. 5, 1991.

Lippert et al., The effects of A-ring and D-ring metabolites of estradiol on the proliferation of vascular endothelial cells, *Life Sciences*, vol. 67, pp. 1653-1658, 2000.

Liu et al., Total Synthesis of (+−) -$\Delta^{9(12)}$-Capnellene, *Tetrahedron Letters*, vol. 26 (40), pp. 4847-4850, 1985.

Loozen et al., An approach to the synthesis of 7.beta.-amino estrogens (Abstract only), *Recl.: J.R. Neth.Chem. Soc.*, vol. 102 (10), pp. 433-437, 1983.

Lottering et al., Effects of the 17β-Estradiol Metabolites on Cell Cycle Events in MCF-7 Cells (Chemical Abstracts Doc. No. 117:245769, 1992), *Cancer Research*, vol. 52, pp. 5926-5932, Nov. 1, 1992.

Lottering et al., 17β-Estradiol Metabolites Affect Some Regulators of the MCF-7 Cell Cycle, *Cancer Letters*, vol. 110, pp. 181-186, 1996.

Lovely et al., 2-(Hydroxyalkyl)estradiols: Synthesis and Biological Evaluation, *Journal of Medicinal Chemistry*, vol. 39, pp. 1917-1923, 1996.

Luo et al., Effect of Components of Crowth Ether Copper(I)Iodide Mixed Catalyst on Nucleophilic Substitution of Bromoestrogen (Abstract No. 195225), *Chemical Abstracts*, vol. 111 (21), pp. 818, col. 1, Nov. 20, 1989.

MacCarthy-Morrogh et al., Differential Effects of Estrone and Estrone-3⊖-Sulfamate Derivatives on Mitotic Arrest, Apoptosis, and Microtubule Assembly in Human Breast Cancer Cells, *Cancer Research*, vol. 60, pp. 5441-5450, Oct. 1, 2000.

Maro et al., Mechanism of Polar Body Formation in the Mouse Oocyte: An Interaction Between the Chromosomes, the Cytoskeleton and the Plasma Membrane, *Journal of Embryology and Experimental Morphology*, vol. 92, pp. 11-32, 1986.

Mayol et al., Ethynylestradiol-Induced Cell Proliferation in Rat Liver Involvement of Specific Populations of Hepatocytes (Abstract only), *Carcinogenesis*, vol. 13 (12), pp. 2381-2388, 1992.

Meikrantz et al., Apoptosis and the Cell Cycle, *Journal of Cellular Biochemistry*, vol. 58 (2), pp. 160-174, Jun. 1995.

Meza et al., Managing the Gastrointestinal Complications of AIDS, *Drug Therapy*, vol. 23 (11), pp. 74-83, Nov. 1993.

Michel et al., Inhibition of synaptosomal high-affinity uptake of dopamine and serotonin by estrogen agonists and antagonists (Abstract only), *Biochem. Pharmacol.*, vol. 36 (19), pp. 3175-3180, 1987.

Miller et al., Synthesis and Structure-Activity Profiles of A-Homoestranes, the Estratropones, *Journal of Medicinal Chemistry*, vol. 40, pp. 3836-3841, 1997.

Miller, Thomas, Tubulin as a Therapeutic Target (Abstract only), *Dissertations Abstracts International*, vol. 5907B, pp. 3454, 1998.

Morgan et al., Calcium and Oestrogen Interactions upon the Rat Thymic Lymphocyte Plasma Membrane (Chemical Abstracts Doc. No. 85:172052, 1976), *Biochemical and Biophysical Research Communications*, vol. 72 (2), pp. 663-672, Sep. 20, 1976.

Morisaki et al., Steroids. L1. Aromatization reaction of the cross-conjugated dienone systems by Zinc 9. (Abstract only), *Chem. Pharm. Bull.*, vol. 14 (8), pp. 866-872, 1966.

Mueck et al., Angiogenetic and anti-angiogenetic effects of estradiol and its metabolites (Abstract only), *Journal of Clinical and Basic Cardiology*, vol. 4 (2), pp. 153-155, 2001.

Mukhopadhyay et al., Induction of Apoptosis in Human Lung Cancer Cells after Wild-Type p53 Activation by Methoxyestradiol, *Oncogene*, vol. 14, pp. 379-384, 1997.

Mukundan et al., Liver Regeneration in Oral Contraceptive Treated Female Rats—Effects of Moderate Malnutrition (Chemical Abstracts Doc. No. 102:143342, 1984), *Hormone and Metabolic Research*, vol. 16(12), pp. 641-645, Dec. 1984.

Naafs et al., Thalidomide Therapy An Open Trial, *International Journal of Dermatology*, vol. 24 (2), pp. 131-134, Mar. 1985.

Nakagawa-Yagi et al., The Endogenous Estrogen Matabolite 2-Methoxyestradiol Induces Apoptotic Neuronal Cell DeathIn Vitro, *Life Sciences*, vol. 58 (17), pp. 1461-1467, 1996.

Nakamura et al., Studies on the Total Synthesis of dHColchiceine. I. Synthesis of 3-Hydroxy-9, 10, 11-trimethoxy-1,2,3,4,6,7-hexahydro-5H-dibenzo[a,c] cycloheptatrien-5-one, *Chemical and Pharmaceutical Bulletin*, vol. 10, pp. 281-290, 1962.

Nambara et al., Studies on Steroid Conjugates. III. New Synthesis of 2-Methoxyestrogens, *Chem. Pharm. Bulletin*, vol. 18 (3), pp. 474-480, Mar. 1970.

Nambara et al., Microbial transformation products derived from steriods. I. Synthesis of 1,2- and 3-dimethoxy-4-methylestratrienes (Abstract only), *Chem. Pharm. Bull.*, vol. 20 (2), pp. 336-342, 1972.

Nambara et al., Synthesis of 16β-Oxygenated Catechol Estrogen Methyl Ethers, New and Potential Metabolites, *Chemical & Pharmaceutical Bulletin*, vol. 23 (7), pp. 1613-1616, Jul. 1975.

Nambara, T., et al., DN 82:43650; Analytical Chemical Studies on Steroids. LXIII. Synthesis of Epimeric 2-Hydroxy-16-Chlorestrong Monomethyl Ethers (Abstract only), *HCAPLUS-Chemical and Pharmaceutical Bulletin*, vol. 22 (10), pp. 2455-2457, 1974.

Napolitano et al., 11 Beta-Substituted Estradiol Derivatives. 2. Potential Carbon-11 and Iodine-Labeled Probes for the Estrogen Receptor (Abstract only), *Journal of Medicinal Chemistry*, vol. 38 (14), pp. 2774-2779, Jul. 7, 1995.

Newkome et al., Synthesis of Simple Hydrazones of Carbonyl Compounds by an Exchange Reaction, *Journal of Organic Chemistry*, vol. 31, pp. 677-681, Mar. 1966.

Nguyen, M. et al., Elevated Levels of the Angiogenic Peptide Basic Fibroblast Growth Factor in Urine of Bladder Cancer Patients, *Journal of the National Cancer Institute*, vol. 85 (3), pp. 241-242, Feb. 3, 1993.

Nishigaki et al., Anti-Proliferative Effect of 2-Methoxyestradiol on Cultured Smooth Muscle Cells from Rabbit Aorta, *Atherosclerosis*, vol. 113, pp. 167-170, 1995.

Numazawa et al., Efficient Synthesis of 2-Methoxy- and 4-Methoxy-Estrogens, *Journal of the Chemical Society*, pp. 533-534, Jan. 1, 1983.

Numazawa et al., Novel and Regiospecific Synthesis of 2-Amino Estrogens via Zincke Nitration, *Steroids*, vol. 41 (5), pp. 675-682, 1983.

OCHS et al., Effect of Tumor Promoting Contraceptive Steroids on Growth and Drug Metabolizing Enzymes in Rat Liver (Abstract only), *Cancer Research*, vol. 46 (3), pp. 1224-1232, 1986.

Omar et al., Synthesis, binding affinities and uterotrophic activity of some 2-substituted estradiol and ring-A-fused pyrone derivatives, *European Journal of Medicinal Chemistry*, vol. 29, pp. 25-32, 1994.

Oppolzer et al., 177. The Enantioselective Synthesis of (+)-Estradiol from 1,3-Dihydrobenzo[c] thiophene-2,2-dioxide by Successive Thermal $SO_2$-Extrusion and Cycloaddition Reactions, *Helvetica Chimica Acta*, vol. 63, pp. 1703-1705, 1980.

Pakala et al., Modulation of Endothelial Cell Proliferation by Retinoid x Receptor Agonists, *European Journal of Pharmacology*, vol. 385 (2/3), pp. 255-261, Sep. 1999.

Parthasarathy et al., Antioxidant: A New Role for RU-486 and Related Compounds (Abstract only), *Journal of Clinical Investigation*, vol. 94 (5), pp. 1990-1995, Nov. 1994.

Paull et al., Identification of Novel Antimitotic Agents Acting at the Tubulin Level by Computer-assisted Evaluation of Differential Cytotoxicity Data, *Cancer Research*, vol. 52 (14), pp. 3892-3900, Jul. 15, 1992.

Peng et al., Synthesis and Optical Properties of Novel Unsymmetrical Conjugated Dendrimers, *Journal of the American Chemical Society*, vol. 122, pp. 6619-6623, 2000.

Pert et al., Preparations of 2,4-disubstituted estradiols (Abstract only), *Australian Journal of Chemistry*, vol. 42 (3), pp. 421-432, 1989.

Peters et al., 17-Desoxy Estrogen Analogues, *Journal of Medicinal Chemistry*, vol. 32 (7), pp. 1642-1652, 1989.

Pfeiffer et al., Arc catechol estrogens obligatory mediators of estrogen action in the central nervous system? I. Characterization of pharmacological probes with different receptor binding affinities and catechol estrogen formation rates (Abstract only), *Journal of Endocrinology*, vol. 110 (3), pp. 489-497, 1986.

Plum et al., Vaccination with Peptide to the Heparin Binding Domain of bFGF Conjugated to Liposomes Inhibits bFGF Induced Neovascularization (Abstract only), *Proceedings of the American Association for Cancer Research Annual.*, vol. 39, pp. 8, Mar. 1998.

Plum et al., Administration of a Liposomal FGF-2 Peptide Vaccine Leads to Abrogation of FGF-2-Mediated Angiogenesis and Tumor Development, *Vaccine*, vol. 19 (9-10), pp. 1294-1303, 2000.

Poli et al., Tumor Necrosis Factorα Functions in an Autocrine Manner in the Induction of Human Immunodeficiency Virus Expression, *Proceedings of the National Academy of Science USA*, vol. 87 (2), pp. 782-785, Jan. 1990.

Powell et al., Investigation and Treatment of Orogenital Ulceration; studies on a Possible Mode of Action of Thalidomide, *British Journal of Dermatology*, vol. 113 Supp. 28, pp. 141-144, Jul. 1985.

Pribluda et al., 2-Methoxyestradiol—A Novel Endotenous Chemotherapeutic and Antiangiogenic Agent-Chapter 21, *The New Angiotherapy*, pp. 1-21, Nov. 2000.

Rao et al., Structural Specificity of Estrogens in the Induction of Mitotic Chromatid Non-Disjunction in Hela Cells, *Experimental Cell Research*, vol. 48, pp. 71-81, 1967.

Rao et al., A Novel, Two-Step Synthesis of 2-Methoxyestradiol, *Synthesis*, pp. 168-169, Mar. 1, 1977.

Ravindra, R., Effect of Estradiol on the in vitro Assembly of Rat Brain Tubulin, *Journal of Indian Institute of Science*, vol. 64 (3), pp. 27-35, Mar. 1983.

Romanelli et al., Ethyl-p-Dimethylaminophenylacetate, *Organic Synthesis*, vol. 5, p. 552, Oct. 24, 1973.

Sakakibara et al., Effects of Diethylstilbestrol and its Methl Ethers on Aneuploidy Induction and Microtubule Distribution in Chinese Hamster V79 cells, *Mutation Research*, vol. 263 (4), pp. 269-276, Aug. 1991.

Sakakibara, Kyoichi, 2-Hydroxy-1,3,5(10)-estratriene derivatives (Abstract only) (Identifier: XP-002186126), *Chemical Abstracts*, vol. 60(1), Jan. 6, 1964.

Sato et al., Effect of Estradiol and Ethynylestradiol on Microtubule Distribution in Chinese Hamster V79 Cells, *Chemical and Pharmaceutical Bulletin*, vol. 40 (1), pp. 182-184, Jan. 1992.

Sato et al., Disruptive Effect of Diethylstilbestrol on Microtubules, *Gann*, vol. 75 (12), pp. 1046-1048, Dec. 1984.

Sato et al., Natural estrogens induce modulation of microtubules in Chinese hamster V79 cells in culture (Abstract only), *Horm. Carcinog. II. Proceedings Int. Symp., 2nd (1996), Meeting Date 1994*, pp. 454-457, 1996.

Sawada et al., Colchicine-Like Effect of Diethylstilbestrol (DES) on Mammalian Cells in Vitro, *Mutation Research*, vol. 57, pp. 175-182, May 1978.

Schumacher et al., The Physiological Estrogen Metabolite 2-Methoxyestradiol Reduces Tumor Growth and Induces Apoptosis in Human Solid Tumors, *Cancer Research Clinical Oncology*, vol. 127, pp. 405-410, 2001.

Seaver, Sally, Monoclonal Antibodies in Industry: More Difficult than Orginally Thought, *Genetic Engineering News*, vol. 14, pp. 10 and 21, Aug. 1994.

Seegers et al., Cyclic-AMP and Cyclic-GMP Production in MCF-7 Cells Exposed to Estradiol-17 Beta, Catecholestrogens and Methoxy-Estrogens in MCF-7 Cells (Meeting Abstract only), *Joint MCI-1st Symposium. Third 1st International Symposium. Biology and Therapy of Breast Cancer*, Sep. 25, 1989.

Seegers et al., The Mammalian Metabolite, 2-methoxyestradiol, Affects P53 Levels and Apoptosis Induction in Transformed Cells but Not in Normal Cells (Abstract only), *Journal of Steroid Biochemistry and Molecular Biology*, vol. 62 (4), pp. 253-267, Jul. 1997.

Seegers, J.C. et al., The Cytotoxic Effects of Estradiol-17β Catecholestradiols and Methoxyestradiols on Dividing MCF-7 and HeLa Cells, *Journal of Steroid Biochemistry*, vol. 32 (6), pp. 797-809, Jun. 1989.

Shah et al., (+/−)-(N-alkylamino)benzazepine Analogs: Novel Dopamine D1 Receptor Antagonists (Abstract only), *Journal of Medicinal Chemistry*, vol. 38 (21), pp. 4284-4293, Oct. 13, 1995.

Sharp et al., Diethylstilboestrol: the Binding and Effects of Diethylstilboestrol upon the Polymerisation and Depolymerisation of Purified Microtubule Protein in vitro, *Carcinogenesis*, vol. 6 (6), pp. 865-871, Jun. 1985.

Shim et al., Hydrazinocurcumin, A Novel Synthetic Curcumin Derivative, Is a Potent Inhibitor of Endothelial Cell Proliferation (Abstract only), *Caplus: Bioorganic & Medicinal Chemistry*, vol. 10 (8), pp. 2439-2444, 2002.

Shishkina et al., Synthesis and properties of condensed heterocyclic derivatives of estra-4, 9-dien-17.beta.-ol-3-one (Abstract only), *Khim,-Farm. Zh.*, vol. 8 (1), pp. 7-11, 1974.

Sidky et al., Inhibition of Angiogenesis by Interferons: Effects on Tumor- and Lymphocyte-induced Vascular Responses, *Cancer Research*, vol. 47, pp. 5155-5161, Oct. 1, 1987.

Singh et al., Inhibition of deoxyglucose uptake in MCF-7 breast cancer cells by 2-methoxyestrone and 2-methoxyestrone-3O-sulfamate (Abstract only), *Molecular and Cellular Endocrinology*, vol. 160 (1-2), pp. 61-66, 2000.

Siracusa et al., The Effect of Microtubule- and Microfilament-disrupting Drugs α Preimplantation Mouse Embryos (abstract Only), *Jouranl of Embryology and Experimental Morphology*, vol. 60, pp. 71-82, Dec. 1980.

Soker et al., Neuropilin-1 is Expressed by Endothelial and Tumor Cells as an Isoform-Specific Receptor for Vascular Endothelial Growth Factor, *Cell*, vol. 92, pp. 735-745, Mar. 20, 1998.

Spicer et al., Catecholestrogens Inhibit Proliferation and DNA Synthesis of Porcine Granulosa Cells in Vitro: Comparisoon with Estradiol, 5α-dihydrotestosterone, Gonadotropins and Catecholamines (Chemical Abstracts Doc. No. 111:50609, 1989), *Molecular and Cellular Endocrinology*, vol. 64, pp. 119-126, 1989.

Spyriounis et al., Copper (II) complex of an estradiol derivative with potent antiinflammatory properties (Abstract only), *Arch. Pharm.*, vol. 324 (9), pp. 533-536, 1991.

Srivastava, A. et al., The Prognostic Significance of Tumor Vascularity in Intermediate-Thickness (0.76-4.0 mm Thick) Skin Melanoma, *American Journal of Pathology*, vol. 133 (2), pp. 419-424, Nov. 1988.

Starkov et al., Mono- and Dialkylation of Guaiacol by Olefins on KU-2 Cation Exchanger (Abstract only), *Zhumal Prikladnoi Khimii*, vol. 41 (3), pp. 688-690, 1968.

Sternlicht et al., Colchicine Inhibition of Microtubule Assembly via Copolymer Formation, *The Journal of Biological Chemistry*, vol. 254 (20), pp. 10540-10550, Oct. 25, 1979.

Sun et al., Antitumor Agents. 139. Synthesis and Biological Evaluation of Thiocolchicine Analogs 5,6-Dihydro -6(*S*)-(acyloxy)-and 5,6-Dihydro-6(*S*)-[(aroyloxy) methyl}-1,2,3- trimethoxy-9-(methylthio)-8*H*-cycloheptalnaphthalen-8-ones as Novel Cytotoxic and Antimitotic Agents, *Journal of Medicinal Chemistry*, vol. 36 (5), pp. 544-551, Mar. 5, 1993.

Sunagawa et al., Synthesis of Colchicine; Synthesis of *d*-Demethyoxydeoxy-hexahydrocolchicine, *Chemical & Pharmaceutical Bulletin*, vol. 9, pp. 81-83, 1961.

Taylor, S. et al., Protamine is an Inhibitor of Angiogenesis, *Nature*, vol. 297, pp. 307-312, May 27, 1982.

Teranishi, M. et al., Methylation of Catechol Estrogen with Diazomethane, *Chemical and Pharmaceutical Bulletin*, vol. 31 (9), pp. 3309-3314, Sep. 1983.

Tishler et al., Microtubule-Active Drugs Taxol, Vinblastine, and Nocodazole Increase the Levels of Transcriptionally Active p53, *Cancer Research*, vol. 55, pp. 6021-6025, Dec. 15, 1995.

Tremblay et al., A Convenient Synthetic Method for Alpha-Alkylation of Steroidal 17-Ketone: Preparation of 16β-(THPO-Heptyl)-Estradiol, *Synthetic Communications*, vol. 25 (16), pp. 2483-2495, 1995.

Tremblay et al., Synthesis of 16-(Bromoalkyl)-Estradiols Having Inhibitory Effect on Human Placental Estradiol 17β-Hydroxysteroid Dehydrogenase (17β-HSD Type 1), *Bioorganic & Medicinal Chemistry*, vol. 3 (5), pp. 505-523, 1995.

Tsutsui et al., Comparison of Human Versus Syrian Hamster Cells in Culture for Induction of Mitotic Inhibition, Binucleation and Multinucleation, Following Treatment with Four Aneuploidogens, *Toxicology in Vitro*, vol. 4 (1), pp. 75-84, 1990.

Utne et al., The Synthesis of 2- and 4-Fluoroestradiol, *Journal of Organic Chemistry*, vol. 33 (6), pp. 2469-2473, Jun. 1968.

Van Geerestein et al., Structure of 11.beta.-(4-(dimethylamino)phenyl)-17.beta.-hydroxy-17. alpha.-(2-propenyl) estra-4,9-dien-3-one (Identifier only), *Acta Crystallogr., Sect. C: Cryst, Struct. Commun.*, vol. C43 (2), pp. 319-322, 1987.

Van Tamelen et al., The Synthesis of Colchicine, *Tetrahedon*, vol. 14 (1/2), pp. 8-34, Sep. 1961.

Vicente et al., In Vitro Activity of Thalidomide Against Mycobacterium avium Complex, *Archives of Internal Medicine*, vol. 153 (4), p. 534, Feb. 22, 1993.

Wang et al., Photoaffinity Labeling of Human Placental Estradiol 17.beta.-dehydrogenase with 2-And 4-azidoestrone, 2- and 4-azidoestradiol (abstract Only), *Shengwu Huaxue Zazhi*, vol. 8 (6), pp. 715-718, 1992.

Wang et al., *Synthesis of B-Ring Homologated Estradiol Analogues that Modulate Tubuline Polymerization and Microtubule Stability*, *Journal of Medicinal Chemistry*, vol. 43, pp. 2419-2429, 2000.

Wang, Z. et al., An Optimized Synthesis of 2-Methoxyestradiol, a Naturally Occurring Human Metabolite with Anticancer Activity, *Synth.Commun.*, vol. 28 (23), pp. 4431-4437, 1998.

Weidner, N. et al., Tumor angiogenesis: A New Significant and Independent Prognostic Indicator in Early-Stage Breat Carcinoma, *Journal of the National Cancer Institute*, vol. 84, pp. 1875-1887, Dec. 16, 1992.

Weidner, N. et al., Tumor Angiogenesis Correlates with Metastasis in Invasive Prostate Carcinoma, *American Journal of Pathology*, vol. 143 (2), pp. 401-409, Aug. 1993.

Weidner, N. et al., Tumor Angiogenesis and Metastasis-Correlation in Invasive Breast Carcinoma, *New England Journal of Medicine*, vol. 324 (1), pp. 1-8, Jan. 3, 1991.

Welsch et al., Staphylostatic Activity of Some New Diphenols, Napthols, and Chalcones (Abstract only), *Experientia*, vol. 11, pp. 350-351, 1955.

Wheeler et al., Mitotic Inhibition and Aneuploidy Induction by Naturally Occurring and Synthetic Estrogens in Chinese Hamster Cells in Vitro, *Mutation Research*, vol. 171, pp. 31-41, Jul. 1986.

Wheeler et al., Mitotic Inhibition and Chromosome Displacement Induced by Estradiol in Chinese Hamster Cells (Chemical Abstracts Doc. No. 105:54822, 1986), *Cell Motility and the Cytoskeleton*, vol. 7 (3), pp. 235-247, 1987.

White et al., Treatment of Pulmonary Hemangiomatosis with Recombinant Interferon Alfa-2a, *The New England Journal of Medicine*, vol. 32 (18), pp. 1197-1200, May 4, 1989.

Wiese et al., Induction of the Estrogen Specific Mitogenic Response of MCF-7 Cells by Selected Analogues of Estradiol-17 β.A 3D QSAR Study, *Journal of Medicinal Chemistry*, vol. 40, pp. 3659-3669, 1997.

Wurtz et al., Three-Dimensional Models of Estrogen Receptor Ligand Binding Domain Complexes Based on Related Crystal Structures and Mutational and Structure-Activity Relationship Data, *Journal of Medicinal Chemistry*, vol. 41, pp. 1803-1814, 1998.

Yasuda et al., Accelerated differentiation in seminiferous tubules of fetal mice prenatally exposed to ethinyl estradiol (Abstract only), *Anat. Embryol. (Berl.)*, vol. 174 (3), pp. 289-299, 1986.

Yue et al., 2-Methoxyestradiol, and Endogenous Estrogen Metabolite, Induces Apoptosis in Endothelial Cells and Inhibits Angiogenesis: Possible Role for Stress-Activated Protein Kinase Signaling Pathway and Fas Expression, *Molecular Pharmacology*, vol. 51, pp. 951-952, 1997.

Zoubine et al., 2-Methoxyestradiol-Induced Growth Suppression and Lethality in Estrogen-Responsive MCF-7 Cells May Be Mediated by Down Regulation of p34cdc2 and Cyclin B1 Expression (Abstract only), *International Journal of Oncology*, vol. 15 (4), pp. 639-646, Oct. 1999.

Peripheral Ulcerative Keratitis (Marginal Keratolysis; Peripheral Rheumatoid Ulceration) (Abstract only-Applicants do not have complete copy), *Merck Manual of Diagnosis and Therapy*, Sec. 8, Chapter 8 & 96, Jan. 1, 1995.

Aguayo et al., Angiogenesis in Acute and Chronic Leukemias and Myelodysplastic Syndrome, *Blood*, vol. 96 (6), pp. 2240-2245, Sep. 15, 2000.

Akova et al., Optic Disk Neovascularization in a Patient with Cytomegalovirus Retinitis Associated with Renal Transplantation (Abstract only-Applicants do not have complete copy), Abstract Only, *Oncular Immunology and Inflammation*, vol. 8 (1), pp. 63-65, Mar. 1, 2000.

Amorino et al., Enhancement of Radiation Effects In Vitro by the Estrogen Metabolite 2-Methoxyestradiol, *Radiation Research*, vol. 153, pp. 384-391, Jan. 1, 2000.

Anderson et al., Mutliple Myeloma: New Insights and Therapeutic Approaches (Abstract only-Applicants do not have complete copy), Abstract Only, *Hematology*, pp. 147-165, Jan. 1, 2000.

Armstrong et al., Detection of Vascular Endothelial Growth Factor and Tumor Necrosis Factor Alpha in Epiretinal Membranes of Proliferative Diabetic Retinopathy, Proliferative Vitroretinopathy and Macular Pucker (Abstract only-Applicants do not have complete copy), *Ophthalmologica*, vol. 212 (6), pp. 410-414, Nov. 1998.

Azuma, H., Genetic and Molecular Pathogenesis of Hereditary Hemorrhagic Telangiectasia, Abstract Only, *Journal of Medical Investigation*, vol. 47 (3-4), pp. 81-90, Aug. 1, 2000.

Bacharach et al., In vivo Patterns of Expression of Urokinase and Its Inhibitor PAI-I Suggest a Concerted Role in Regulating Physiological Angiogenesis, *Proceedings of the National Academy of Science USA*, vol. 89 (22), pp. 10686-10690, Nov. 15, 1992.

Baer et al., Corneal Laser Photocoagulation for Treatment of Neovascularization. Efficacy of 577 nm Yellow Dye Laser (Abstract only-Applicants do not have complete copy), Abstract Only, *Ophthalmology*, vol. 99 (2), pp. 173-179, Feb. 1, 1992.

Banerjee et al., 2-Methoxyestradiol Blocks Estrogen-Induced Rat Pituitary Tumor Growth and Tumor Angiogenesis: Possible Role of Vascular Endothelial Growth Factor, *Anticancer Research*, vol. 20, pp. 2641-2646, Jan. 1, 2000.

Barczyk et al., Mast Cells in the Gastrointestinal Tract (Abstract only-Applicants do not have complete copy), Abstract Only, *Roczniki Akademii Medycznej W Bialymstoku (Bialystok)*, vol. 40 (1), pp. 36-57, Jan. 1, 1995.

Bhooma et al., Eales' Disease: Accumulation of Reactive Oxygen Intermediates and Lipid Peroxides and Decrease of Antioxidants Causing Inflammation, Neovascularization and Retinal Damage (Abstract only-Applicants do not have complete copy), Abstract Only, *Current Eye Research*, vol. 16 (2), pp. 91-95, Feb. 1, 1997.

Bissell et al., Putting Tumours in Context, *Nature Reviews Cancer*, vol. 1 (1), pp. 46-54, Oct. 1, 2001.

Boehme et al., Juxtapapillary Choroidal Neovascular Membrane in a Patient with Paget's Disease and Lattice Corneal Dystrophy (Abstract only-Applicants do not have complete copy), Abstract Only, *Journal of the American Optometric Association*, vol. 60 (8), pp. 612-616, Aug. 1, 1989.

Campochiaro et al., Retinal and Choroidal Neovascularization, *Journal of Cellular Physiology*, vol. 184, pp. 301-310, Jan. 1, 2000.

Chang et al., Corneal Neovascularization, *Current Opinions in Optholmology*, vol. 12, pp. 242-249, Jan. 1, 2001.

Cleveland et al., A Radical Approach to Treatment, *Nature*, vol. 407, pp. 309-311, Sep. 21, 2000.

Cursiefen et al., Angiogenesis in Corneal Disease: Histopathologic Evaluation of 254 Human Corneal Buttons with Neovascularization, *Cornea*, vol. 17 (6), pp. 611-613, Nov. 1, 1998.

D'Amore et al., Mechanisms of Angiogenesis, *Annual Review of Physiology*, vol. 49, pp. 453-464, Jan. 1, 1987.

Danis et al., Anti-Angiogenic Therapy of Proliferative Diabetic Retinopathy, Abstract Only, *Expert Opinion in Pharmacology*, vol. 2 (3), pp. 395-407, Mar. 1, 2001.

De Laey et al., Hyperlipofuscinosis and Subretinal Fibrosis in Stargardt's Disease, Abstract Only, *Retina*, vol. 15 (5), pp. 399-406, Jan. 1, 1995.

Dingli et al., Promising Preclinical Activity of 2-Methoxyestradiol in Multiple Myeloma, *Clinical Cancer Research*, vol. 8, pp. 3948-3954, Dec. 1, 2002.

Dubey et al., Estradiol Metabolites Inhibit Endothelin Synthesis by an Estrogen Receptor-Independent Mechanism, *Hypertension*, vol. 37 Part 2, pp. 640-644, Feb. 1, 2001.

Fajardo et al., Effects of Genistein and 2-Methoxyestradiol on Matrix Matalloproteinases and their Inhibitors Secreted by Ehrlich Ascites Tumor Cells, *Anticancer Research*, vol. 20, pp. 1691-1694, Jan. 1, 2000.

Farmer et al., Retinal Vasculitis Associated with Autoantibodies to Sjogren's Syndrome A Antigen (Abstract only-Applicants do not have complete copy), Abstract Only, *American Journal of Ophthalmology*, vol. 100 (6), pp. 814-821, Dec. 1, 1985.

Feher et al., Multiple Flexible Alignment with SEAL: A Study of Molecules Acting on the Colchincine Binding Site, *Journal of Chemical Information and Computer Sciences*, vol. 40, pp. 495-502, Jan. 1, 2000.

Friedlander et al., Involvement of Integrins αvβ3 and αvβ5 in Ocular Neovascular Diseases, *Proceedings of the National Academy of Science* (USA), vol. 93, pp. 9764-9769, Sep. 1, 1996.

Genentech USA, VEGF may be main cause of diabetic retinopathy (Abstract only-Applicants do not have complete copy), Abstract Only, *Biotechnology Newswatch*, pp. 13-14, Oct. 17, 1994.

Gleichmann et al., Immunoblastic Lymphadenopathy, Systemic Lupus Erythematosus, and Related Disorders. Possible Pathogenetic Pathways. (Abstract only-Applicants do not have complete copy), Abstract Only, *American Journal of Pathology*, vol. 72 (4), pp. 708-723, Oct. 1, 1979.

Hajjar et al., New Concepts in Fibrinolysis and Angiogenesis (Abstract only-Applicants do not have complete copy), Abstract Only, *Current Atherosclerosis Reports*, vol. 2 (5), pp. 417-421, Sep. 1, 2000.

Hamanaka et al., Retinal Ischemia and Angle Neovascularization in Proliferative Diabetic Retinopathy (Abstract only-Applicants do not have complete copy), Abstract Only, *American Journal of Ophthalmology*, vol. 132 (5), pp. 648-658, Nov. 1, 2001.

Hill et al., Pathogenesis of Pterygium (Abstract only-Applicants do not have complete copy), Abstract Only, *Eye*, vol. 3 (Pt 2), pp. 218-226, Jan. 1, 1990.

Hu et al., Interleukin-8 Stimulates Angiogenesis in Rats, *Inflammation*, vol. 17 (2), pp. 135-143, Apr. 1, 1993.

Hughes et al., 2-Methoxyestradiol and Analogs as Novel Antiproliferative Agents: Analysis of Three Dimensional Quantitative Structure-Activity Relationships for DNA Synthesis Inhibition and Estrogen Receptor Binding, *Molecular Pharmacology*, vol. 61 (5), pp. 1053-1069, Jan. 1, 2002.

Huober et al., Oral Administration of an Estrogen Metabolite-Induced Potentiation of Radiation Antitumor Effects of Presence of Wild-Type p53 in Non-Small-Cell Lung Cancer, *International Journal of Radiation Oncology, Biology, Physics*, vol. 48 (4), pp. 1127-1137, Jan. 1, 2000.

Jackson et al., The Codependence of Angiogenesis and Chronic Inflammation, Abstract Only, *The FASEB Journal*, vol. 11, pp. 457-465, Jan. 1, 1997.

Jampol et al., Peripheral Proliferation Retinopathies: An Update on Angiogenesis, Etiologies and Management (Abstract only-Applicants do not have complete copy), Abstract Only, *Survey of Ophthalmology*, vol. 38 (6), pp. 519-540, May 1, 1994.

Kachandourian et al., 2-Methoxyestradiol Does Not Inhibit Superoxide Dismutase, *Archives of Biochemistry and Biophysics*, vol. 392 (2), pp. 349-353, Aug. 15, 2001.

Kahlon et al., Angiogenesis in Atherosclerosis (Abstract only-Applicants do not have complete copy), Abstract Only, *Canadian Journal of Cardiology*, vol. 8 (1), pp. 60-64, Jan. 1, 1992.

Kalina et al., Neovascularization of the Disc in Pars Planitis (Abstract only-Applicants do not have complete copy), Abstract Only, *Retina*, vol. 10 (4), pp. 269-273, Jan. 1, 1990.

Karbowski et al., Opposite Effects of Microtubule-Stabilizing and Microtubule-Destabilizing Drugs on Biogenesis of Mitochondria in Mammalian Cells, *Journal of Cell Science*, vol. 114 (2), pp. 281-291, Oct. 27, 2000.

Kornmehl et al., Bilateral Keratitis in Lyme Diseases (Abstract only-Applicants do not have complete copy), Abstract Only, *Ophthalmology*, vol. 96 (8), pp. 1194-1197, Aug. 1, 1989.

Kumar et al., 2-Methoxyestradiol Blocks Cell-Cycle Progression at $G_2/M$ Phase and Inhibits Growth of Human Prostate Cancer Cells, *Molecular Carcinogenesis*, vol. 31, pp. 111-124, Jan. 1, 2001.

Lavigne et al., The Effects of Catechol-O-Methyltransferase Inhibition on Estrogen Metabolite and Oxidative DNA Damage Levels in Estradiol-Treated MCF-7 Cells, *Cancer Research*, vol. 61, pp. 7488-7494, Oct. 15, 2001.

Lee et al., Inhibition of Growth and Angiogenesis of Human Neurofibrosarcoma by Heparin and Hydrocortisone (Abstract only-Applicants do not have complete copy), Abstract Only, *Journal of Neurosurgery*, vol. 73 (3), pp. 429-435, Sep. 1, 1990.

Lee et al., Ocular Neovascularization: An Epidemiologic Review, *Survey of Ophthalmology*, vol. 43 (3), pp. 245-269, Nov. 1, 1998.

Leveille et al., Platelet-Induced Retinal Neovascularization in Leukemia (Abstract only-Applicants do not have complete copy), Abstract Only, *American Journal of Ophthalmology*, vol. 91 (5), pp. 640-644, May 1, 1981.

Lin et al., 2-Methoxyestradiol-Induced Caspace-3 Activation and Apoptosis Occurs Through $G_2/M$ Arrest Dependent and Independent Pathways in Gastric Carcinoma Cells, *Cancer*, vol. 92, pp. 500-509, Aug. 1, 2001.

Lin et al., Comparison of 2-Methoxyestradiol-Induced, Docetaxel-Induced, and Paclitaxel-Induced Apoptosis in Hepatoma Cells and Its Correlation with Reactive Oxygen Species, *Cancer*, vol. 89 (5), pp. 983-994, Sep. 1, 2000.

Lippert et al., The Impact of Endogenous Estradiol Metabolites on Carcinogenesis, *Steroids*, vol. 65, pp. 357-369, Jan. 1, 2000.

Locci et al., Angiogenesis: A New Diagnostic Aspect of Obsteric and Gynecologic Echography, *Journal of Perinatal Medicine*, vol. 21 (6), pp. 453-473, Jan. 1, 1993.

Lui et al., Male Predominance in Hepatocellular Carcinoma: New Insight and a Possible Therapeutic Alternative, *Medical Hypothesis*, vol. 55 (4), pp. 348-350, Jan. 1, 2000.

Macewen et al., 2-Methoxyestradiol (2ME2): In Vitro Apoptosis and Cell Cycle Inhibition and In Vivo Antitumor Activity in Canine Spontaneous Tumors, *American Association for Cancer Research -92nd Annual Meeting*, Abstract #20, Mar. 24, 2001.

Mahadevan et al., Metastasis and Angiogenesis, *Acta Oncologica*, vol. 29 (1), pp. 97-103, Jan. 1, 1990.

Mann et al., Choroidal Neovascularization with Granulomatous Inflammation in Ocular Histoplasmosis Syndrome (Abstract only-Applicants do not have complete copy), Abstract Only, *American Journal of Ophthalmology*, vol. 130 (2), pp. 247-250, Aug. 1, 2000.

Marti et al., Hypoxia-Induced Vascular Endothelial Growth Factor Expression Precedes Neovascularization after Cerebral Ischemia (Abstract only-Applicants do not have complete copy), Abstract Only, *American Journal of Pathology*, vol. 156 (3), pp. 965-976, Mar. 1, 2000.

Matsunaga et al., Angiogenesis from the Eighth Cranial Nerve to Vestibular Schwannomas (Abstract only-Applicants do not have complete copy), Abstract Only, *Acta Otolaryngology*, vol. 116 (1), pp. 52-58, Jan. 1, 1996.

Nelimarkka et al., Decorin is Produced by Capillary Endothelial Cells in Inflammation-Associated Angiogenesis (Abstract only-Applicants do not have complete copy), Abstract Only, *American Journal of Pathology*, vol. 158 (2), pp. 345-353, Feb. 1, 2001.

Nelson, J.D., Superior Limbic Keratoconjunctivitis (SLK) (Abstract only-Applicants do not have complete copy), Abstract Only, *Eye*, vol. 3 (Pt 2), pp. 180-189, Jan. 1, 1989.

Numazawa et al., Synthesis of 2-Methoxy- and 4-Methoxy-Estrogens with Halogen-Methoxy Exchange Reactions, *Journal of Chemical Research*, pp. 348-349, Jan. 1, 1985.

Paller et al., Responses to Anti-Angiogenic Therapies (Abstract only-Applicants do not have complete copy), Abstract Only, *Journal of Investigative Dermatology*, vol. 5 (1), pp. 83-86, Dec. 1, 2000.

Patz, A., Clinical and Experimental Studies on Retinal Neovascularization. XXXIX Edward Jackson Memorial Lecture. (Abstract only-Applicants do not have complete copy), Abstract Only), *American Journal of Ophthalmology*, vol. 94 (6), pp. 715-743, Dec. 1, 1982.

Penfold et al., Age-Related Macular Degeneration: Ultrastructural Studies of the Relationship of Leucocytes to Angiogenesis (Abstract only-Applicants do not have complete copy), Abstract Only, *Graefes Archive for Clinical and Experimental Ophthalmology*, vol. 225 (1), pp. 70-76, Jan. 1, 1987.

Penn et al., The Effect of Angiostatic Steroid on Neovascularization in a Rat Model of Retinopathy of Prematurity (Abstract only-Applicants do not have complete copy), Abstract Only, *Investigative Ophthalmology & Visual Science*, vol. 42 (1), pp. 283-290, Jan. 1, 2001.

Penn et al., Variable Oxygen Exposure Causes Preretinal Neovascularization in the Newborn Rat, *Investigative Ophthalmology & Visual Science*, vol. 34 (3), pp. 576-585, Mar. 1, 1993.

Potvin et al., Mechanisms of Action of Antimalarials in Inflammation: Induction of Apoptosis in Human Endothelial Cells (Abstract only-Applicants do not have complete copy), Abstract Only, *Journal of Immunobiology*, vol. 158 (4), pp. 1872-1879, Feb. 15, 1997.

Purohit et al., The Effect of 2-Methoxyestrone-3-O-Sulphamate on the Growth of Breast Cancer Cells and Induced Mammary Tumours, *International Journal of Cancer*, vol. 85, pp. 584-589, Jan. 1, 2000.

Ramirez et al., Estradiol, in the CNS, Targets Several Physiologically Relevant Membrane-Associated Proteins, *Brain Research Reviews*, vol. 37, pp. 141-152, Jan. 1, 2001.

Reddy et al., Ocular Complications of Adult Rheumatoid Arthritis (Abstract only-Applicants do not have complete copy), Abstract Only, *Rheumatology International*, vol. 16 (2), ppl 49-52, Jan. 1, 1996.

Reed et al., Aromatase Regulation and Breast Cancer, *Clinical Endocrinology*, vol. 54, pp. 563-571, Jan. 1, 2001.

Ribatti et al., Anti-Angiogenesis: A Multipurpose Therapeutic Tool?, *International Journal of Clinical & Laboratory Research*, vol. 23 (3), pp. 117-120, Jan. 1, 1993.

Riono et al., Scleritis: A Clinicopathologic Study of 55 Cases (Abstract only-Applicants do not have complete copy), Abstract Only, *Ophthalmology*, vol. 106 (7), pp. 1328-1333, Jul. 1, 1999.

Robinson et al., Retinal Vein Occlusion (Abstract only-Applicants do not have complete copy), Abstract Only, *American Family Physician*, vol. 45 (6), pp. 2661-2666, Jun. 1, 1992.

Rodi et al., Identification of Small Molecular Binding Sites within Proteins Using Phage Display Technology, *Combinatorial Chemistry & High Throughput*, vol. 4, pp. 553-572, Jan. 1, 2001.

Roth et al., Macular Translocation for Subfoveal Choroidal Neovascularization in Angioid Streaks (Abstract only-Applicants do not have complete copy), Abstract Only, *American Journal of Ophthalmology*, vol. 131 (3), pp. 390-392, Mar. 1, 2001.

Rowsey et al., Radial Keratotomy: Preliminary Report of Complications (Abstract only-Applicants do not have complete copy), Abstract Only, *Ophthalmic Surgery*, vol. 13 (1), pp. 27-35, Jan. 1, 1982.

Roy-Chaudhury et al., Venous Neoinitimal Hyperplasia in Polytetrafluoroethylene Dialysis Grafts (Abstract only-Applicants do not have complete copy), Abstract Only, *Kidney International*, vol. 59 (6), pp. 2325-2334, Jan. 11, 2001.

Sakaguchi et al., Trehalose 6,6'-Dimycolate (Cord Factor) Enhances Neovascularization through Vascular Endothelial Growth Factor Production by Neutrophils and Macrophages, *Infection and Immunity*, vol. 68 (4), pp. 2043-2052, Apr. 1, 2000.

Sanislo et al., Optic Nerve Head Neovascularization in a Patient with Inactive Cytomegalovirus Retinitis and Immune Recovery (Abstract only-Applicants do not have complete copy), Abstract Only, *American Journal of Ophthalmology*, vol. 126 (2), pp. 318-320, Aug. 1, 1998.

Shaub et al., Novel Agents that Promote Bone Regeneration (Abstract only-Applicants do not have complete copy), Abstract Only, *Current Opinion in Biotechnology*, vol. 2 (6), pp. 868-871, Dec. 1, 1991.

Servold, S.A., Growth Factor Impact on Wound Healing, *Clinics in Podiatric Medicine and Surgery*, vol. 8 (4), pp. 937-953, Oct. 1, 1991.

Shang et al., 2-Methoxyestradiol, an Endogenous Estradiol Metabolite, Differentially Inhibits Granulosa and Endothelial Cell Mitosis: A Potential Follicular Antiangiogenic Regulator, *Biology of Reproduction*, vol. 65, pp. 622-627, Jan. 1, 2001.

Sheela et al., Angiogenic and Invasive Properties of Neurofibroma Schwann Cells, Abstract Only, *Journal of Cell Biology*, vol. 111 (2), pp. 645-653, Aug. 1, 1990.

Shweiki et al., Patterns of Expression of Vascular Endothelial Growth Factor (VEGF) and VEGF Receptors in Mice Suggest a Role in Hormonally Regulated Angiogenesis (Abstract only-Applicants do not have complete copy), Abstract Only, *Journal of Clinical Investigation*, vol. 91 (5), pp. 2235-2243, May 1, 1993.

Simons, M., General Concepts of Angiogenesis, pp. 1-6, Apr. 17, 2000.

Sowka et al., Phlyctenulosis, *Handbook of Ocular Disease Management*, Jan. 1, 2000.

Spink et al., SULT1A1 Catalyzes 2-Methoxyestradiol Sulfonation in MCF-7 Breast Cancer Cells, *Carcinogenesis*, vol. 21 (11), pp. 1947-1957, Jan. 1, 2000.

Stiffey-Wilusz et al., An ex vivo Angiogenesis Assay Utilizing Commercial Porcine Carotid Artery: Modification of the Rat Aortic Ring Assay, *Angiogenesis*, vol. 4, pp. 3-9, Jan. 1, 2001.

Strizzi et al., Vascular Endothelial Growth Factor is an Autocrine Growth Factor in Human Malignant Mesothelioma (Abstract only-Applicants do not have complete copy), Abstract Only, *Journal of Pathology*, vol. 193 (4), pp. 468-475, Apr. 1, 2001.

Subbaramaiah et al., Microtubule-Interfering Agents Stimulate the Transcription of Cyclooxygenase-2, *The Journal of Biological Chemistry*, vol. 275 (20), pp. 14838-14845, May 19, 2000.

Sudoff et al., Angiogenesis and Angiogenic Growth Factors in Middle Ear Cholesteatoma (Abstract only-Applicants do not have complete copy), Abstract Only, *American Journal of Otolaryngology*, vol. 21 (6), pp. 793-798, Nov. 1, 2000.

Sun et al., In Vivo and in Vitro Characteristics of Interleukin 6-Transfeected B16 Melanoma Cells, *Cancer Research*, vol. 52, pp. 5412-5415, Oct. 1, 1992.

Sweeney et al., The Antiangiogenic Property of Docetaxel Is Synergistic with a Recombinant Humanized Monoclonal Antibody Against Vascular Endothelial Growth Factor or 2-Methoxyestradiol but Antagonized by Endothelial Growth Factors, *Cancer Research*, vol. 61, pp. 3369-3372, Apr. 15, 2001.

Tabbara, K.F., Disruption of the Choroidoretinal Interface by Toxoplasma (Abstract only-Applicants do not have complete copy), Abstract Only, *Eye*, vol. 4 (Part 2), pp. 366-373, Jan. 1, 1990.

Timar et al., Angiogenesis-Dependent Diseases and Angiogenesis Therapy (Abstract only-Applicants do not have complete copy), Abstract Only, *Pathology and Oncology Research*, vol. 7 (2), pp. 85-94, Jan. 1, 2001.

Tsutsui et al., Induction of Mammalian Cell Transformation of Genotoxicity by 2-Methoxyestradiol, an Endogenous Metabolite of Estrogen, *Carcinogenesis*, vol. 21 (4), pp. 735-740, Jan. 1, 2000.

Tuder et al., The Pathobiology of Pulmonary Hypertension. Endothelium, Abstract Only, *Clinicals in Chest Medicine*, vol. 22 (3), pp. 405-418, Sep. 1, 2001.

Turner et al., 2-Methoxyestradiol Inhibits Longitudinal Bone Growth in Normal Female Rats, *Calcified Tissue International*, vol. 66, pp. 465-469, Jan. 1, 2000.

Verdier-Pinard et al., A Steroid Derivative with Paclitaxel-Like Effects on Tubulin Polymerization, *Molecular Pharmacology*, vol. 57, pp. 568-575, Jan. 1, 2000.

Walsh et al., Angiogenesis in the Pathogenesis of Inflammatory Joint and Lung Diseases, *Arthritis Research*, vol. 3 (3), pp. 147-153, Jan. 1, 2001.

Wang et al., 2-Methoxyestradiol, an Endogenous Estrogen Metabolite, Induces Thyroid Cell Apoptosis, *Molecular and Cellular Endocrinology*, vol. 165, pp. 163-172, Jan. 1, 2000.

Watson, P.G., Management of Mooren's Ulceration (Abstract only-Applicants do not have complete copy), Abstract Only, *Eye*, vol. 11 (Pt 3), pp. 349-356, Jan. 1, 1997.

Wiedemann, P., Growth Factors in Reginal Disease: Proliferative Vitreoretinopathy, Proliferative Diabetic Retinopathy, and Retinal Degeneration (Abstract only-Applicants do not have complete copy), Abstract Only, *Survey of Ophthalmology*, vol. 36 (5), pp. 373-384, Mar. 1, 1992.

Xiao et al., Effects of Estradiol and Its Metabolites on Glomerular Endothelial Nitric Oxide Synthesis and Mesangial Cell Growth, *Hypertension*, vol. 37 (part 2), pp. 645-650, Feb. 1, 2001.

Yazaki et al., Inhibition of Angiogenesis and Growth of Human Non-Malignant and Malignant Meningiomas by TNP-470 (Abstract only-Applicants do not have complete copy), Abstract Only, *Journal of Neurooncology*, vol. 23 (1), pp. 23-29, Jan. 1, 1995.

Zacharia et al., Catecholamines Abrogate Antimitogenic Effects of 2-Hydroxyestradiol on Human Aortic Vascular Smooth Muscle Cells, *Arteriosclerosis, Thrombosis and Vascular Biology*, vol. 21, pp. 1745-1750, Nov. 1, 2001.

Zacharia et al., Increased 2-Methoxyestradiol Production in Human Coronary Versus Aortic Vascular Cells, *Hypertension*, vol. 37 (part 2), pp. 658-662, Feb. 1, 2001.

Zheng et al., Control of Stromal Keratitis by Inhibition of Neovascularization (Abstract only-Applicants do not have complete copy), Abstract Only, *American Journal of Pathology*, vol. 159 (3), pp. 1021-1029, Sep. 1, 2001.

U.S. Appl. No. 11/701,809, filed Feb. 2, 2007 (Copy enclosed).

U.S. Appl. No. 11/599,997, filed Nov. 14, 2006 (Copy enclosed).

\* cited by examiner

ESTRADIOL DERIVATIVES AND PHARMACEUTICAL COMPOSITIONS USING SAME

CROSS-REFERENCE TO RELATED APPLICATION

The present application claims benefit of provisional patent application Ser. No. 60/474,288 filed May 28, 2003.

FIELD OF THE INVENTION

The present invention relates to treating disease states characterized by abnormal cell mitosis and to treating disease states characterized by abnormal angiogenesis and to treating disease states characterized by a combination of these events. More particularly, the present invention relates to analogs of 2-methoxyestradiol ($2ME_2$) and their effect on diseases characterized by abnormal cell mitosis and/or abnormal angiogenesis.

BACKGROUND OF THE INVENTION

Angiogenesis is the generation of new blood vessels into a tissue or organ. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Angiogenesis is controlled through a highly regulated system of angiogenic stimulators and inhibitors. The control of angiogenesis has been found to be altered in certain disease states and, in many cases, pathological damage associated with the diseases is related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, unregulated angiogenesis occurs in many disease states, tumor metastases, and abnormal growth by endothelial cells. The diverse pathological disease states in which unregulated angiogenesis is present have been grouped together as angiogenic-dependent or angiogenic-associated diseases.

One example of a disease dependent on angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma, and retrolental fibroplasia. Other diseases associated with corneal neovascularization include, but are not limited to, epidemic keratoconjunctivitis, Vitamin A deficiency, contact lens overwear, atopic keratitis, superior limbic keratitis, and pterygium keratitis sicca. Other diseases associated with undesirable angiogenesis include Sjögren's syndrome, acne rosacea, phylectenulosis, syphilis, Mycobacteria infections, lipid degeneration, chemical burns, bacterial ulcers, fungal ulcers, Herpes simplex infection, Herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson's disease, pemphigoid, and radial keratotomy.

Diseases associated with neovascularization include, but are not limited to, retinal/choroidal neovascularization, diabetic retinopathy, macular degeneration, sickle cell anemia, sarcoidosis, syphilis, pseudoxanthoma elasticum, Paget's disease, vein occlusion, artery occlusion, carotid obstructive disease, chronic uveitis/vitritis, Mycobacteria infections, lyme's disease, systemic lupus erythematosus, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other eye-related diseases include, but are not limited to, diseases associated with rubeosis (neovascularization of the angle) and diseases caused by the abnormal proliferation of fibrovascular or fibrous tissue, including all forms of prolific vitreoretinopathy.

Another angiogenesis associated disease is rheumatoid arthritis. The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the cartilage destruction could halt the progress of the disease and provide relief for persons suffering with arthritis.

Chronic inflammation may also involve pathological angiogenesis. Such diseases as ulcerative colitis and Crohn's disease show histological changes with the ingrowth of new blood vessels into inflamed tissues. Bartonelosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

The hypothesis that tumor growth is angiogenesis-dependent was first proposed in 1971. (Folkman, *New Eng. J Med.*, 285:1182-86 (1971)). In its simplest terms, this hypothesis states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire, et al., *J. Nat. Cancer Inst.*, 6:73-85 (1945)).

(2) Tumors grown in isolated perfused organs where blood vessels do not proliferate are limited to 1-2 $mm^3$ but expand rapidly to >1000 times this volume when they are transplanted to mice and become neovascularized. (Folkman, et al., *Annals of Surgery*, 164:491-502 (1966)).

(3) Tumor growth in the avascular cornea proceeds slowly and at a linear rate, but switches to exponential growth after neovascularization. (Gimbrone, Jr., et al., *J. Nat. Cancer Inst.*, 52:421-27 (1974)).

(4) Tumors suspended in the aqueous fluid of the anterior chamber of a rabbit eye remain viable, avascular, and limited in size to <1 $mm^3$. Once they are implanted on the iris vascular bed, they become neovascularized and grow rapidly, reaching 16,000 times their original volume within 2 weeks. (Gimbrone, Jr., et al., *J. Exp. Med.*, 136:261-76).

(5) When tumors are implanted on a chick embryo chorio-allantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton, *British J. Cancer*, 35:347-56 (1977)).

(6) Vascular casts of metastases in a rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien, et al., *Surgery*, 68:334-40 (1970)).

(7) In transgenic mice that develop carcinomas in the beta cells of the pancreatic islets, pre-vascular hyperplastic islets are limited in size to <1 mm. At 6-7 weeks of age, 4-10% of the islets become neovascularized, and from these islets arise large vascularized tumors of more than 1000 times the volume of the pre-vascular islets. (Folkman, et al., *Nature*, 339:58-61 (1989)).

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim, et al., *Nature*, 362:841-44 (1993)).

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori, et al., *Cancer Res.*, 51:6180-84 (1991)).

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumor cells in vitro. (Gross, et al., *Proc. Am. Assoc. Cancer Res.*, 31:79 (1990)).

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber, et al., *Nature*, 48:555-57 (1990)). There is also indirect clinical evidence that tumor growth is angiogenesis dependent.

(12) Human retinoblastomas that are metastatic to the vitreous develop into avascular spheroids that are restricted to less than 1 $mm^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1-3 $mm^3$). These implants rarely grow larger until one or more of them becomes neovascularized.

(14) Intensity of neovascularization in breast cancer (Weidner, et al., *New Eng. J. Med.*, 324:1-8 (1991); Weidner, et al., *J. Nat. Cancer Inst.*, 84:1875-87 (1992)) and in prostate cancer (Weidner, et al., *Am. J. Pathol.*, 143(2):401-09 (1993)) correlates highly with risk of future metastasis.

(15) Metastasis from human cutaneous melanoma is rare prior to neovascularization. The onset of neovascularization leads to increased thickness of the lesion and an increased risk of metastasis. (Srivastava, et al., *Am. J. Pathol.*, 133: 419-23 (1988)).

(16) In bladder cancer, the urinary level of an angiogenic protein, bFGF, is a more sensitive indicator of status and extent of disease than is cytology. (Nguyen, et al., *J. Nat. Cancer Inst.*, 85:241-42 (1993)).

Thus, it is clear that angiogenesis plays a major role in the metastasis of cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis is also associated with blood-borne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed that angiogenesis plays a role in the abnormalities in the bone marrow that give rise to leukemia tumors and multiple myeloma diseases.

One of the most frequent angiogenic diseases of childhood is the hemangioma. A hemangioma is a tumor composed of newly formed blood vessels. In most cases the tumors are benign and regress without intervention. In more severe cases, the tumors progress to large cavernous and infiltrative forms and create clinical complications. Systemic forms of hemangiomas, hemangiomatoses, have a high mortality rate. Therapy-resistant hemangiomas exist that cannot be treated with therapeutics currently in use.

Angiogenesis is also responsible for damage found in heredity diseases such as Osler-Weber-Rendu disease, or heredity hemorrhagic telangiectasia. This is an inherited disease characterized by multiple small angiomas, tumors of blood or lymph vessels. The angiomas are found in the skin and mucous membranes, often accompanied by epitaxis (nose bleeds) or gastrointestinal bleeding and sometimes with pulmonary or hepatitic arteriovenous fistula.

What is needed, therefore, is a composition and method that can inhibit angiogenesis. What is also needed is a composition and method that can inhibit the unwanted growth of blood vessels, especially in tumors.

Angiogenesis is also involved in normal physiological processes, such as reproduction and wound healing. Angiogenesis is an important step in ovulation and also in implantation of the blastula after fertilization. Prevention of angiogenesis could be used to induce amenorrhea, to block ovulation, or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several compounds have been used to inhibit angiogenesis. Taylor, et al. (*Nature,* 297:307 (1982)) have used protamine to inhibit angiogenesis. The toxicity of protamine limits its practical use as a therapeutic. Folkman, et al. (*Science,* 221:719 (1983), and U.S. Pat. Nos. 5,001,116 and 4,994,443) have disclosed the use of heparin and steroids to control angiogenesis. Steroids, such as tetrahydrocortisol, which lack glucocorticoid and mineralocorticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors, such as interferon, inhibit angiogenesis. For example, interferon alpha or human interferon beta have been shown to inhibit tumor-induced angiogenesis in mouse dermis stimulated by human neoplastic cells. Interferon beta is also a potent inhibitor of angiogenesis induced by allogeneic spleen cells. (Sidky, et al., *Cancer Res.,* 47:5155-61 (1987)). Human recombinant interferon (alpha/A) was reported to be successfully used in the treatment of pulmonary hemangiomatosis, an angiogenesis-induced disease. (White, et al., *New Eng. J. Med.,* 320:1197-1200 (1989)).

Other agents that have been used to inhibit angiogenesis include ascorbic acid ethers and related compounds. (Japanese Kokai Tokkyo Koho No.58-13 (1978)). Sulfated polysaccharide DS 4152 also inhibits angiogenesis. (Japanese Kokai Tokkyo Koho No. 63-119500). Additional anti-angiogenic compounds include Angiostatin® (U.S. Pat. Nos. 5,639,725; 5,792,845; 5,885,795; 5,733,876; 5,776,704; 5,837,682; 5,861,372, and 5,854,221) and Endostatin (U.S. Pat. No. 5,854,205).

Another compound which has been shown to inhibit angiogenesis is thalidomide. (D'Amato, et al., *Proc. Natl. Acad. Sci.,* 90:4082-85 (1994)). Thalidomide is a hypnosedative that has been successfully used to treat a number of diseases, such as rheumatoid arthritis (Gutierrez-Rodriguez, *Arthritis Rheum.,* 27 (10):1118-21 (1984); Gutierrez-Rodriguez, et al., *J. Rheumatol.,* 16(2):158-63 (1989)), Behcet's disease (Handley, et al., *Br. J. Dermatol.,* 127 Suppl, 40:67-8 (1992); Gunzler, *Med. Hypotheses,* 30(2):105-9 (1989)).

Although thalidomide has minimal side effects in adults, it is a potent teratogen. Thus, there are concerns regarding its use in women of child-bearing age. Although minimal, there are a number of side effects that limit the desirability of thalidomide as a treatment. One such side effect is drowsiness. In a number of therapeutic studies, the initial dosage of thalidomide had to be reduced because patients became lethargic and had difficulty functioning normally. Another side effect limiting the use of thalidomide is peripheral neuropathy, in which individuals suffer from numbness and dysfunction in their extremities.

Thus, improved methods and compositions are needed that are easily administered and capable of inhibiting angiogenesis. What is needed are safe and effective treatments that do not create unwanted side effects.

2-Methoxyestradiol is an endogenous metabolite of estradiol (E2). When administered orally, it exhibits anti-tumor and anti-proliferative activity with little toxicity. In vitro data suggests that 2-methoxyestradiol does not engage the estrogen receptor for its anti-proliferative activity and is not estrogenic over a wide range of concentrations, as assayed by estrogen dependant MCF-7 cell proliferation. However, the presence of metabolizing enzymes, such as demethylases, in vivo and in vitro may metabolize this compound to products, such as 2-hydroxyestradiol, which has been shown to be estrogenic by several approaches. What is needed is a means to improve the bioavailibility of estradiol derivatives or 2-methoxyestradiol and to reduce the formation of estrogenic 2-methoxyestradiol metabolites. What is also needed is a means to modify estradiol derivatives or 2-methoxyestradiol in such a way as to prevent conversion into an estrogenic derivative, metabolic conjugation and/or conversion to estrones.

SUMMARY OF THE INVENTION

The present invention provides certain analogs of 2-methoxyestradiol that are effective in treating diseases characterized by abnormal mitosis and/or abnormal angiogenesis. Specifically the present invention relates to analogs of 2-methoxyestradiol that have been modified at the 2, 3 and 17 positions thereof. Compounds within the general formulae that inhibit cell proliferation are preferred. Compounds within Formula I that inhibit angiogenesis are also preferred. Preferred compositions may also exhibit a change (increase or decrease) in estrogen receptor binding, improved absorption, transport (e.g., through blood-brain barrier and cellular membranes), biological stability, or decreased toxicity. The invention also provides compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease). Other undesired angiogenesis involves normal processes including ovulation and implantation of a blastula.

Accordingly, the compositions described above can be used to block ovulation and implantation of a blastula or to block menstruation (induce amenorrhea).

A novel series of compounds have been prepared that retain the biological activities of $2ME_2$ but are believed to have reduced metabolism. 17-Position alkylated analogs lack the hydroxyl moiety and cannot be metabolized to estrones or conjugated at that position but retain antiproliferative activity in HUVEC and tumor cells. Replacement of the 2-methoxy group by other moieties, such as a propynyl group, retains antiproliferative activity, but these groups cannot be de-methylated to yield the estrogenic 2-hydroxyl derivatives. Contrary to what is observed with $2ME_2$, several of these new analogs have selective in vitro antiproliferative activity for the endothelial cells over the tumor cell line assessed.

Also disclosed are compounds and methods for altering the chemical nature of positions 3 and 17 of 2-methoxyestradiol for preventing conversion to 2-methoxyestrone and/or the conjugation of 2-methoxyestradiol (or metabolites) with other molecules and subsequent loss during excretion of the resulting compounds.

Other features and advantages of the invention will be apparent from the following description of preferred embodiments thereof.

DETAILED DESCRIPTION OF THE INVENTION

As described below, compounds that are useful in accordance with the invention include novel 2-methoxyestradiol derivatives that exhibit anti-mitotic, anti-angiogenic and/or anti-tumor properties. Preferred compounds of the invention are 2-methoxyestradiol derivatives modified at the 2, 3 and 17 positions. Preferred compounds are those of the general Formula (I):

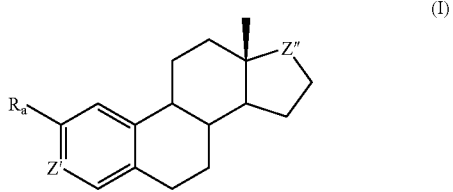

(I)

wherein, $R_a$ is selected from —OCH$_3$, —OCH$_2$CH$_3$, or —CCCH$_3$; Z' is selected from >C—F, >C—NH$_2$, >CCONH$_2$, >C—NHCOH, >C—OSO$_2$NH$_2$, or >C—CHCH$_2$; and Z" is selected from >C(H$_2$), >C(H)—CH$_3$, >C=CH$_2$, >C=CHCH$_3$, or >C=O; provided that when Z' is >C—OSO$_2$NH$_2$ and Z" is >C(H$_2$) or >C=O, $R_a$ is neither —OCH$_3$ nor —OCH$_2$CH$_3$. Specific compounds according to the invention are described below.

In an alternate disclosed embodiment of the present invention, compounds according to the present invention are those of Formula I, wherein $R_a$ is —OCH$_3$; Z' is selected from >C—NH$_2$, >CCONH$_2$, >C—NHCOH, >C—OSO$_2$NH$_2$, or >C—CHCH$_2$; and Z" is selected from >C(H$_2$), >C(H)—CH$_3$, >C=CH$_2$, >C=CHCH$_3$, or >C=O.

In another alternate disclosed embodiment of the present invention, compounds according to the present invention are those of Formula I, wherein $R_a$ is —OCH$_2$CH$_3$; Z' is selected from >C—NH$_2$, >CCONH$_2$, >C—NHCOH, >C—OSO$_2$NH$_2$, or >C—CHCH$_2$; and Z" is selected from >C(H$_2$), >C(H)—CH$_3$, >C=CH$_2$, >C=CHCH$_3$, or >C=O.

In a further alternate disclosed embodiment of the present invention, compounds according to the present invention are those of Formula I, wherein $R_a$ is —CCCH$_3$; Z' is selected from >C—NH$_2$, >CCONH$_2$, >C—NHCOH, >C—OSO$_2$NH$_2$, or >C—CHCH$_2$; and Z" is selected from >C(H$_2$), >C(H)—CH$_3$, >C=CH$_2$, >C=CHCH$_3$, or >C=O.

In another alternate disclosed embodiment of the present invention, compounds according to the present invention are those of Formula I, wherein Z' is selected from >C—F; $R_a$ is selected from —OCH$_3$, —OCH$_2$CH$_3$, or —CCCH$_3$; and Z" is selected from >C(H$_2$), >C(H)—CH$_3$, >C=CH$_2$, >C=CHCH$_3$, or >C=O.

In another alternate disclosed embodiment of the present invention, compounds according to the present invention are those of Formula I, wherein Z' is >C—NH$_2$; $R_a$ is selected from —OCH$_3$, —OCH$_2$CH$_3$, or —CCCH$_3$; and Z" is selected from >C(H$_2$), >C(H)—CH$_3$, >C=CH$_2$, >C=CHCH$_3$, or >C=O.

In still another alternate disclosed embodiment of the present invention, compounds according to the present invention are those of Formula I, wherein Z' is selected from >CCONH$_2$; $R_a$ is —OCH$_3$, —OCH$_2$CH$_3$, or —CCCH$_3$; and Z" is selected from >C(H$_2$), >C(H)—CH$_3$, >C=CH$_2$, >C=CHCH$_3$, or >C=O.

In a further alternate disclosed embodiment of the present invention, compounds according to the present invention are those of Formula I, wherein Z' is selected from >C—OSO$_2$NH$_2$; $R_a$ is —OCH$_3$, —OCH$_2$CH$_3$, or —CCCH$_3$; and Z" is selected from >C(H$_2$), >C(H)—CH$_3$, >C=CH$_2$, >C=CHCH$_3$, or >C=O.

In another alternate disclosed embodiment of the present invention, compounds according to the present invention are those of Formula I, wherein Z' is selected from >C—CHCH$_2$; $R_a$ is —OCH$_3$, —OCH$_2$CH$_3$, or —CCCH$_3$; and Z" is selected from >C(H$_2$), >C(H)—CH$_3$, >C=CH$_2$, >C=CHCH$_3$, or >C=O.

In yet alternate disclosed embodiment of the present invention, compounds according to the present invention are those of Formula I, wherein Z" is selected from >C(H$_2$); $R_a$ is selected from —OCH$_3$, —OCH$_2$CH$_3$, or —CCCH$_3$; and Z' is selected from >C—NH$_2$, >CCONH$_2$, >C—NHCOH, >C—OSO$_2$NH$_2$, or >C—CHCH$_2$.

In another alternate disclosed embodiment of the present invention, compounds according to the present invention are those of Formula I, wherein Z" is selected from >C(H)—CH$_3$; $R_a$ is selected from —OCH$_3$, —OCH$_2$CH$_3$, or —CCCH$_3$; and Z' is selected from >C—NH$_2$, >CCONH$_2$, >C—NHCOH, >C—OSO$_2$NH$_2$, or >C—CHCH$_2$.

In a further alternate disclosed embodiment of the present invention, compounds according to the present invention are those of Formula I, wherein Z" is selected from >C=CH$_2$; $R_a$ is selected from —OCH$_3$, —OCH$_2$CH$_3$, or —CCCH$_3$; and Z' is selected from >C—NH$_2$, >CCONH$_2$, >C—NHCOH, >C—OSO$_2$NH$_2$, or >C—CHCH$_2$.

In another alternate disclosed embodiment of the present invention, compounds according to the present invention are those of Formula I, wherein Z" is selected from >C=CHCH$_3$; $R_a$ is selected from —OCH$_3$, —OCH$_2$CH$_3$, or —CCCH$_3$; and Z' is selected from >C—NH$_2$, >CCONH$_2$, >C—NHCOH, >C—OSO$_2$NH$_2$, or >C—CHCH$_2$.

In still another alternate disclosed embodiment of the present invention, compounds according to the present invention are those of Formula I, wherein Z" is selected from >C=O; $R_a$ is selected from —OCH$_3$, —OCH$_2$CH$_3$, or —CCCH$_3$; and Z' is selected from >C—NH$_2$, >CCONH$_2$, >C—NHCOH, >C—OSO$_2$NH$_2$, or >C—CHCH$_2$.

In a further alternate disclosed embodiment of the present invention, compounds according to the present invention are those of Formula I, wherein $R_a$ is selected from —OCH$_3$, —OCH$_2$CH$_3$, or —CCCH$_3$; Z' is selected from >C—NH$_2$, >CCONH$_2$, >C—NHCOH, or >C—CHCH$_2$; and Z" is selected from >C(H$_2$), >C(H)—CH$_3$, >C=CH$_2$, >C=CHCH$_3$, or >C=O.

In another alternate disclosed embodiment of the present invention, compounds according to the present invention are those of Formula I, wherein $R_a$ is selected from —OCH$_3$, —OCH$_2$CH$_3$, or —CCCH$_3$; Z' is selected from >C—NH$_2$, >CCONH$_2$, >C—NHCOH, >C—OSO$_2$NH$_2$, or >C—CHCH$_2$; and Z" is selected from >C(H$_2$), >C(H)—

$CH_3$, >C=$CH_2$, >C=$CHCH_3$, or >C=O; provided that when Z' is >C—$OSO_2NH_2$, Z" is neither >C($H_2$) nor >C=O.

Those skilled in the art will appreciate that the invention extends to other compounds within the formulae given in the claims below, having the described characteristics. These characteristics can be determined for each test compound using the assays detailed below and elsewhere in the literature.

Although not wishing to be bound by theory, it is believed that 2-methoxyestrone ($2ME_1$) is formed through the same enzymatic pathway as estrone is formed from estradiol. Although not wishing to be bound by theory, it is further believed that the enzymes responsible for this reaction on estradiol are the 17β-hydroxysteroid dehydrogenases (17β-HSD), which utilize NADP+ as a co-factor (Han et al., *J. Biol. Chem.* 275:2, 1105-1111 (Jan. 12, 2000) and other references cited earlier). Each of the four members of this enzyme family, types 1, 2, 3, and 4 have distinct activity. It appears that 17β-HSD type 1 catalyzes the reductive reaction (estrone to estradiol), while 17β-HSD type 2 catalyzes the oxidation reaction (estradiol to estrone), and type 3 catalyzes 4-androstenedione to testosterone. It is also believed that an additional metabolic deactivation pathway results in conjugation of 2-methoxyestradiol or 2-methoxyestrone with molecules such as sulfate or glucuronic acid and subsequent loss via excretion. In this invention, positions 3 and 17 of 2-methoxyestradiol, and derivatives thereof, may be modified to prevent these metabolic pathways from occurring.

Since 2-methoxyestradiol is metabolized to a much less active metabolite, the present invention adds steric bulk and/or modification of chemical or electrostatic characteristics at positions 3 and 17 of 2-methoxyestradiol for retarding or preventing interaction of the family of 17β-hydroxysteroid dehydrogenases and co-factor $NADP^+$ on this substrate. Addition of steric bulk and/or modification of chemical or electrostatic characteristics at positions 3 and 17 of 2-methoxyestradiol may also retard or prevent conjugation, such as glucuronidation or sulfation. It is believed that retardation or prevention of these two metabolic deactivation pathways prolongs the serum lifetime of 2-methoxyestradiol and other estradiol derivatives while retaining the desired anti-angiogenic and anti-tumor activity.

Aside from preventing the possible metabolism of $2ME_2$ to $2ME_1$, which may occur by making these steroids poor substrates for 17β-HSD (by either steric and/or electronic effects), it is not possible for some of these analogs modified at the 2 position to undergo the demethylation known to occur with $2ME_2$ since there is no methyl ether group at that position. This is desirable since it has been demonstrated that 2-hydroxyestradiol (the product of demethylation of $2ME_2$) has estrogenic activity.

It is well known that orally-delivered steroids, such as estradiol ($E_2$) and ethynyl-$E_2$, are extensively metabolized during passage through the gastrointestinal tract and by first-pass metabolism in the liver. Two major metabolic pathways that lead to rapid deactivation and excretion are well studied (Fotsis, T.; Zhang, Y.; Pepper, M. S.; Adlercutz, H.; Montesano, R.; Nawreth. P. P.; Schweigerer, L., The Endogenous Estrogen Metabolite 2-Methoxyestradiol Inhibits Angiogenesis and Suppresses Tumor. *Nature*, 1994, 368, 237-239; Wang, Z.; Yang, D.; Mohanakrishnan, A. K.; Fanwick, P. E.; Nampoothiri, P.; Hamel, E.; Cushman, M. "Synthesis of B-Ring Homologated Estradiol Analogs that Modulate Tubulin Polymerization and Microtubule Stability." *J. Med. Chem.*, 2000, 43, 2419-2429) e.g. oxidation at the D-ring's 17-hydroxy group of $E_2$ to form estrone and conjugation with sulfate and/or glucuronate at the hydroxyls of position-3 on the A-ring and position-17 on the D-ring.

Several studies have been conducted to determine SAR of $2ME_2$ analogs (D'Amato, R. J.; Lin, C. M.; Flynn, E.; Folkman, J.; Hamel, E. Inhibition of Angiogenesis and Breast Cancer in Mice by the Microtubule Inhibitors 2-Methoxyestradiol and Taxol", *Cancer Res.*, 1997, 57, 81-86; Cushman, M.; He, M.-H.; Katzenellenbogen, J. A.; Lin, C. M.; Hamel, E. "Synthesis, Antitubuln and Antimitotic Activity, and Cytotoxicity of Analogs of 2-Methoxyestradiol, an Endogenous Mammalian Metabolite of Estradiol that inhibits Tubulin Polymerization by Binding to the Colchicine Binding Site." *J. Med. Chem.* 1995, 38, 2041-2049) but none to reduce or stop its metabolic pathway.

In the preferred embodiment of the invention, 2-methoxyestradiol, and derivatives thereof, are modified at the 3 and 17 positions.

Anti-Proliferative Activity In Situ

Anti-proliferative activity can be evaluated in situ by testing the ability of an improved estradiol derivative to inhibit the proliferation of new blood vessel cells (angiogenesis). A suitable assay is the chick embryo chorioallantoic membrane (CAM) assay described by Crum et al. *Science* 230:1375 (1985). See also, U.S. Pat. No. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 μg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and/or angiogenesis.

Anti-Proliferative Activity In Vitro

The process by which $2ME_2$ affects cell growth remains unclear, however, a number of studies have implicated various mechanisms of action and cellular targets. $2ME_2$ induced changes in the levels and activities of various proteins involved in the progression of the cell cycle. These include cofactors of DNA replication and repair, e.g., proliferating cell nuclear antigen (PCNA) (Klauber, N., Parangi, S., Flynn, E., Hamel, E. and D'Amato, R. J. (1997), Inhibition of angiogenesis and breast cancer in mice by the microtubule inhibitors 2-methoxyestradiol and Taxol., Cancer Research 57, 81-86; Lottering, M-L., de Kock, M., Viljoen, T. C., Grobler, C. J. S. and Seegers, J. C. (1996) 17β-Estradiol metabolites affect some regulators of the MCF-7 cell cycle. Cancer Letters 110, 181-186); cell division cycle kinases and regulators, e.g., $p34^{cdc2}$ and cyclin B (Lottering et al. (1996); Attalla, H., Mäkelä, T. P., Adlercreutz, H. and Andersson, L. C. (1996) 2-Methoxyestradiol arrests cells in mitosis without depolymerizing tubulin. Biochemical and Biophysical Research Communications 228, 467-473; Zoubine, M. N., Weston, A. P., Johnson, D. C., Campbell, D. R. and Banerjee, S. K. (1999) 2-Methoxyestradiol-induced growth suppression and lethality in estrogen-responsive MCF-7 cells may be mediated by down regulation of p34cdc2 and cyclin B1 expression. Int J Oncol 15, 639-646); transcription factor modulators, e.g., SAPK/JNK (Yue, T-L., Wang, X., Louden, C. S., Gupta, L. S., Pillarisetti, K., Gu, J-L., Hart, T. K., Lysko, P. G. and Feuerstein, G. Z. (1997) 2-Methoxyestradiol, an endogenous estrogen metabolite induces apoptosis in endothelial cells and inhibits angiogenesis: Possible role for stress-activated protein kinase signaling pathway and fas expression. Molecular Pharmacology 51, 951-962; Attalla, H., Westberg, J. A., Andersson, L. C., Aldercreutz, H. and Makela, T. P. (1998) 2-Methoxyestradiol-induced phosphorylation of bcl-2: uncoupling from JNK/SAPK activation. Biochem and Biophys Res Commun 247, 616-619); and regulators of cell arrest and apoptosis, e.g., tubulin (D'Amato, R. J., Lin, C. M., Flynn, E., Folkman, J. and Hamel, E. (1994) 2-Methoxyestradiol, and endogenous mammalian metabolite, inhibits tubulin polymerization by interacting at the colchicine site. Proc. Natl. Acad. Sci. USA 91, 3964-3968; Hamel, E., Lin, C. M., Flynn, E. and D'Amato, R. J. (1996) Interactions of 2-methoxyestradiol, and endogenous mammalian metabolite, with unpolymerized tubulin and with tubulin polymers. Biochemistry 35, 1304-1310), p21$^{WAF1/CIP1}$ (Mukhopadhyay, T. and Roth, J. A. (1997) Induction of apoptosis in human lung cancer cells after wild-type p53 activation by methoxyestradiol. Oncogene 14, 379-384), bcl-2 and FAS (Yue et al. (1997); Attalla et al. (1998)), and p53 (Kataoka, M., Schumacher, G., Cristiano, R. J., Atkinson, E. N., Roth, J. A. and Mukhopadhyay, T. (1998) An agent that increases tumor suppressor transgene product coupled with systemic transgene delivery inhibits growth of metastatic lung cancer in vivo. Cancer Res 58, 4761-4765; Mukhopadhyay et al. (1997); Seegers, J. C., Lottering, M-L., Grobler C. J. S., van Papendorp, D. H., Habbersett, R. C., Shou, Y. and Lehnert B. E. (1997) The mammalian metabolite, 2-methoxyestradiol, affects p53 levels and apoptosis induction in transformed cells but not in normal cells. J. Steroid Biochem. Molec. Biol. 62, 253-267). The effects on the level of cAMP, calmodulin activity and protein phosphorylation may also be related to each other. More recently, 2ME$_2$ was shown to upregulate Death Receptor 5 and caspase 8 in human endothelial and tumor cell lines (LaVallee T M, Zhan X H, Johnson M S, Herbstritt C J, Swartz G, Williams M S, Hembrough W A, Green S J, Pribluda V S. 2-methoxyestradiol up-regulates death receptor 5 and induces apoptosis through activation of the extrinsic pathway. Cancer Res. (2003) 63#2:468-75). Additionally, 2ME2 has been shown to interact with superoxide dismutase (SOD) 1 and SOD 2 and to inhibit their enzymatic activities (Huang, P., Feng, L., Oldham, E. A., Keating, M. J., and Plunkett, W. 2000. Superoxide dismutase as a target for the selective killing of cancer cells, Nature. 407:390-5.). All cellular targets described above are not necessarily mutually exclusive to the inhibitory effects of 2ME$_2$ in actively dividing cells.

The high affinity binding of 2ME$_2$ to SHBG has been mechanistically associated to its efficacy in a canine model of prostate cancer, in which signaling by estradiol and 5α-androstan-3α,17β-diol were inhibited by 2ME$_2$ (Ding, V. D., Moller, D. E., Feeney, W. P., Didolkar, V., Nakhla, A. M., Rhodes, L., Rosner, W. and Smith, R. G., *Sex hormone-binding globulin mediates prostate androgen receptor action via a novel signaling pathway*, Endocrinology 139, 213-218 (1998)).

The more relevant mechanisms described above have been extensively discussed in Victor S. Pribluda, Theresa M. LaVallee and Shawn J. Green, 2-*Methoxyestradiol: A novel endogenous chemotherapeutic and antiangiogenic* in The New Angiotherapy, Tai-Ping Fan and Robert Auerbach eds., Human Press Publisher.

Assays relevant to these mechanisms of action and inhibition of cell proliferation are well-known in the art. For example, anti-mitotic activity mediated by effects on tubulin polymerization activity can be evaluated by testing the ability of an estradiol derivative to inhibit tubulin polymerization and microtubule assembly in vitro. Microtubule assembly can be followed in a Gilford recording spectrophotometer (model 250 or 2400S) equipped with electronic temperature controllers. A reaction mixture typically contains 1.0 M monosodium glutamate (pH 6.6), 1.0 mg/ml (10 μM) tubulin, 1.0 mM MgCl$_2$, 4% (v/v) dimethylsulfoxide and 20-75 μM of a composition to be tested. The reaction mixtures are incubated for 15 min. at 37° C. and then chilled on ice. After addition of 10 μl 2.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 nm. Alternatively, inhibition of microtubule assembly can be followed by transmission electron microscopy as described in Example 2 of U.S. Pat. Nos. 5,504,074, 5,661,143, and 5,892,069, the disclosures of which are incorporated herein by reference.

Other such assays include counting of cells in tissue culture plates or assessment of cell number through metabolic assays or incorporation into DNA of labeled (radiochemically, for example $^3$H-thymidine, or fluorescently labeled) or immuno-reactive (BrdU) nucleotides. In addition, antiangiogenic activity may be evaluated through endothelial cell migration, endothelial cell tubule formation, or vessel outgrowth in ex-vivo models such as rat aortic rings.

Indications

The invention can be used to treat any disease characterized by abnormal cell mitosis and/or abnormal angiogenesis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, skin diseases, such as psoriasis, diabetic retinopathy, and other ocular angiogenic diseases such as retinopathy of prematurity (retrolental fibroplasic), macular degeneration, corneal graft rejection, neuroscular glaucoma, liver diseases and Oster Webber syndrome (Osler-Weber Rendu disease).

Diseases associated with neovascularization can be treated according to the present invention. Such diseases include, but are not limited to, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjögren's, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, Scleritis, Steven-Johnson disease, pemphigoid, radial keratotomy, and corneal graph rejection.

Other diseases associated with neovascularization can be treated according to the present invention. Such diseases include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

The present invention may also be used to treat cancerous diseases. Cancerous diseases include, but are not limited to, rhabdomyosarcoma, retinoblastoma, Ewing sarcoma, neuroblastoma, osteosarcoma, acoustic neuromas, neurofibromas, hemangiomas, breast cancer, prostrate cancer, renal cell cancer, brain tumors, ovarian cancer, colon cancer, bladder cancer, cutaneous melanoma, liver cancer, and lung cancer.

Another disease that can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Other diseases that can be treated according to the present invention are hemangiomas, Osler-Weber-Rendu disease, or hereditary hemorrhagic telangiectasia, solid or blood borne tumors and acquired immune deficiency syndrome.

In addition, the invention can be used to treat a variety of post-menopausal symptoms, osteoporosis, cardiovascular disease, Alzheimer's disease, to reduce the incidence of strokes, and as an alternative to prior estrogen replacement therapies. The compounds of the present invention can work by estrogenic and non-estrogenic biochemical pathways.

Also contemplated by the present invention are implants or other devices comprised of the compounds or drugs of Formula I or prodrugs thereof where the drug or prodrug is formulated in a bio-degradable or non-biodegradable polymer for sustained release. Non-biodegradable polymers release the drug in a controlled fashion through physical or mechanical processes without the polymer itself being degraded. Biodegradable polymers are designed to gradually be hydrolyzed or solubilized by natural processes in the body, allowing gradual release of the admixed drug or prodrug. Both bio-degradable and non-biodegradable polymers and the process by which drugs are incorporated into the polymers for controlled release are well known to those skilled in the art. Examples of such polymers can be found in many references such as Brem et al, J. Neurosurg 74: pp. 441-446 (1991). These implants or devices can be implanted in the vicinity where delivery is desired, for example, at the site of a tumor or a stenosis.

Because anything not formed in the body as a natural component may elicit extreme and unexpected responses, such as blood vessel closure due to thrombus formation or spasm, and because damage to blood vessels by the act of insertion of a vascular stent may be extreme and unduly injurious to the blood vessel surface, it is prudent to protect against such events. Restenosis is a re-narrowing or blockage of an artery at the same site where treatment, such as an angioplasty or stent procedure, has already taken place. If restenosis occurs within a stent that has been placed in an artery, it is technically called "in-stent restenosis," the end result being a narrowing in the artery caused by a build-up of substances that may eventually block the flow of blood. The compounds that are part of the present invention are especially useful to coat vascular stents to prevent restenosis. The coating should preferably be a biodegradable or non-biodegradable polymer that allows for a slow release of a compound of the present invention thereby preventing the restenosis event.

Prodrug

The present invention also relates to conjugated prodrugs and uses thereof. More particularly, the invention relates to conjugates of estradiol compounds such as compounds of Formula I, and the use of such conjugates in the prophylaxis or treatment of conditions associated with enhanced angiogenesis or accelerated cell division, such as cancer, and inflammatory conditions such as asthma and rheumatoid arthritis and hyperproliferative skin disorders including psoriasis. The invention also relates to compositions including the prodrugs of the present invention and methods of synthesizing the prodrugs.

In one aspect, the present invention provides a conjugated prodrug of an estradiol compound, preferably compounds of Formula I, conjugated to a biological activity modifying agent.

Alternatively, the conjugated prodrug according to the present invention includes the compounds of Formula I conjugated to a peptide moiety.

The incorporation of an estradiol compound, such as the compounds of Formula I, into a disease-dependently activated pro-drug enables significant improvement of potency and selectivity of this anti-cancer and anti-inflammatory agent.

In addition to the compounds of the present invention, the pharmaceutical composition of this invention may also contain, or be co-administered (simultaneously or sequentially) with, one or more pharmacological agents of value in treating one or more disease conditions referred to hereinabove.

In addition, the compounds of Formula I or prodrug thereof may be incorporated into biodegradable or non-biodegradable polymers allowing for sustained release, the polymers being implanted in the vicinity of where delivery is desired, for example, at the site of a tumor. Polymers and their use are described in detail in Brem et al., J. Neurosurg 74:441-446 (1991).

A person skilled in the art will be able by reference to standard texts, such as Remington's Pharmaceutical Sciences 17th edition, to determine how the formulations are to be made and how these may be administered.

In a further aspect of the present invention there is provided use of compounds of Formula I or prodrugs thereof according to the present invention for the preparation of a medicament for the prophylaxis or treatment of conditions associated with angiogenesis or accelerated cell division or inflammation.

In a further aspect of the present invention there is provided a pharmaceutical composition comprising compounds of Formula I or prodrugs thereof according to the present invention, together with a pharmaceutically acceptable carrier, diluent or excipient.

The pharmaceutical composition may be used for the prophylaxis or treatment of conditions associated with angiogenesis or accelerated cell division or inflammation.

In a still further aspect of the present invention there is provided a method of prophylaxis or treatment of a condition associated with angiogenesis or accelerated or increased amounts of cell division hypertrophic growth or inflammation, said method including administering to a patient in need of such prophylaxis or treatment an effective amount of compounds of Formula I or prodrugs thereof according to the present invention, as described above.

It should be understood that prophylaxis or treatment of said condition includes amelioration of said condition.

By "an effective amount" is meant a therapeutically or prophylactically effective amount. Such amounts can be readily determined by an appropriately skilled person, taking into account the condition to be treated, the route of administration and other relevant factors. Such a person will readily be able to determine a suitable dose, mode and frequency of administration.

Pharmaceutically acceptable salts of the compound of the formula may be prepared in any conventional manner for example from the free base and acid. In vivo hydrolysable esters, amides and carbamates may be prepared in any conventional manner.

Improved Estradiol Derivative Synthesis

Known compounds that are used in accordance with the invention and precursors to novel compounds according to the invention can be purchased, e.g., from Sigma Chemical Co., St. Louis, Steraloids or Research Plus. Other compounds according to the invention can be synthesized according to known methods from publicly available precursors.

The chemical synthesis of estradiol has been described (Eder, V. et al., Ber 109, 2948 (1976); Oppolzer, D. A. and Roberts, D A. Helv. Chim. Acta. 63, 1703, (1980)). The synthetic pathways used to prepare some of the derivatives of the present invention are based on modified published literature procedures for estradiol derivatives (Trembley et al., Bioorganic & Med. Chem. 1995 3, 505-523; Fevig et al., J. Org. Chem., 1987 52, 247-251; Gonzalez et al., Steroids 1982, 40, 171-187; Trembley et al., Synthetic Communications 1995, 25, 2483-2495; Newkome et al., J. Org. Chem. 1966, 31, 677-681; Corey et al Tetrahedron Lett 1976, 3-6; Corey et al., Tetrahedron Lett, 1976, 3667-3668) and German Patent No. 2757157 (1977).

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into polymers allowing for sustained release, the polymers being implanted in the vicinity of where delivery is desired, for example, at the site of a tumor or within or near the eye. The dosage of the composition will depend on the condition being treated, the particular derivative used, and other clinical factors such as weight and condition of the patient and the route of administration of the compound. However, for oral administration to humans, a dosage of 0.01 to 100 mg/kg/day, especially 0.01-20 mg/kg/day, is generally preferred.

The formulations include those suitable for oral, rectal, nasal, inhalation, topical (including dermal, transdermal, buccal and sublingual), vaginal or parenteral (including subcutaneous, intramuscular, intravenous, intradermal, intraocular, intratracheal, and epidural) and inhalation administration. The formulations may conveniently be presented in unit dosage form and may be prepared by conventional pharmaceutical techniques. Such techniques include the step of bringing into association the active ingredient and a pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kinds previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

The present invention includes compositions and methods for treating mammalian disease characterized by pathogenic angiogenesis by administering compounds of Formula I. The 2-methoxyestradiol, and derivatives thereof, are modified at the 3 and 17 positions. Combinations which are physically impossible are not contemplated by this invention, such as a carbon atom containing 5 bonds.

100% pure isomers are contemplated by this invention, however a stereochemical isomer labeled as α or β may be a mixture of both in any ratio, where it is chemically possible by one skilled in the art. Also contemplated by this invention are both classical and non-classical bioisosteric atom and substituent replacements, such as are described by Patani and Lavoie (Bio-isosterism: a rational approach in drug design Chem. Rev. (1996) p. 3147-3176) and are well known to one skilled in the art. Such bioisosteric replacements include, for example, substitution of =S or =NH for =O.

The synthetic routes for this series of analogs are summarized in Schemes 1-7. Schemes 1 and 2 present the preparation of the singly and doubly substituted templates that are required as precursors for the triply substituted analogs. Schemes 3-7 present on the modification of position 3 of the templates derived from Schemes 1 and 2. These synthetic routes present one potential way to prepare this series of analogs, and other synthetic routes (including modifying the order of synthetic steps or reagents) are possible to someone skilled in the art.

In Scheme 1, the 2-methoxy, 2-ethoxy or 2-propynyl derivatives, which are either commercially available or can be readily prepared by literature methods (Wang et al, Synthetic Comm 1998, 28, 4431, Cushman et al J. Med. Chem. 1995, 38, 2041, Cushman et al J. Med. Chem. 1997, 40, 2323, Cushman et al J. Med. Chem. 2002, 45, 4748), are oxidized using the Oppenauer oxidation. The resulting ketone can be deoxygenated using the Wolf-Kishner reduction (Shapiro R, J. et al J. Org. Chem. 1964, 86, 2825-2832.) or olefinated (Schow et al J. Org. Chem. 1979, 44, 22. Krubner et al J. Org. Chem. 1968, 33, 1715.) using the Wittig reaction. Both the 17-methylene and 17-ethylene estrane analogs can be reduced to the alkane using catalytic reduction.

In specific cases, the nature of protecting groups or the order of reactions may have to be altered to reach the desired products. These changes to the general synthetic schemes would be well understood to one skilled in the art. For instance, in the case where the desired 2 functionality is a propyne and the desired 17-functionality is an alkyl group, catalytic hydrogenation could not be carried out on the 17-olefin since the 2-alkyne would also be reduced. Scheme 2 presents a synthetic route to prepare analog 18. In this example, the 17 methyl is introduced as in Scheme 1 starting with estrone, and subsequently the 2-propyne is incorporated using a literature method (Cushman et al J. Med. Chem. 2002, 45, 4748).

Schemes 3-7 feature the further modification of the templates generated in Schemes 1 and 2. In Scheme 3, templates 4, 5 or 6 can be converted to the 3-sulfamate derivative (19, 20 or 21) with sulfamoyl chloride and either sodium hydride (Howarth et al J. Med. Chem. 1994, 37, 219) or 2,6-di-tert-butyl-4-methylpyridine (Coibanu et al J. Med. Chem. 1999, 42, 2280). To prepare analogs 22-24, triflic anhydride was added to a solution of 4, 5 or 6 in dichloromethane and pyridine at 0° C. using Echavarren's procedure (Echvarren et al J. Am. Chem. 1987, 109, 5478). The triflate is a versatile synthetic intermediate and was used to incorporate a wide range of functional groups at position 3. One utility of the triflate is its conversion to the vinyl analog via palladium catalyized substitution with a vinyl functionality (analogs 25-27) (Shi et al J. Med Chem. 2002, 124, 6921). The carboxylic acid derivatives (28-30) were also prepared by palladium catalysis as well (Shi et al Chem. & Biol. 2001, 8, 501). The carboxylic acid could also be converted to the corresponding amide using thionyl chloride and ammonia gas (Tomas de, Paulis, et. at. J. Med. Chem. 1986, 29, 61). The triflate could be converted directly to a carboxamide using a procedure described by Morera (Tetrahedron Letters, 1998, 39, 2835-2838). Alternatively, the triflate could be converted to an amine via palladium catalyzed substitution of the triflate with benzophenone imine, subsequent hydrolysis yielded the corresponding amine (analogs 34-36) (Wolfe et al Tetrahedron Lett 1997, 38, 6367). The 3-amine could be converted to 3-fluoro analogs using the diazonium salt intermediate (Morrow J. Med. Chem. 1966, 9, 249). Additionally, ketones 34-36 can be reduced to the corresponding alcohols 37-39 with lithium aluminum hydride at −78° C. then converted to amides 43-45 with trimethylacetic formyl anhydride (Vleitstra et al Recueil 1982, 101, 460). Schemes 4-7 use analogous chemistry to prepare other triply modified steroid analogs.

Compounds according to the present invention may be prepared using the reaction schemes shown below:

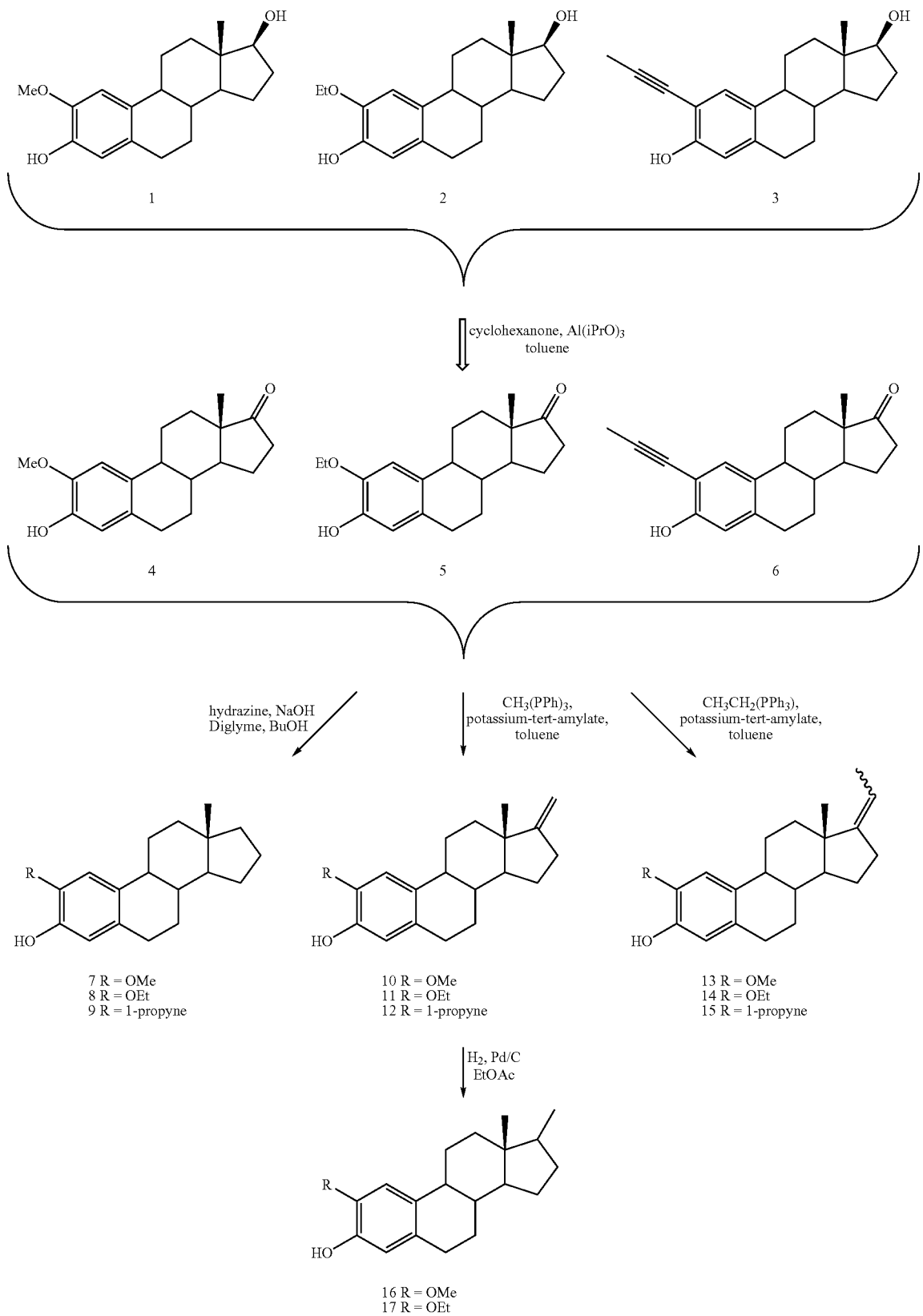

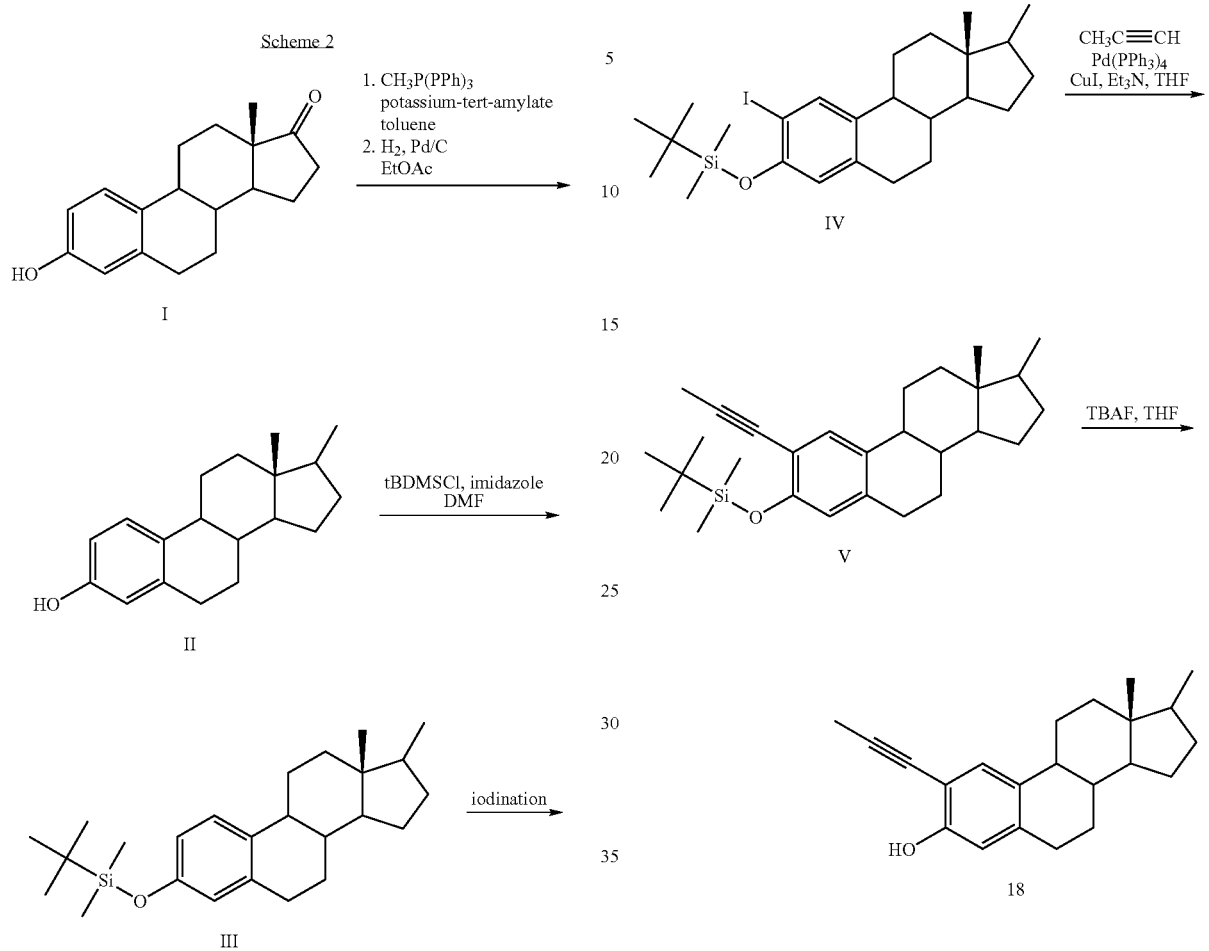
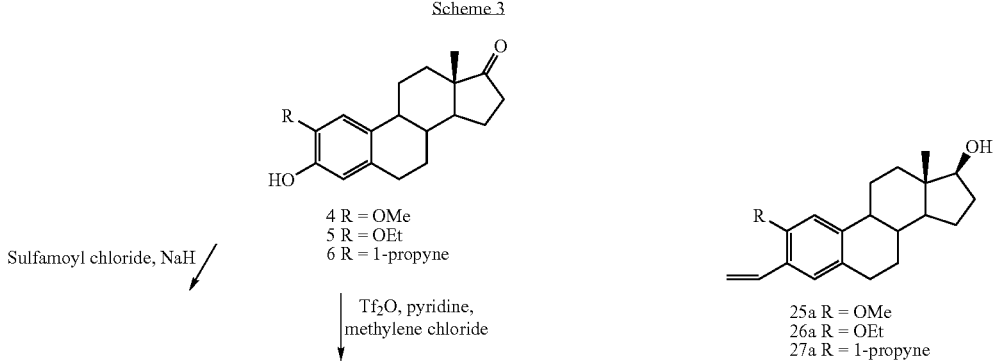

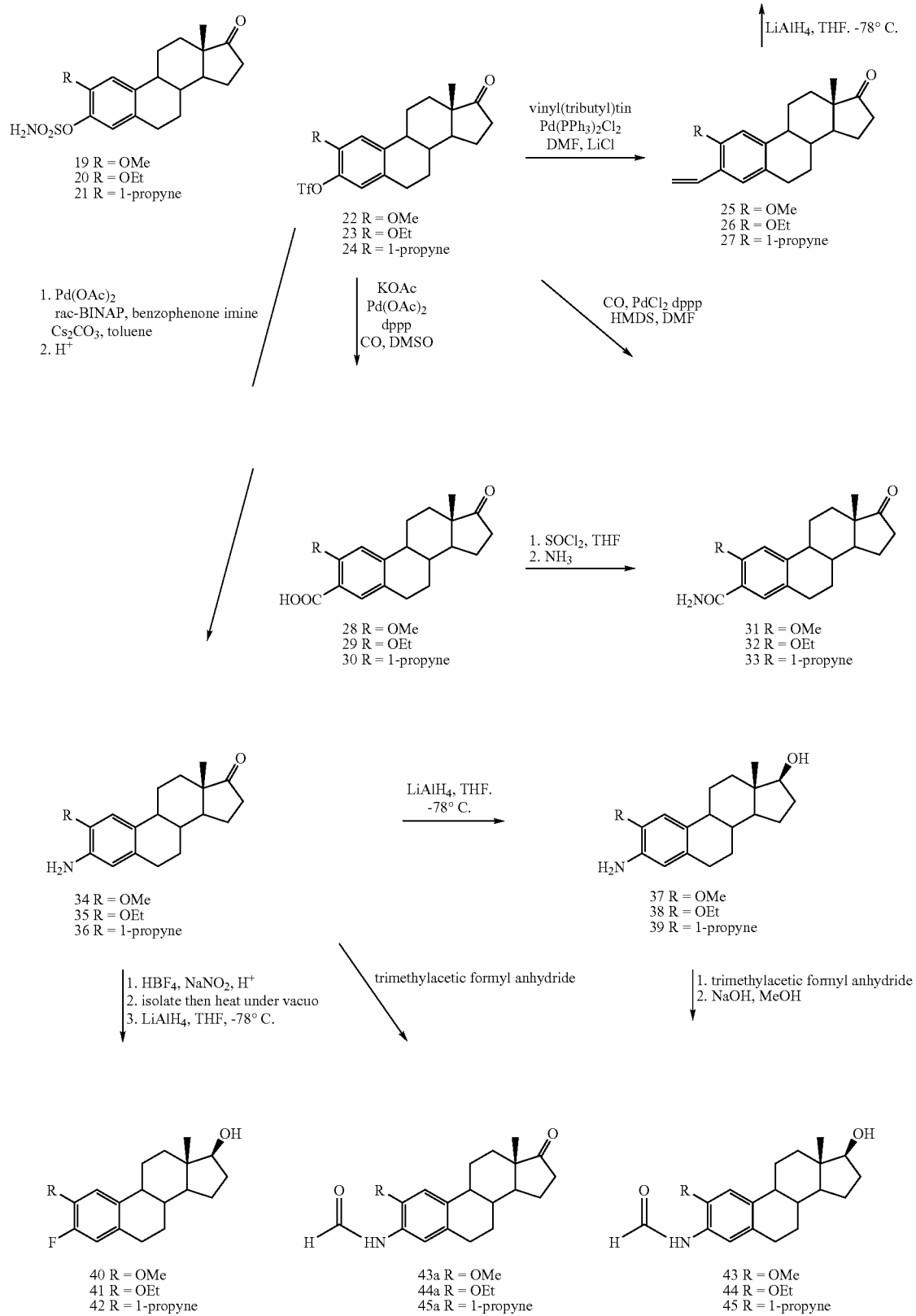

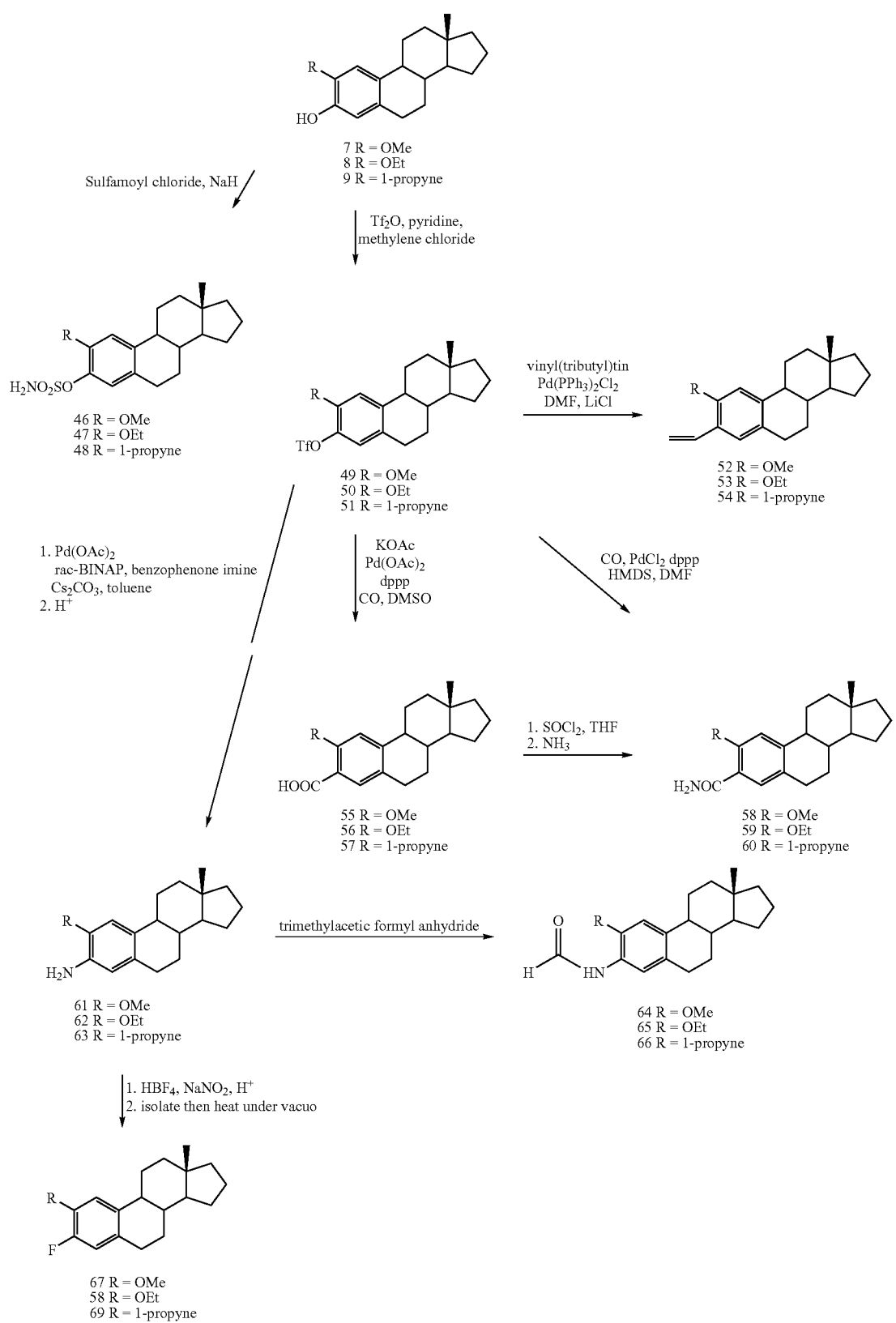

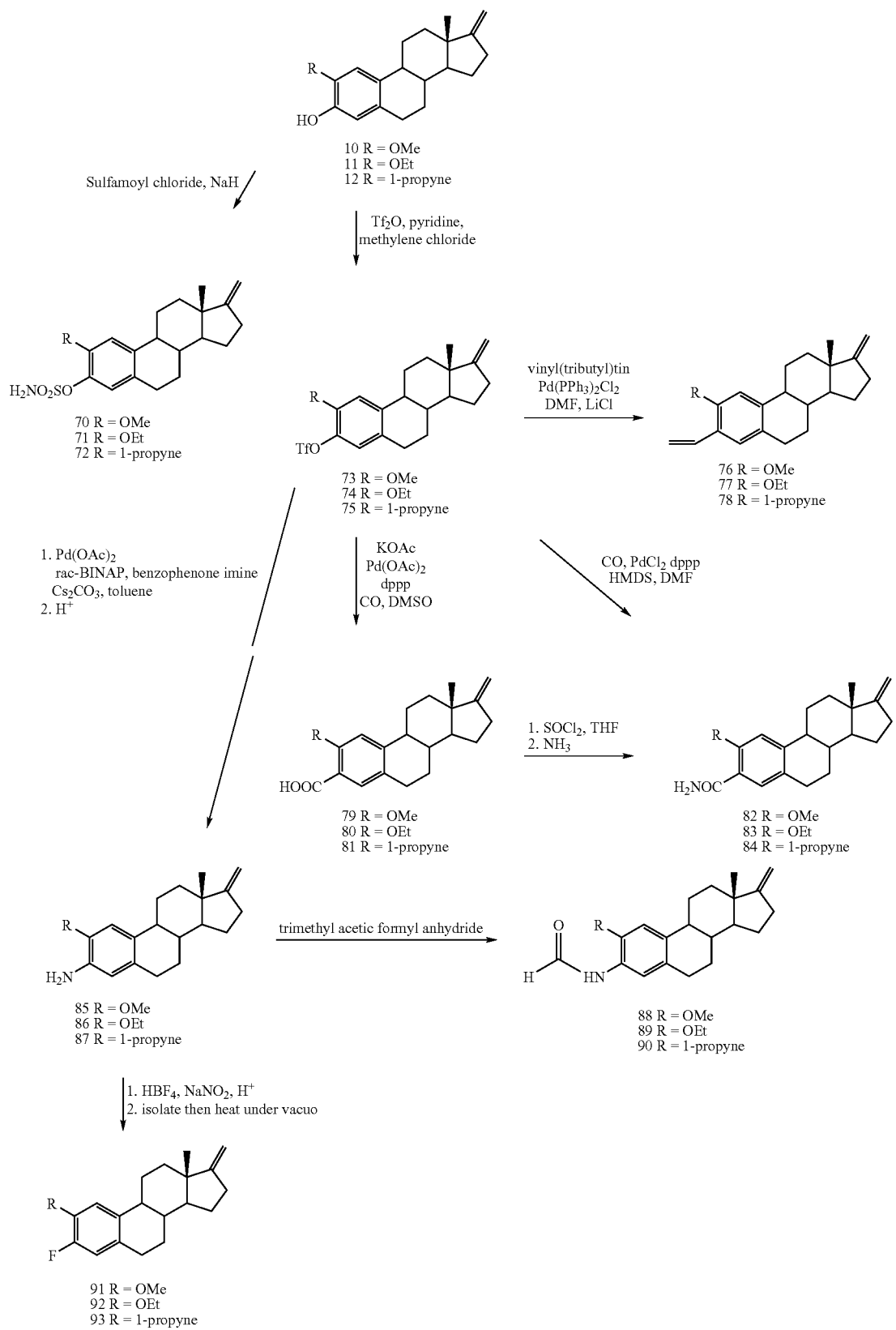

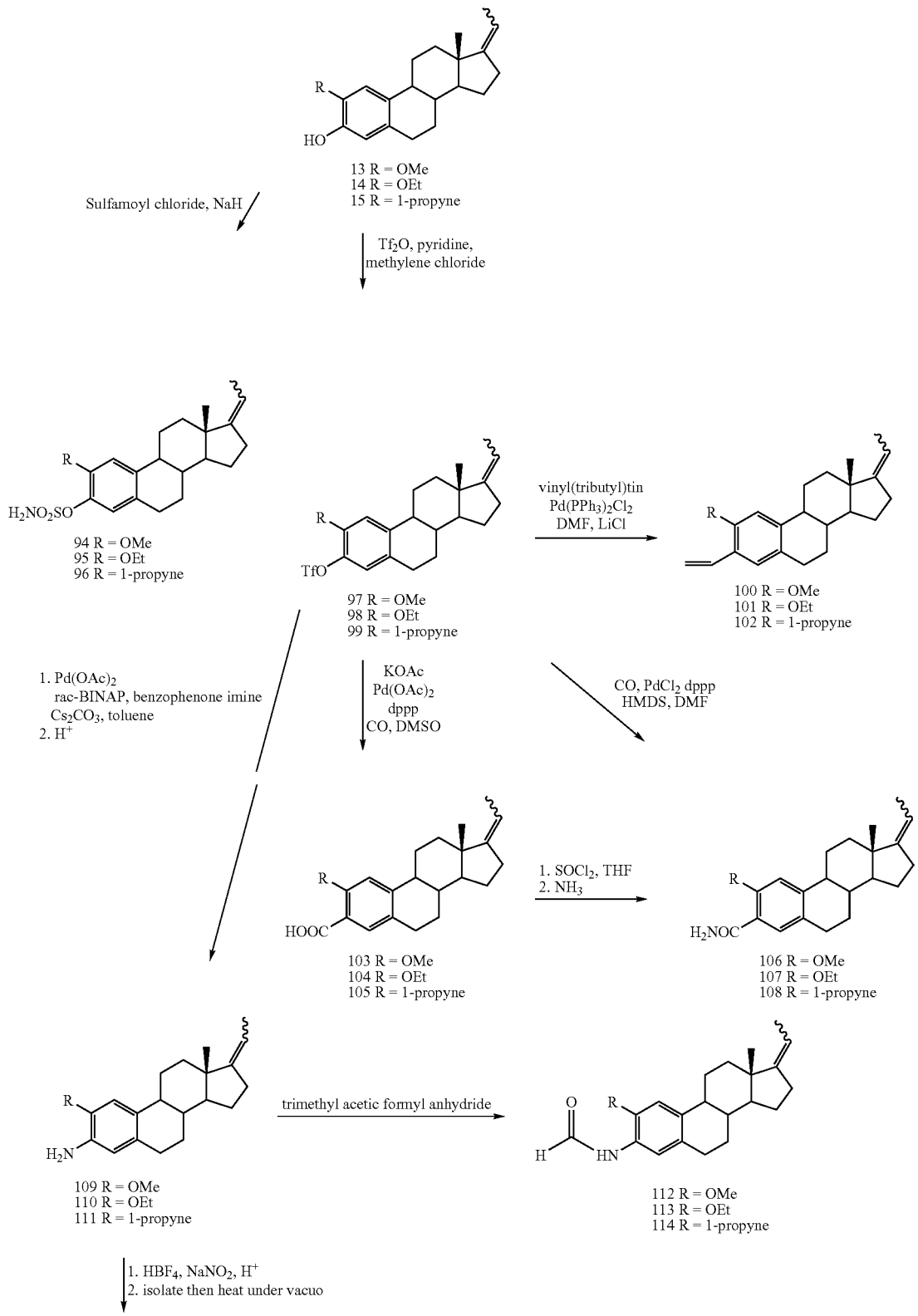

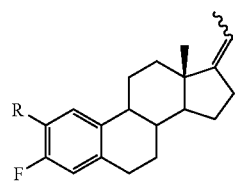
115 R = OMe
116 R = OEt
117 R = 1-propyne
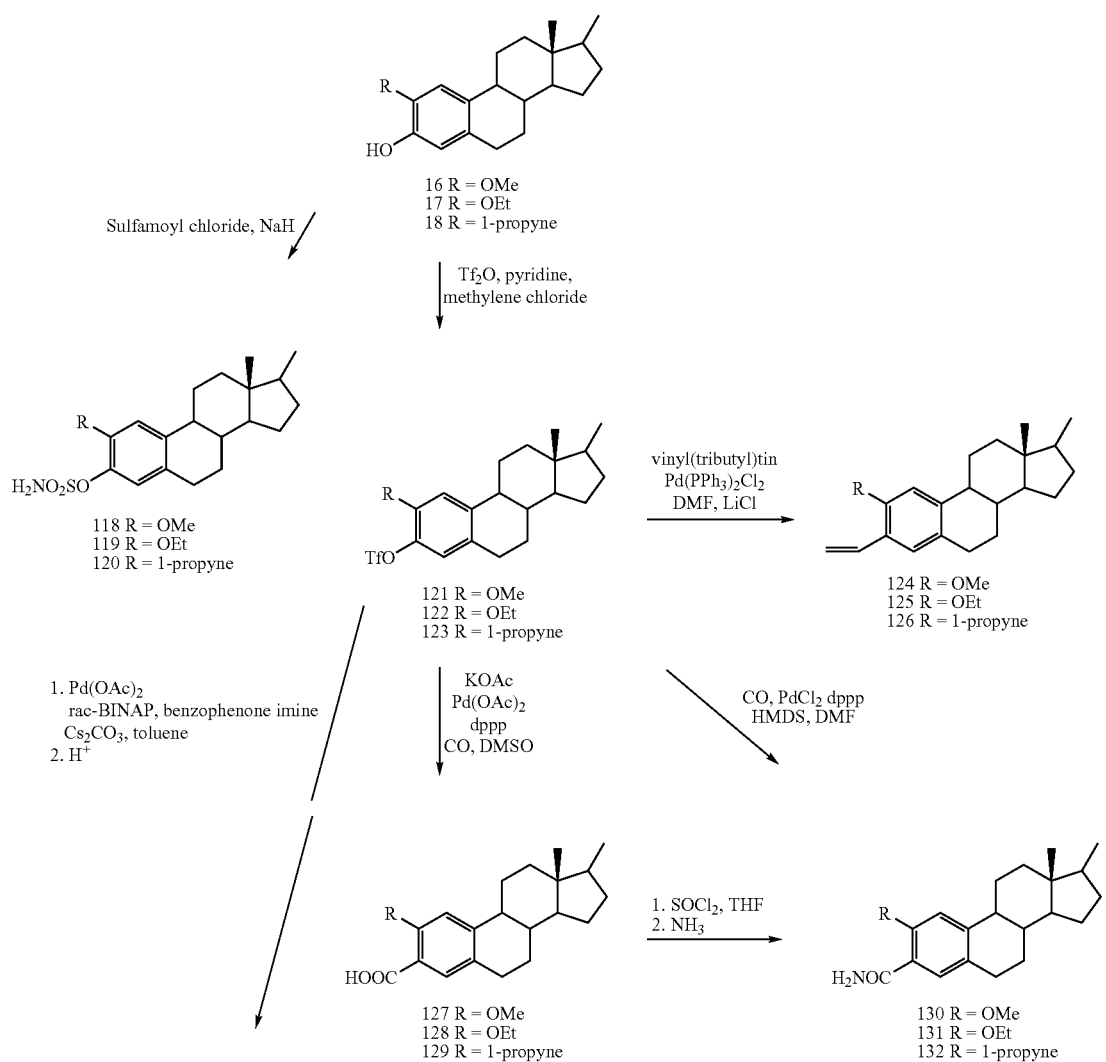

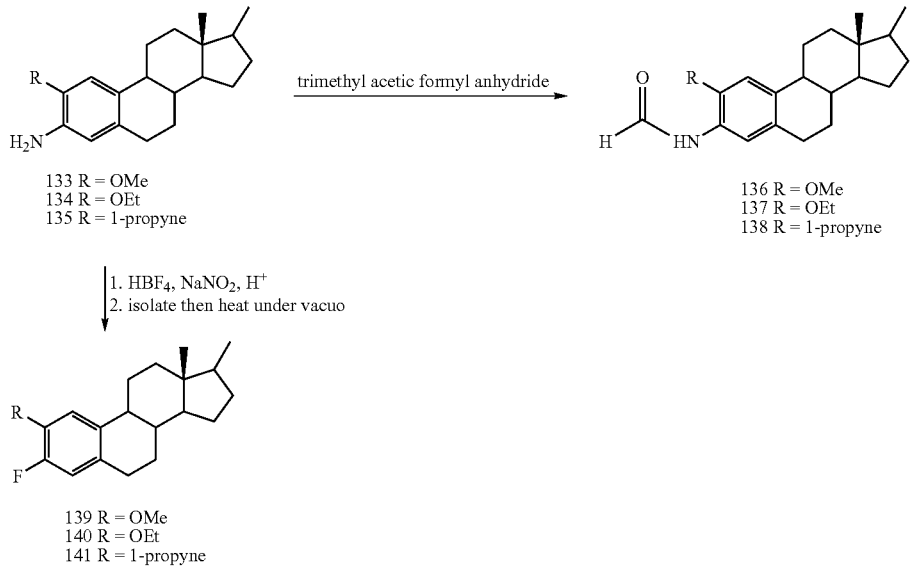

EXPERIMENTAL DATA

The following Examples refer to compounds of the following general Formula I:

(I)

wherein $R_a$ is selected from —OCH$_3$, —OCH$_2$CH$_3$ or —CCCH$_3$; Z' is selected from >C—F, >C—NH$_2$, >CCONH$_2$, >C—NHCOH, >C—OSO$_2$NH$_2$ or >C—CHCH$_2$, and Z" is selected from >C(H$_2$), >C(H)—CH$_3$, >C=CH$_2$, >C=CHCH$_3$ or >C=O; provided that when Z' is >C—OSO$_2$NH$_2$ and Z" is >C(H$_2$) or >C=O, $R_a$ is neither —OCH$_3$ nor —OCH$_2$CH$_3$. Preferred species from the foregoing genus that are useful in the present invention include, but are not limited to, the compounds shown in Table I.

TABLE I

3-Amines

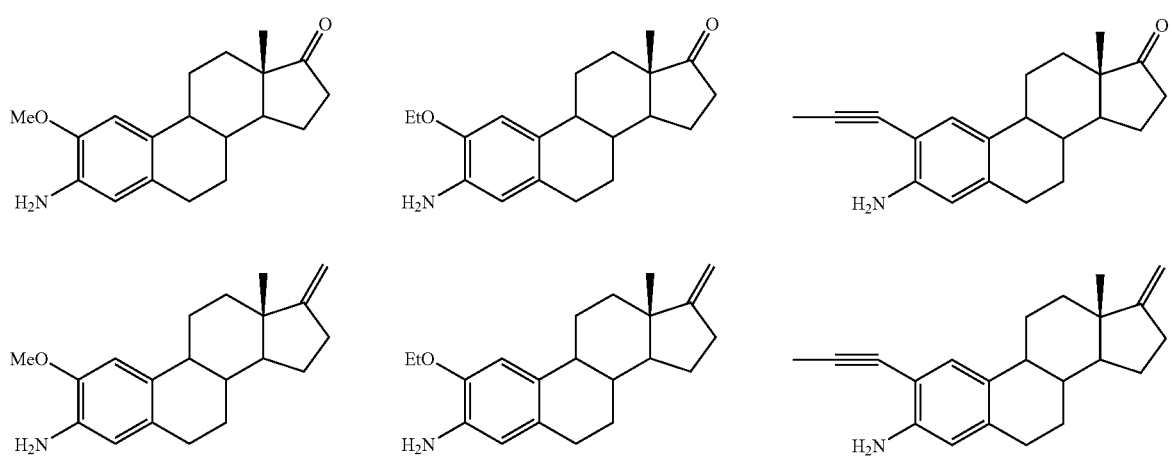

TABLE I-continued
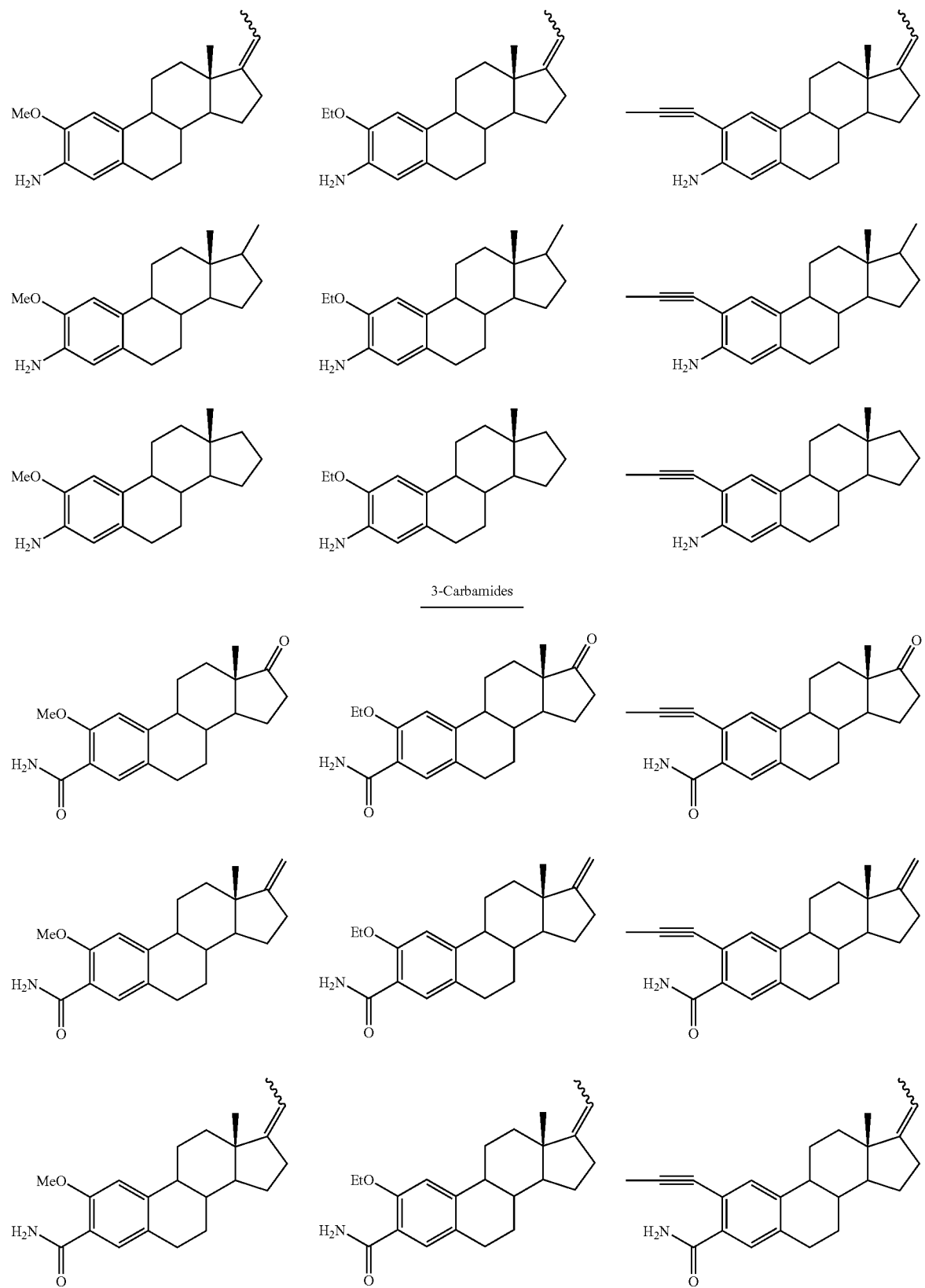
3-Carbamides

TABLE I-continued
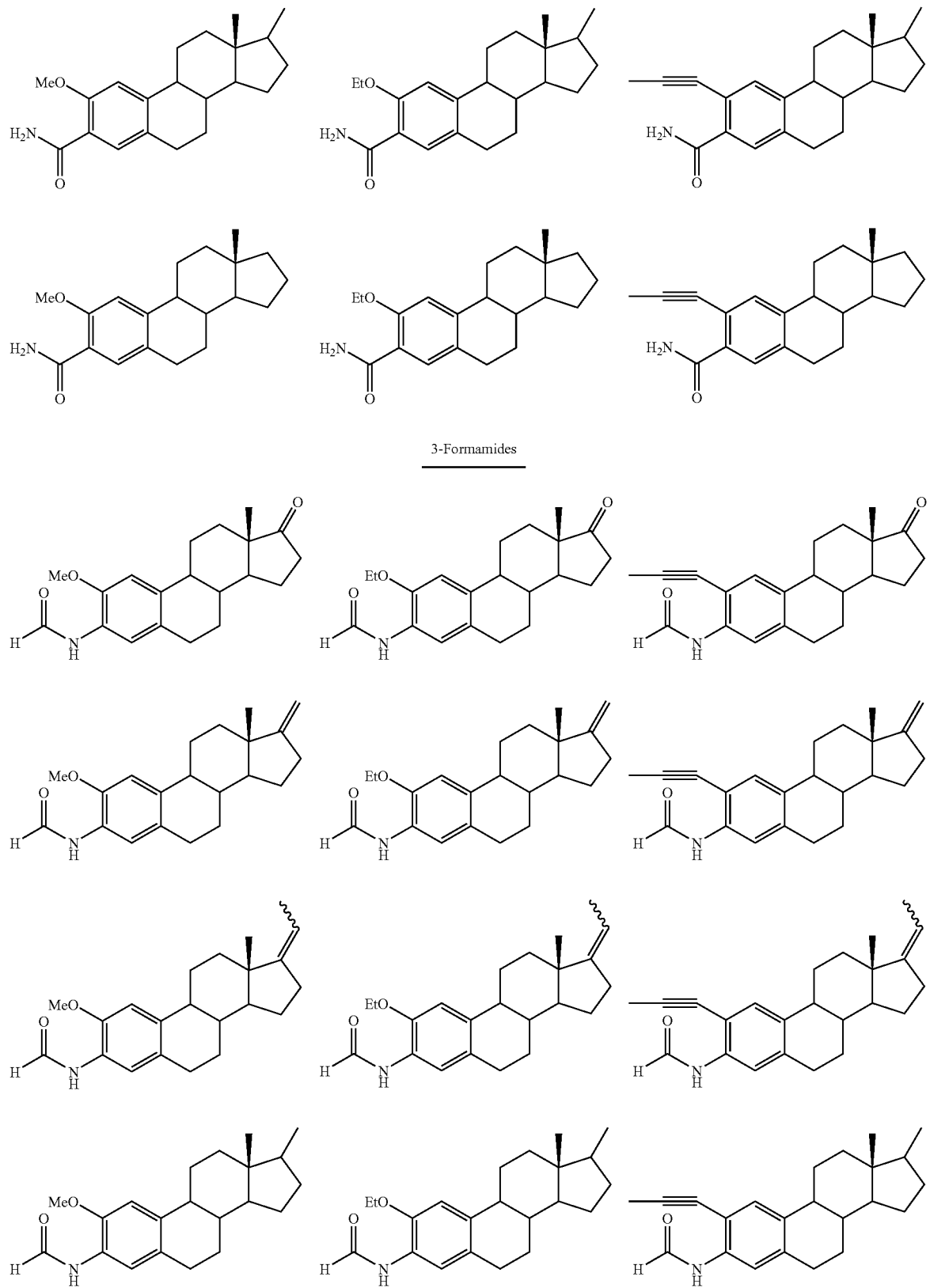
3-Formamides

TABLE I-continued
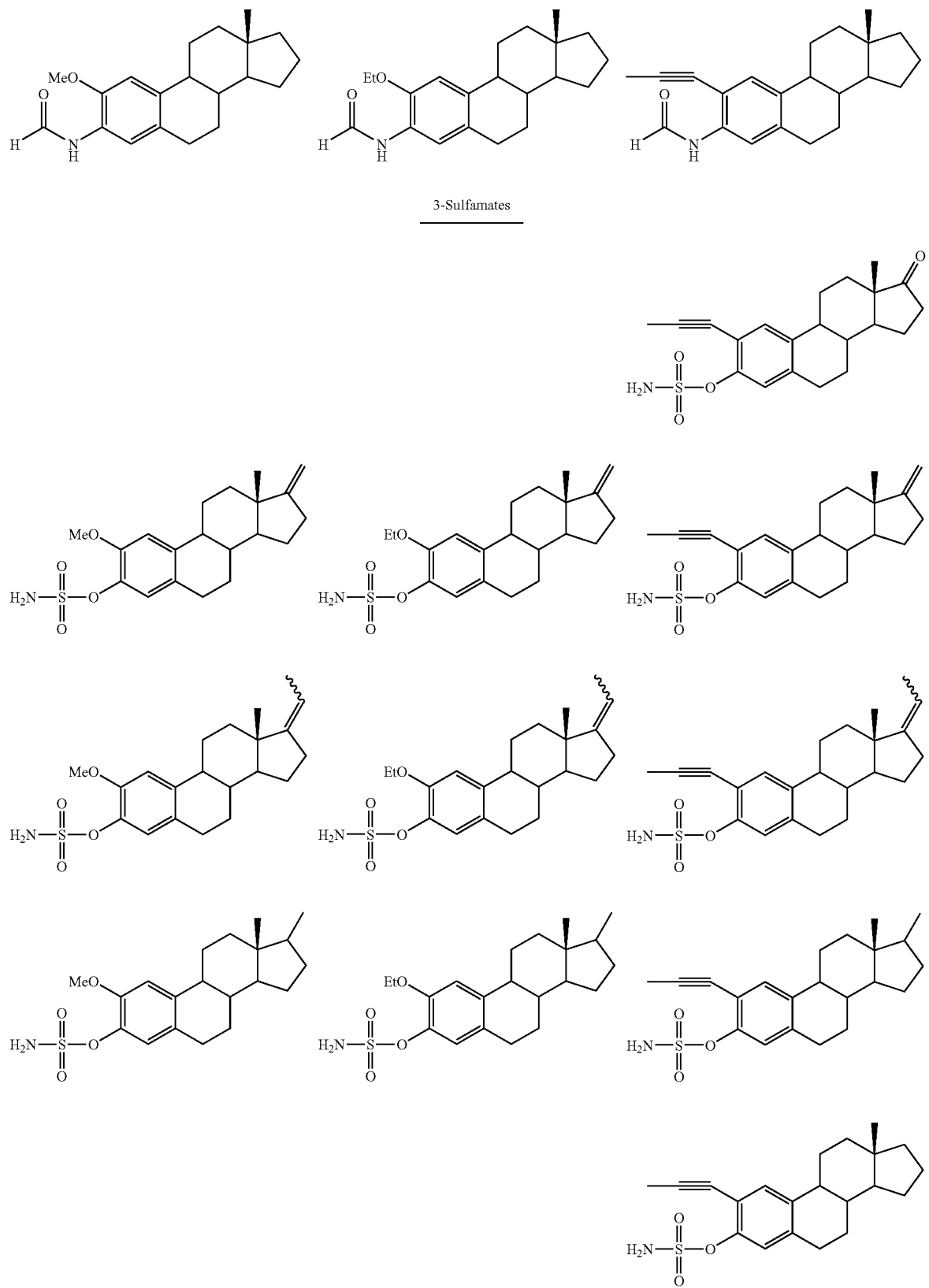
3-Sulfamates

TABLE I-continued
3-Vinyls
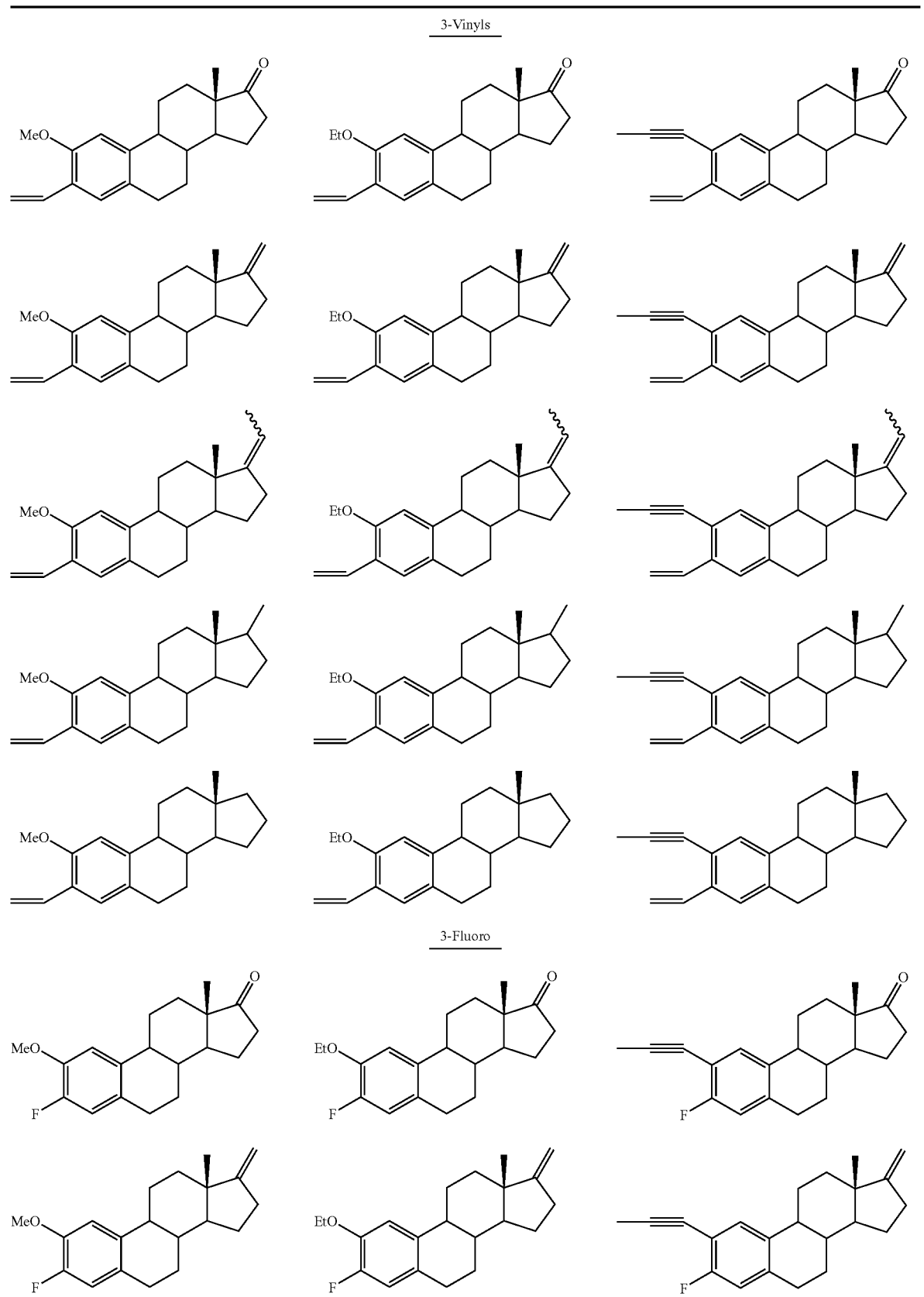
3-Fluoro

TABLE I-continued
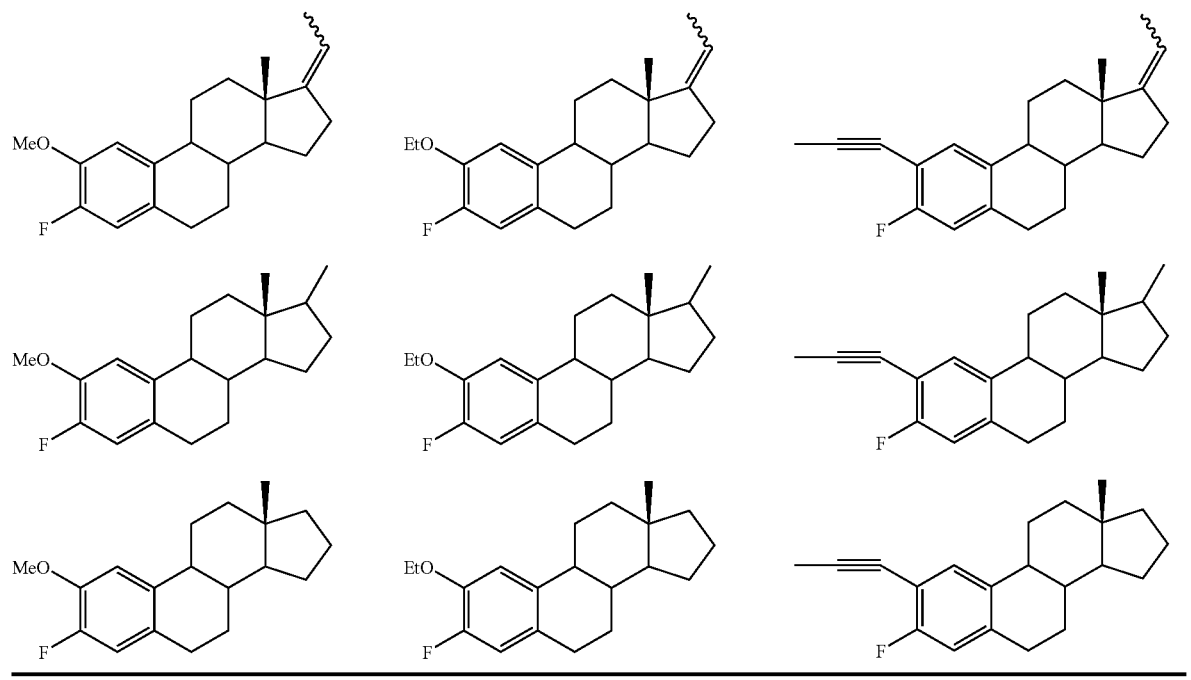
Each of the foregoing compounds from Table I are found to have anti-mitotic, anti-angiogenic and/or anti-tumor properties.
In an alternate disclosed embodiment of the present invention, preferred species from the foregoing genus that are useful in the present invention include, but are not limited to, the compounds shown in Table II.
TABLE II
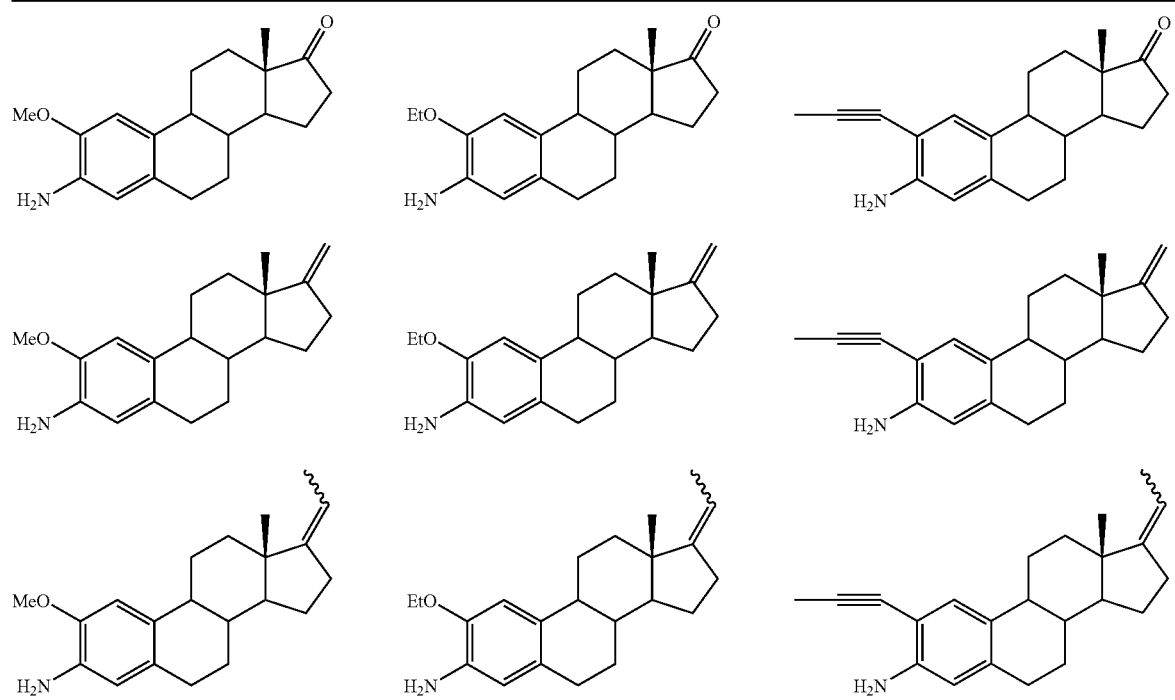

TABLE II-continued
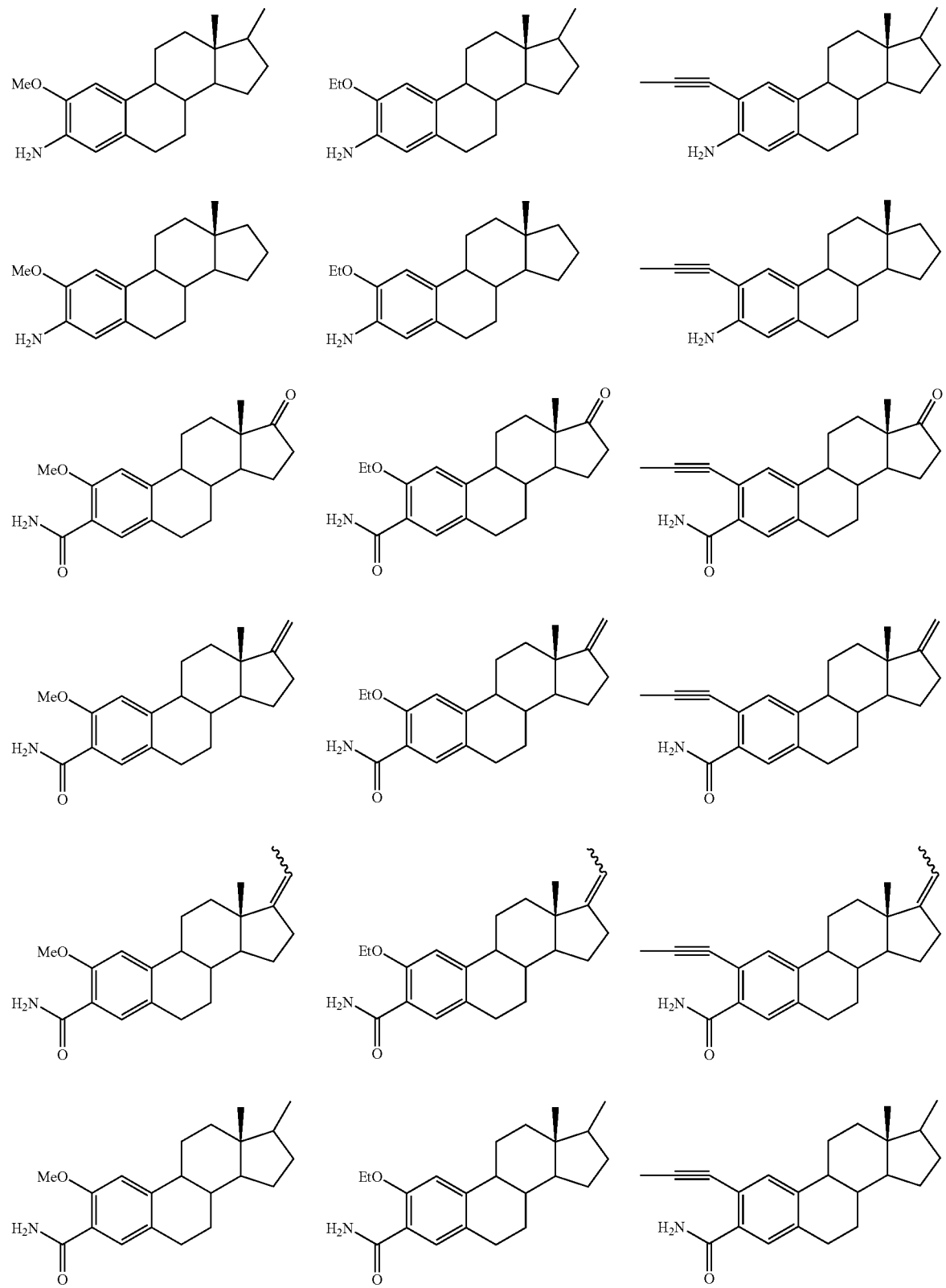

TABLE II-continued
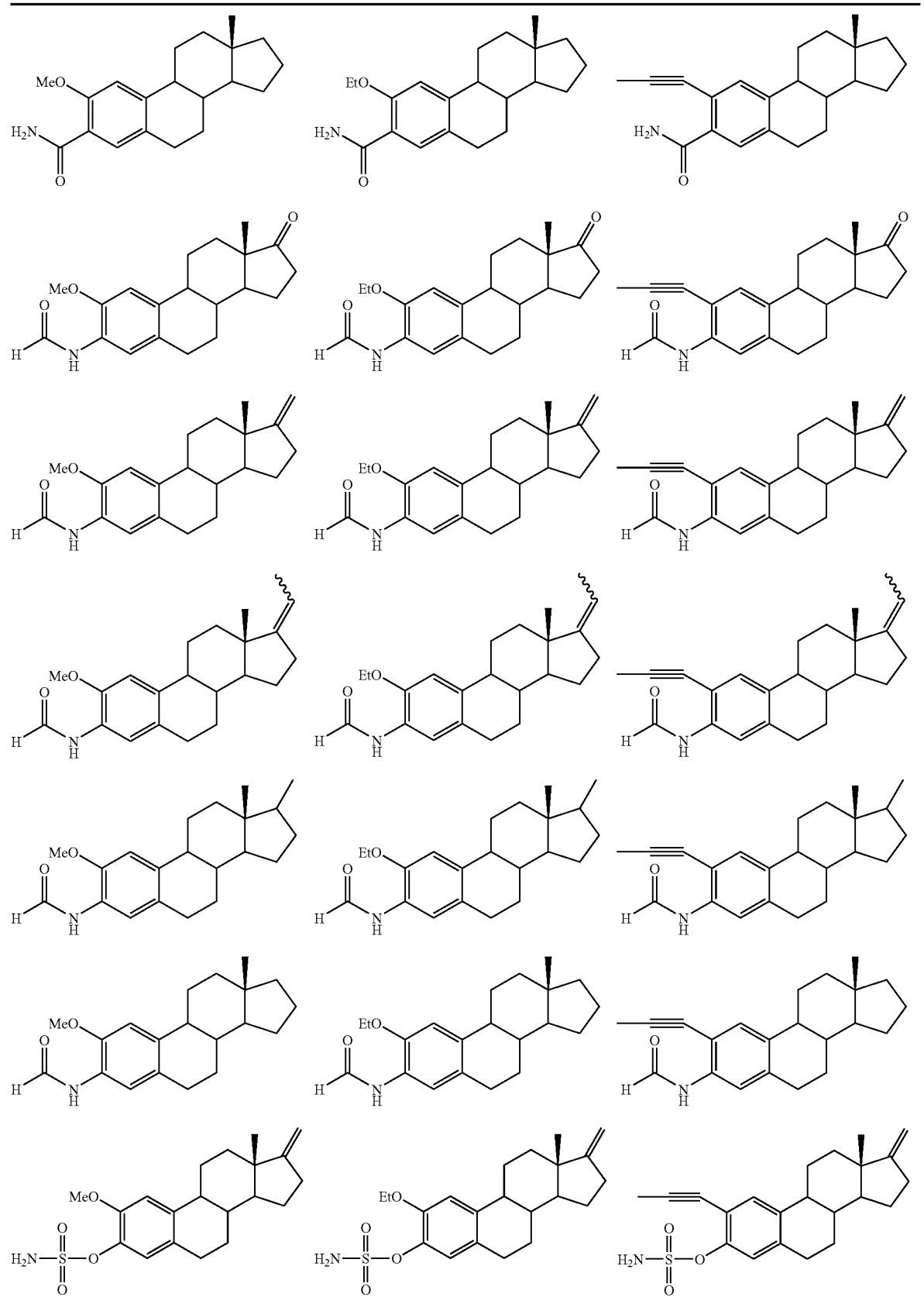

TABLE II-continued
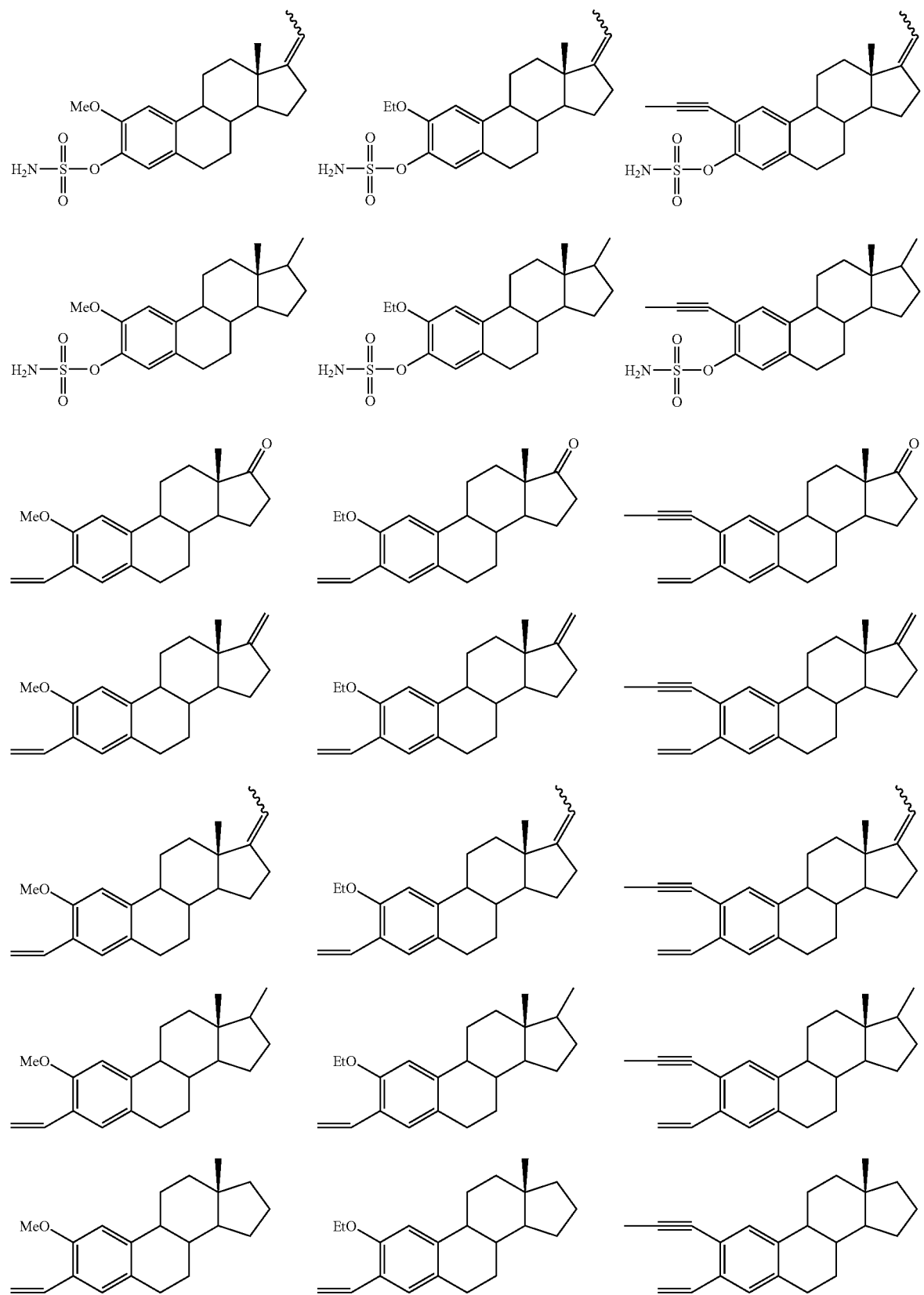

TABLE II-continued
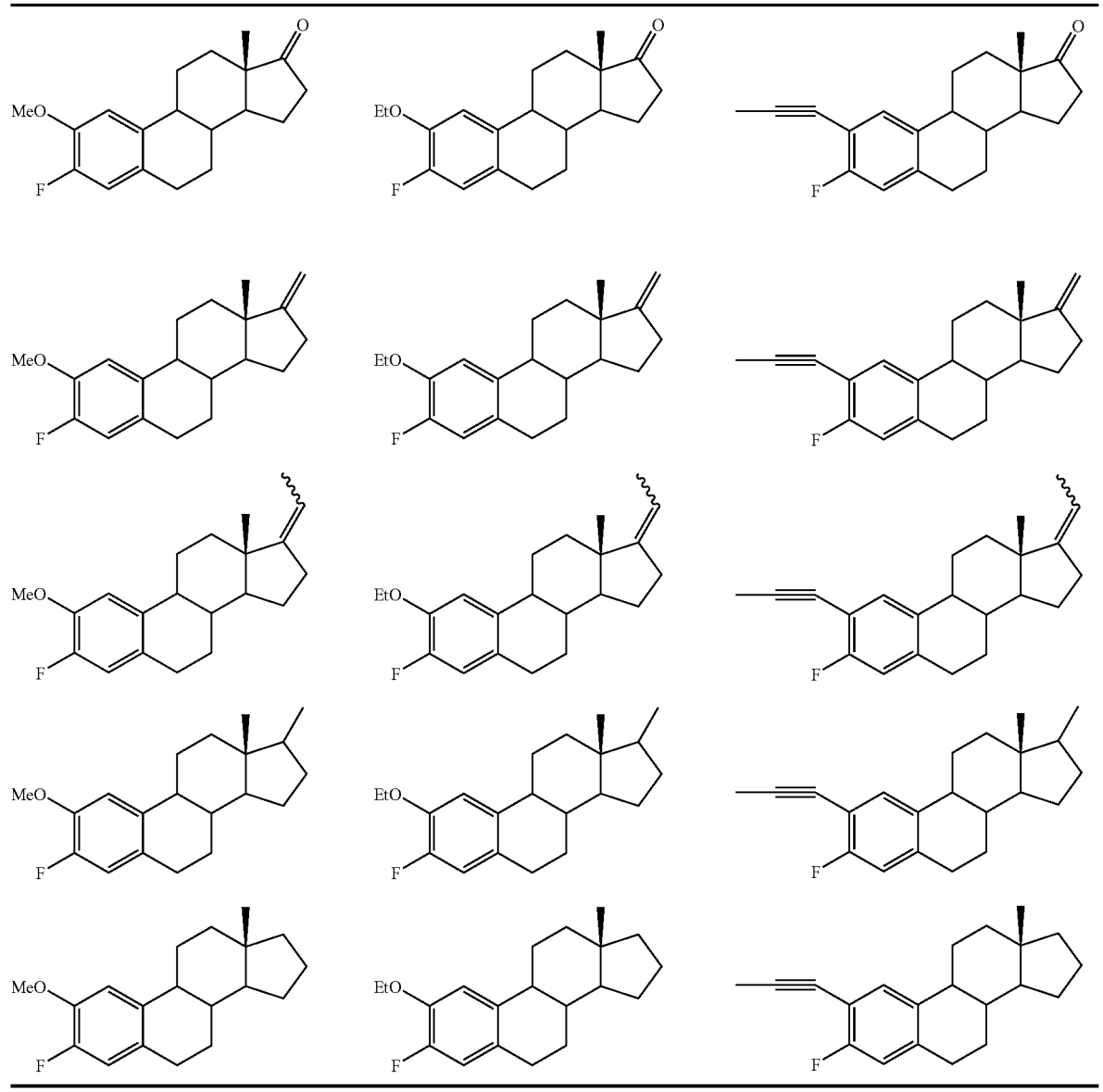
In another alternate disclosed embodiment of the present invention, preferred species from the foregoing genus that are useful in the present invention include, but are not limited to, the compounds shown in Table III.
TABLE III
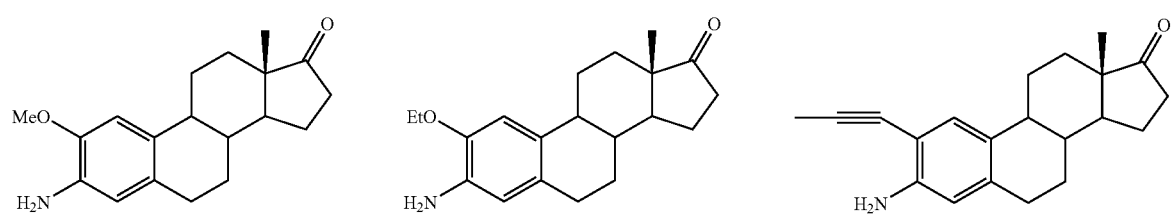

TABLE III-continued
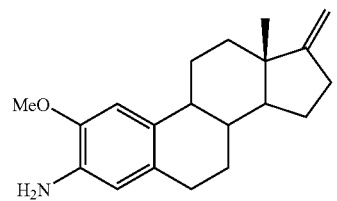 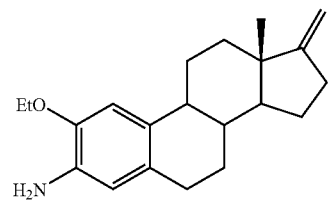 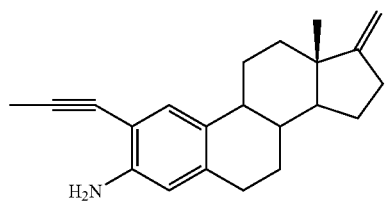
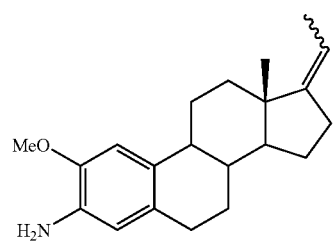 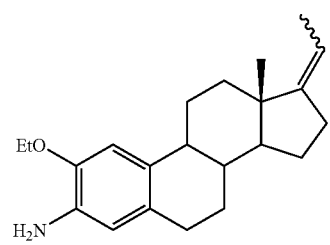 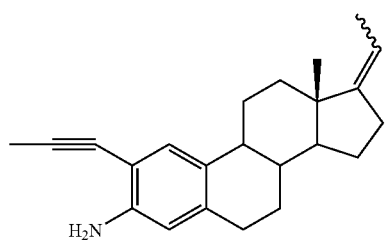
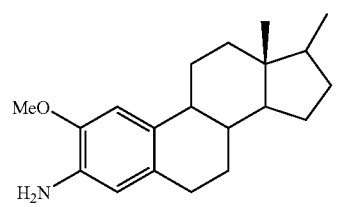 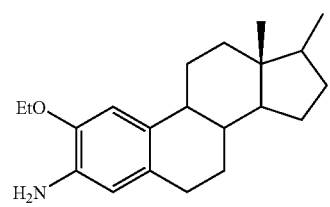 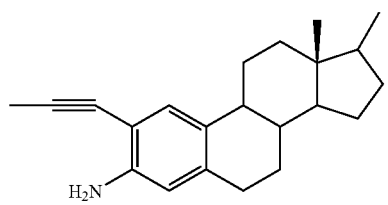
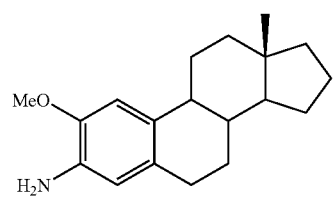 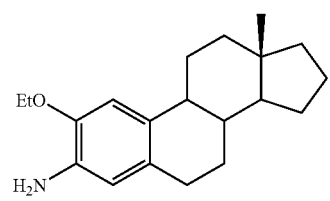 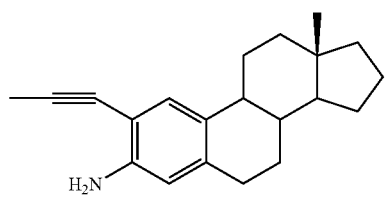
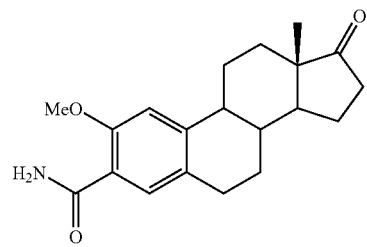 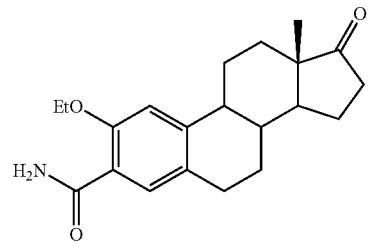 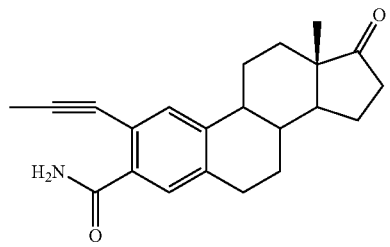
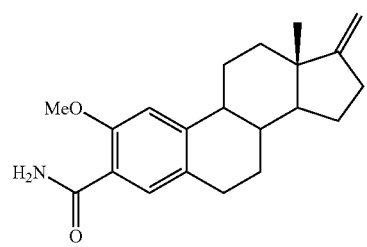 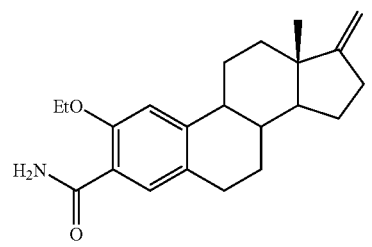 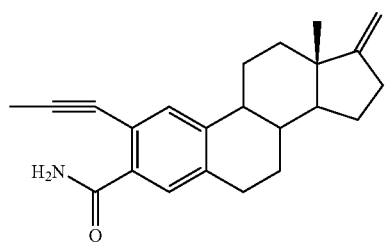

TABLE III-continued
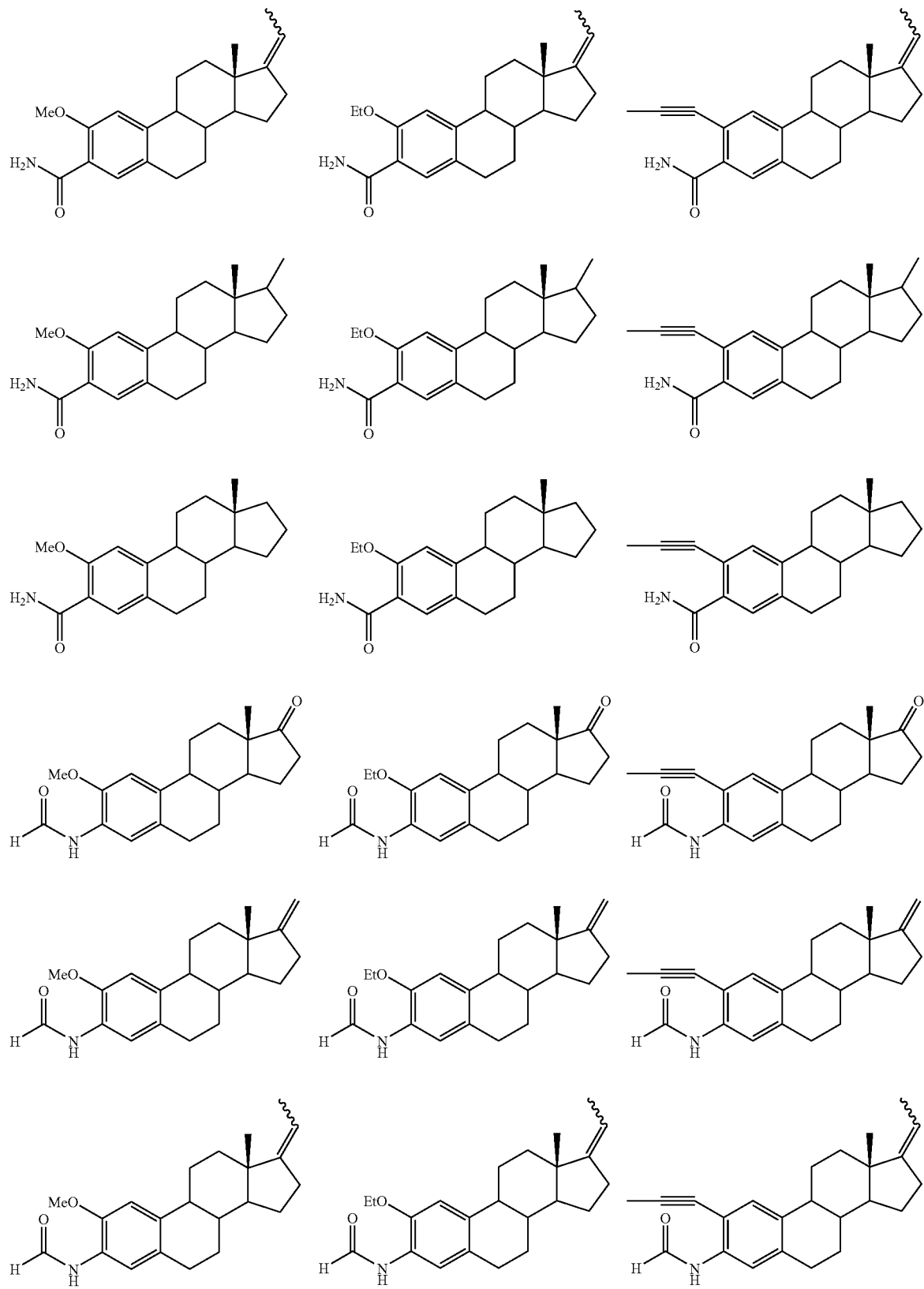

TABLE III-continued

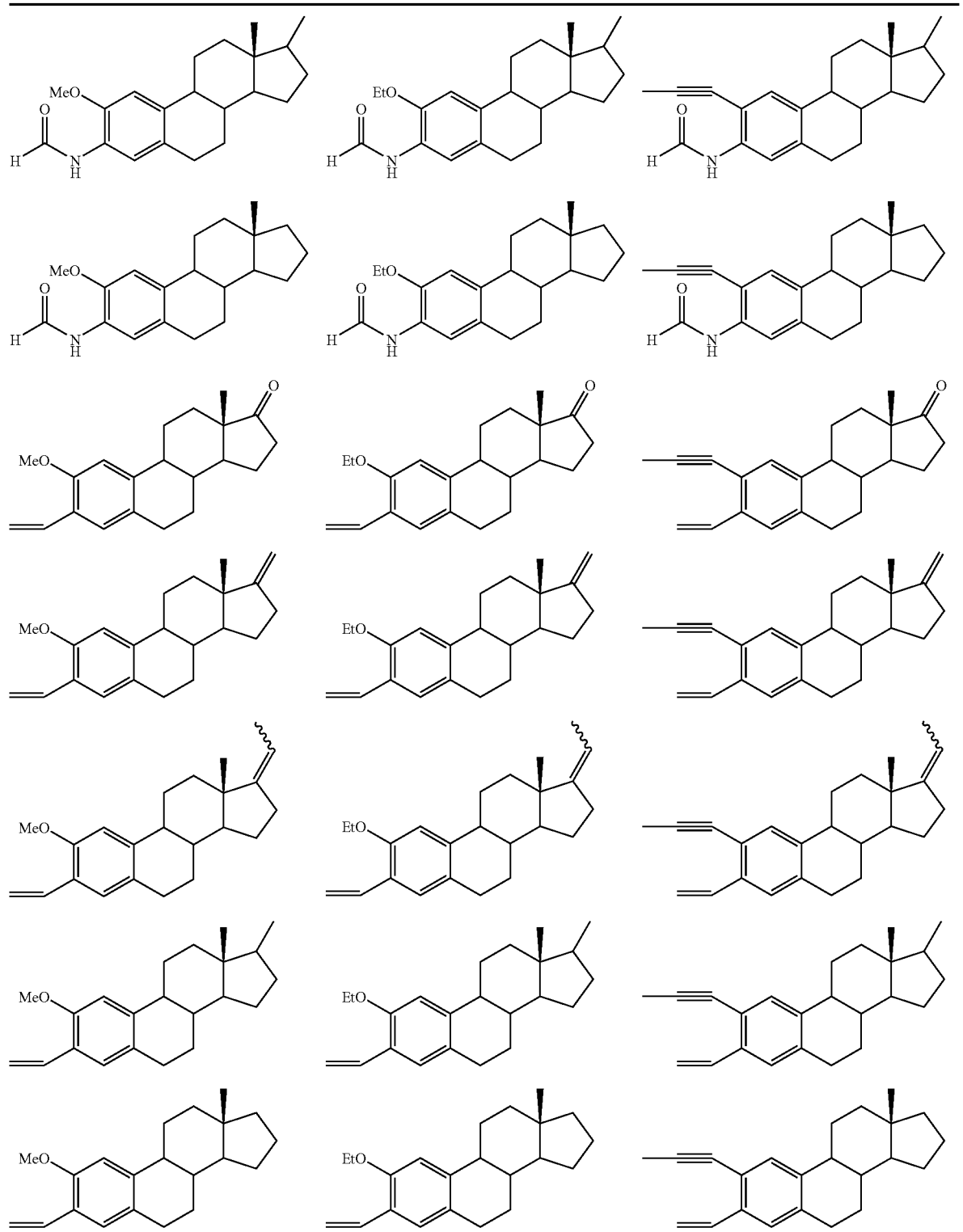

Example 1

The procedures described below are for specific compounds. However, these reactions can be applied to all examples in this patent by one skilled in the art. References to compound #s below correspond to the numbers assigned to the compounds shown in the synthesis Schemes 1-7 above.

Representative oxidation of estradiol analogs to estrone analogs: 2-ethoxyestra-1,3,5(10)-trien-3-ol-17-one (Compound #5): 2-Ethoxyestra-1,3,5(10)-trien-3,17-diol (#2, 1.88 g, 5.67 mmol) was placed in a 250 mL round bottom flask that was equipped with a 25 mL Dean-Stark trap and a reflux condenser. The entire apparatus had been flame dried under an argon atmosphere. Toluene (50 mL) was added to dissolve the starting material. Aluminum isopropoxide (5.7 g, 28.4 mmol) and cyclohexanone (23.5 mL, 2.26.8 mmol) were added and the entire reaction mixture was heated at reflux (145-150° C.) for 20 h. Saturated aqueous sodium bicarbonate solution (100 mL) was added after the reaction mixture was allowed to cool to room temperature. The organic material was extracted with dichloromethane (3×150 mL). The aqueous emulsion was acidified with 3 N HCl (~20 mL) until the emulsion separated and again, the aqueous layer was extracted with ethyl acetate (2×75 mL). The combined organic extracts were dried over magnesium sulfate and condensed in vacuo. The crude product was purified via flash chromatography (silica gel, hexanes ethyl acetate 8:1 by volume) to produce #5 as a white solid (1.7 g, 94%). $^1$H NMR (300 MHz, CDCl$_3$) δ 6.78 (s, 1H), 6.66 (s, 1H), 5.49 (s, 1H), 4.07 (dq, J=6.9 and 1.6 Hz, 2H), 2.83 (m, 2H), 2.52 (m, 2H), 2.36-1.37 (m, 11H), 1.42 (t, J=7 Hz, 3H), 0.92 (s, 3H).

Synthesis of 2-methoxyestra-1,3,5(10)-triene-3-ol (Compound #7): Into a stirring suspension of 2-methoxyestra-1,3,5(10)-trien-3-ol-17-one (#4, 8.1 g, 30 mmol) in diethylene glycol (60 mL), 1-butanol (20 mL) and hydrazine anhydrous (2 mL, 60 mmol) were added. The reaction mixture was heated under reflux for 1 hour and the solution cleared. After cooling reaction mixture to 50° C., KOH pellets (5.04 g, 90 mmol) were added and the butanol was distilled. The reaction mixture was heated at 50° C. for 2 hours and then cooled to room temperature. After the mixture was poured onto ice (50 g), 6N HCl (20 mL) was added with stirring to give white solid product. The product was separated by filtration, washed with cold water and dried under vacuum to give 7.5 g (90%) product. The product was purified on silica gel column eluted with CHCl$_3$/MeOH 99:1. $^1$H NMR in CDCl$_3$ confirmed the product as 2-methoxyestra-1,3,5(10)-triene-3-ol (7).

Representative procedure for preparation of 17-olefin-2-alkoxyestrane or 17-olefin-2-alkylestrane analogs—2-methoxy-17(20)-methyleneestra-1,3,5(10)-triene-3-ol (Compound #10): Potassium-tert-amylate (1.54 M, toluene, 4.35 mL 6.69 mmol, prepared as in Schow et al *J. Org. Chem.* 1979, 44, 3760) was added to a suspension of methyl triphenylphosphonium bromide (2.39 g, 6.69 mmol) in anhydrous benzene and refluxed for 30 min. 2-Methoxyestrone (#4, 300 mg, 1 mmol) in warm benzene (5 mL) was added and the mixture was refluxed for 3 h. The reaction was cooled to room temperature, poured into 100 mL water, washed with ether (2×100 mL). The combined organics were washed with 6 M HCl (1×100 mL), NaHCO$_3$ (saturated, 1×100 mL), water (1×100 mL), and brine (1×100 mL). Dry with sodium sulfate, filter and rotoevap to give a semi solid-yellowish oil. Purify by silica gel column chromatography using 95:5 chloroform:methanol as an eluent. Obtain 220 mg 2-methoxy-17(20)-methyleneestra-1,3,5(10)-triene-3-ol (#10, 0.738 mmol, 73% yield). Selected spectral data: $^1$H NMR (300 MHz, CDCl$_3$) δ 6.83 (s, 1H), 6.67 (s, 1H), 5.44 (br s, 1H), 4.70 (t, J=2.26 Hz, 2H), 3.89 (s, 3H), 2.86-2.74 (m, 2H), 2.64-2.49 (m, 1H), 2.39-2.17 (m, 3H), 2.02-1.78 (m, 3H), 1.65-1.19 (m, 6H), 0.85 (s, 3H). $^{13}$C NMR (75 MHz, CDCl$_3$) δ 162.2, 144.9, 143.8, 132.3, 130.0, 115.0, 108.5, 101.2, 77.6, 56.5, 53.9, 44.7, 39.2, 36.2, 29.9, 29.5, 28.1, 27.3, 24.3, 19.0. Analytical (C$_{20}$H$_{26}$O$_2$); calculated C=80.48; H=8.79; found C=80.60; H=8.77.

2-Methoxy-19-norpregna-1,3,5(10)17(20)-tetraene-3-ol (Compound #13): Reaction conditions in general same as in preparation of #10 except reaction scale was doubled and ethyl triphenylphosphonium bromide was used, from 2-methoxyestrone (613 mg, 2.04 mmol) obtain 540 mg (1.73 mmol, 84% yield) of final product. Selected spectral data: $^1$H NMR (300 MHz, CDCl$_3$) δ 6.82 (s, 1 H), 6.67 (s, 1 H), 5.44 (s, 1 H), 5.23-5.07 (m, 1 H), 3.88 (s, 3 H), 2.86-2.72 (m, 2 H), 2.51-2.38 (m, 2 H), 2.38-2.17 (m, 3 H), 1.99-1.88 (m, 1 H), 1.83-1.68 (m, 4 H), 1.49-1.20 (m, 6 H), 0.94 (s, Z isomer) and 0.80 (s, E isomer, total 3 H, ratio 5:1 respectively). $^{13}$C NMR (75 MHz, CDCl$_3$) δ 153.0 (E isomer) and 150.7 (Z isomer), 145.0, 143.8, 132.4, 130.0, 115.0, 113.8, 110.6 (Z isomer) and 108.4 (E isomer), 56.5, 55.6, 54.1, 45.0 (Z isomer) and 44.5 (E isomer), 39.0 (E isomer) and 38.7 (Z isomer), 37.7 (Z isomer) and 36.6 (E isomer), 31.9, 29.5, 28.1 (E isomer) and 28.0 (Z isomer), 27.7 (Z isomer) and 27.4 (E isomer), 24.5 (Z isomer) and 24.4 (E isomer), 19.5 (E isomer) and 17.4 (Z isomer), 14.0 (E isomer) and 13.6 (Z isomer). Analytical (C$_{21}$ H$_{28}$O$_2$); calculated C=80.73; H=8.79; found C=80.60; H=8.77.

Representative procedure for preparation of 17-alkyl-2-methoxyestradiol analogs: 2-methoxy-17β-methylestra-1,3,5(10)-triene-3-ol (Compound #16): 17-Methylene-2-methoxyestra-1,3,5(10)triene-3-ol (471.9 mg, 1.58 mmol) was dissolved ethyl acetate (20 ml) in a Parr bottle which was then flushed with Ar. Pd/C 10% (47.5 mg) was added and reaction mixture was then subjected to hydrogenation in Parr hydrogenater for an hour under 30 psi of hydrogen. Reaction mixture was then filtered through Celite and solvent was removed via rotary evaporation to yield 472.5 mg white crystals (1.57 mmol, 99% yield) of the final product 2-methoxy-17β-methylestra-1,3,5(10)-triene-3-ol. Selected spectral data: $^1$H NMR (300 MHz, CDCl$_3$) δ 6.82 (s, 1 H), 6.66 (s, 1 H), 5.43 (s, 1 H), 3.88 (s, 3 H), 2.85-2.70 (m, 2 H), 2.32-2.15 (m, 2 H), 1.94-1.68 (m, 4 H), 1.52-1.12 (m, 8 H), 0.90 (d, J=6.9 Hz, 3 H), 0.61 (s, 3 H). $^{13}$C NMR (75 MHz, CDCl$_3$) δ 144.90, 143.75, 132.65, 130.11, 114.99, 108.51, 56.46, 55.21, 45.58, 44.85, 42.74, 39.39, 37.97, 30.65, 29.52, 28.38, 27.21, 24.83, 14.34, 12.44. Analytical (C$_{20}$H$_{28}$O$_2$); calculated C=79.96; H=9.39; found C=79.98; H=9.49.

Preparation of 3-sulfamate-2-methoxyestra-1,3,5(10)-trien-17-one (Compound #19): Prepared as depicted in Scheme 3 using representative procedures. $^1$H NMR (300 MHz, CDCl$_3$) δ 7.06 (s, 1H), 6.93 (s, 1H), 4.93 (s, 2H), 3.88 (s, 3H), 2.86 (m, 2H), 2.58-1.26 (m, 313 H), 0.92 (s, 1H).

Preparation of 3-sulfamate-2-ethoxyestra-1,3,5(10)-trien-17-one (Compound #20): Prepared as depicted in Scheme 3 using representative procedures. $^1$H NMR (300 MHz, CDCl$_3$) δ 7.02 (s, 1H), 6.93 (s, 1H), 5.04 (br s, 2H), 4.12 (m, 2H), 3.73 (t, J=8.33 Hz, 1H), 2.78 (m, 2H), 2.28-1.17 (m, 13H), 1.43 (t, J=6.98 Hz, 3H), 0.78 (s, 3H).

Representative procedure for the preparation of triflic esters: Preparation of 2-methoxy-3-trifluoromethanesulfonylestra-1,3,5(10)-trien-17-one (Compound #22): 2-Methoxyestra-1,3,5(10)-trien-17-one-3-ol (2.4 g, 8.0 mmol) was dissolved in anhydrous dichloromethane (80 mL), anhydrous pyridine (20 mL) was added and the mixture was cooled to 0° C. Triflic anhydride (2 mL, 11.89 mmol, 1.5 eq) was added drop wise, then allowed to warm to room temperature with stirring for 18 h. The reaction mixture was poured into water (300 mL) and additional dichloromethane (150 mL) was added. The layers were separated, and the organic was washed with water (200 mL), 10% HCl (2×100 mL) and brine (100 mL). The organic layer was dried with MgSO$_4$, filtered and solvent was removed under reduced pressure. The product was purified using a SiO₂ Biotage FLASH apparatus using 5:1 hexanes:ethyl acetate as eluent, obtain 2.3801 g (5.51 mmol, 68% yield) as final product. ¹H NMR (300 MHz, CDCl₃) δ 6.96 (s, 1H), 6.95 (s, 1H), 3.90 (s, 3H), 2.87 (dd, J=4.2, 6.4 Hz, 2H), 2.61-2.95 (m, 8H), 1.74-1.36 (m, 5H), 0.94 (s, 3H).

Synthesis of 2-methoxy-3-(vinyl)estra-1,3,5(10)-triene-17-one (Compound #25): Tributyl(vinyl)tin(I) (200 μL, 0.6 mmol), lithium chloride (85 mg, 2 mmol), dichlorobis(triphenylphosphine)palladium (II) (10 mg, 0.05 mmol), 2,6-di-tert-butyl-4-methylphenol (2 mg) was added to a solution of 2-methoxy-3-trifluoromethanesulfoneestra-1,3,5(10)-triene-17-one (216 mg, 0.5 mmol) in anhydrous DMF (4 mL) at room temperature. The reaction was heated at 90° C. for 18 h and then cooled to room temperature. HF-pyridine (4 mL) was added and the reaction mixture was stirred for an additional 6 h. The mixture was diluted with EtOAc (20 mL) and filtered through Celite filter agent. The combined organics were washed with 1 N HCl (1×100 mL), water (1×100 mL), and brine (1×100 mL), dried with sodium sulfate, filtered, and concentrated via rotary evaporation to give a semi solid viscous oil. The product was purified on a flash silica gel column eluted with a hexane/EtOAc 5:1 mixture to give a white solid product (75 mg, 30%); ¹H NMR (CDCl₃) δ 7.20 (s, 1 H), 7.00 (dd, J=14, 11 Hz, vinyl, 1H), 6.82 (s, 1 H), 5.70 (d, J=18, vinyl, 1H), 5.22 (d, J=11, vinyl, 1H) 3.88 (s, 3 H), 2.85 (m, 2 H), 2.52 (dd, J=3 Hz, 1H), 2.44-1.88 (m, 6 H), 1.72-1.35 (m, 6 H), 0.95 (s, 3 H).

Alternate synthesis of 2-methoxy-3-(vinyl)estra-1,3,5(10)-triene-17β-ol (Compound #25a): Into a solution of 3-triflate-2-methoxyestra-1,3,5(10)-trien-17β-ol (218 mg, 0.5 mmol, prepared as in Shi *J. Am. Chem. Soc.* 2002, 124, 6921) in 4 mL DMF (anhydrous), was added tributyl(vinyl)Tin(1) (200 μL, 0.6 mmol), lithium chloride (85 mg, 2 mmol), dichlorobis(triphenylphosphine)palladium (II) (10 mg, 0.05 mmol), 2,6-di-tert-butyl-4-methylphenol (2 mg) at room temperature. The reaction was heated at 90° C. for 24 h and then cooled to room temperature. After adding HF-pyridine (4 mL) the reaction mixture was stirred for 16 h. After diluting with EtOAc (20 mL) the reaction mixture was filtered through Celite filter agent and the combined organics were washed with 1 N HCl (1×100 mL), water (1×100 mL), and brine (1×100 mL), then dried with sodium sulfate, filtered, and concentrated via rotary evaporation to give a semi solid viscous oil. The product was purified on a flash silica gel column eluted with a hexane/EtOAc 2:1 mixture to give a white solid product (140 mg, 60%). ¹H NMR (CDCl₃ δ 7.20 (s, 1 H), 7.00 (dd, J=14, 11 Hz, vinyl, 1H) 6.80 (s, 1 H), 5.70 (d, J=18 Hz, vinyl, 1H), 5.22 (d, J=11 Hz, vinyl, 1H), 3.85 (s, 3H), 2.72 (t, J=4 Hz, 1H), 2.85 (dd, J=5 Hz, 2H), 2.44-1.88 (m, 6 H), 1.80-1.15 (m, 8H), 0.80 (s, 3 H).

Synthesis of 2-methoxy-3-(carboxylic acid)estra-1,3,5(10)-triene-17-one (Compound #28): Potassium acetate (786 mg, 8 mmol), palladium (II) acetate (40 mg, 0.1 mmol), 1,1-bis(diphenylphosphine)-ferrocene (dppp) (200 mg, 0.4 mmol) were added to a solution of #22 (175 mg, 0.4 mmol) in 4 mL DMSO (anhydrous) at room temperature. The mixture was purged with CO gas for five minutes at room temperature then heated at 50° C. for 18 h under CO (balloon) and cooled to room temperature. After diluting with water, the reaction mixture was extracted with CH₂Cl₂ (1×20 mL) washed with 1 N HCl (1×10 mL), water (1×10 mL), and brine (1×10 mL), then dried with sodium sulfate, filtered, and concentrated via rotary evaporation to give a dark viscous oil. The product was purified on a flash silica gel column eluted with a hexane/EtOAc 1:2 mixture to give a white solid product (40 mg, 30%). ¹H NMR (CDCl₃) δ 10.92 (br s, 1H), 7.91 (s, 1H), 6.95 (s, 1 H), 4.05 (s, 3 H), 2.85 (dd, J=5 hz, 2H), 2.42-1.85 (m, 6 H), 1.65-1.15 (m, 8 H), 0.80 (s, 3 H).

Representative procedure for conversion of 3-(carboxyl acid)estrane derivative to 3-(carboxamide)estrane analog: Synthesis of 2-methoxy-3-carboxamideestra-1,3,5(10)-triene-17-one (Compound #31): A 150 mg portion of #28 (0.5 mmol) was dissolved in SOCl₂ at room temperature and then reaction mixture was heated at 50-60° C. for 2 h until gas evolution ceased. The remaining SOCl₂ was removed under vacuum to give a dark viscous oil. The product was diluted with THF anhydrous (5 mL) and NH₃ gas was bubbled for 5 minutes. Soon a white precipitate of NH₄Cl formed. The reaction mixture was diluted with THF, filtered and evaporated to give viscous product. The product was purified on a flash silica gel column eluted with a hexane/EtOAc 1:2 mixture to give a white solid product (60 g, 30%). ¹H NMR (CDCl₃) δ 7.95 (s, 1H), 7.82 (br s, 1H), 6.95 (s, 1 H), 5.72 (br s, 1H), 3.95 (s, 3 H), 2.95 (dd, J=5 Hz, 2H), 2.42-1.85 (m, 6 H), 1.65-1.15 (m, 8 H), 0.80 (s, 3 H).

Representative preparation of 3-(benzophenone imine) estrane derivatives —Preparation of 3-dibenzylimine-2-methoxyestra-1,3,5(10)-trien-17-one: 3-Trifluoromethanesulfonyl-2-methoxyestra-1,3,5(10)-trien-17-one (908 mg, 2.367 mmol) was dissolved in anhydrous toluene (6 mL) and Pd(OAc)₂ (30 mg, 5.7 mol %), rac BINAP (135 mg, 9.2 mol %), Cs₂CO₃ (1.0729 g, 3.29 mmol, dried overnight in vacuum oven) and benzophenone imine (436 μL, 2.6 mmol) were added. The mixture was refluxed for 60 h, cooled to room temperature, and diethyl ether (200 mL) was then added. The resulting mixture was filtered through celite, and solvent was removed under reduced pressure. The mixture was purified using SiO₂ with a Biotage FLASH apparatus with 5:1 hexanes:ethyl acetate as eluent. Obtain 906 mg (1.96 mmol, 58% yield) as final product. ¹H NMR (300 MHz, CDCl₃) δ 7.86-7.14 (m, 10H), 6.67 (s, 1H), 6.37 (s, 1H), 3.65 (s, 3H), 2.80-2.59 (m, 2H), 2.58-1.85 (m, 8H), 1.69-1.23 (m, 5H), 0.93 (s, 3H).

Representative procedure for hydrolysis of 3-(benzophenone imine)estrane derivatives to 3-aminoestrane derivatives—Preparation of 3-amino-2-methoxyestra-1,3,5(10)-trien-17-one (Compound #34): 3-Dibenzylimine-2-methoxyestra-1,3,5(10)-trien-17-one (906 mg, 1.96 mmol) was dissolved in THF (10 mL) and 2M HCl (2 mL) was added with stirring for 4 h. The reaction mixture was partitioned between 2:1 hexanes:ethyl acetate and 0.5M HCl (100 mL each). The aqueous layer was adjusted to pH=10 with 10M NaOH and then washed with dichlormethane (2×150 mL). The organic layer was washed with brine (100 mL), dried with Na₂SO₄, filtered and solvent was removed under reduced pressure. Obtain 438 mg (1.46 mmol, 75% yield) as final product. ¹H NMR (300 MHz, CDCl₃) δ 6.74 (s, 1H), 6.49 (s, 1H), 3.95 (br s, 2H), 3.84 (s, 3H), 2.89-2.69 (m, 2H), 2.60-1.88 (m, 8H), 1.74-1.34 (m, 5H), 0.93 (s, 3H).

3-Amino-2-ethoxyestra-1,3,5(10)-trien-17-one (Compound #35): Prepared as depicted in Scheme 3 using the representative procedures: ¹H NMR (300 MHz, CDCl₃) δ 6.74 (s, 1H), 6.50 (s, 1H), 4.05 (q, J=6.8 Hz, 2H), 3.70 (br s, 2H), 2.86-2.73 (m, 2H), 2.60-1.91 (m, 13H), 1.44 (t, J=6.8 Hz, 3H), 0.93 (s, 3H).

Representative procedure to prepare 3-fluoroestrane analogs: Preparation of 3-fluoro-2-methoxyestra-1,3,5(10)-trien-17-one (Compound #40): 3-Amino-2-methoxyestra-1,3,5(10)-trien-17-one (#34, 439 mg, 1.468 mmol) was dissolved in ethanol (10 mL) and HBF₄ (48% aqueous, 5 mL) and cooled to 0° C. NaNO₂ (124 mg, 1.797 mmol in water (0.5 mL) was added and stirred for 2.5 h. Diethyl ether (500 mL) was added, caused an oil to form. The supernatant was decanted off, and the flask was dried under vacuo causing the oil to foam. This foam was stored overnight under vacuo at 80° C. and was subsequently purified using $SiO_2$ Biotage FLASH apparatus with 2:1 hexanes:ethyl acetate as eluent. Obtain 92 mg (0.305 mmol, 21% yield). $^1$H NMR (300 MHz, $CDCl_3$) δ 6.91 (d, J=8.3 Hz, 1H), 6.82 (d, J=12.1 Hz, 1H), 3.88 (s, 3H), 2.95-2.77 (m, 2H), 2.61-1.92 (m, 8H), 1.73-1.36 (m, 5H), 0.94 (s, 3H). This compound was reduced with $NaBH_4$ at room temperature or $LiAlH_4$ at −78° C. to give the corresponding 17 alcohol.

Preparation of 3-Formamide-2-methoxyestra-1,3-5(10)-trien-17-ol (Compound #34): Same reaction procedure as the preparation of #88, except the 17-ester was cleaved with methanolic NaOH. $^1$H NMR (300 MHz, $CDCl_3$) δ 8.7 (d, J=11.7 Hz, rotamer 2), 8.44 (s, rotamer 1) and 8.10 (s, rotamer 2, total 1H), 7.72 (br s) and 7.58 (m, exchangeable amide H), 6.90 (d, J=16.2 Hz, rotamer 1), 6.84 (s, rotamer 1, 1H) (total of all H from 8.7-6.84 (m, 4H), 3.88 (s, rotamer 1) and 3.86 (s, rotamer 2, total 3H), 3.76 (m, 1H), 2.88-2.77 (m, 2H), 2.40-1.13 (m, 14H), 0.81 (s, 3H).

Preparation of 3-formamide-2-methoxyestra-1,3,5(10)-triene-17-one (Compound 43a): Prepared as depicted in Scheme 3 using representative procedures. $^1$H NMR (300 MHz, $CDCl_3$) δ 8.73 (d, J=11.5 Hz, rotamer 1), 8.46 (d, J=1.9 Hz, rotamer 1) and 8.13 (s, rotamer 2, total 1H), 7.76 (br s, rotamer 1) and 7.68-7.61 (m, rotamer 2, total 1H), 6.94 (s, rotamer 1) and 6.85 (s, rotamer 2), 6.82 (s, 1H) (all H between 8.73 and 6.82 total 4H), 4.16-4.01 (m, 2H), 2.94-2.76 (m, 2H), 2.62-1.15 (m, 15 H), 1.47 (app t, J=7.0 and 7.7 Hz, 3H), 0.94 (s, 3H).

Preparation of 3-Formamide-2-ethoxyestra-1,3-5(10)-trien-17-one (Compound #44a): Prepared as depicted in Scheme 3 using representative procedure for #88. $^1$H NMR (300 MHz, $CDCl_3$) δ 8.74 (d, J=11.7 Hz, rotamer 2), 8.46 (d, J=2.08 Hz, rotamer 1) and 8.13 (s, rotamer 2, total 1H), 7.76 (br s, rotamer 1) and 7.69-7.61 (m, rotamer 2, total 1H), 6.88 (d, J=15 Hz, rotamer 1), 6.28 (s, 1H) (all protons from 8.74-6.28 total 4H), 4.16-4.01 (m, 2H), 2.95-2.77 (m, 2H), 2.63-1.18 (m, 16H), 0.94 (s, 3H).

Preparation of 3-sulfamate-2-methoxyestra-1,3,5(10)-triene (Compound #46): Prepared as depicted in Scheme 4 using representative procedures. $^1$H NMR (300 MHz, $CDCl_3$) δ 7.06 (s, 1H), 6.97 (s, 1H), 4.96 (br s, 2H), 3.89 (s, 3H), 2.85-2.78 (m, 2H), 2.33-2.19 (m, 2H), 2.00-1.11 (m, 13H), 0.77 (s, 3H).

Preparation of 3-Triflic-2-methoxyestra-1,3,5(10)-triene (Compound #49): Same general procedure as the preparation of #22. $^1$H NMR (300 MHz, $CDCl_3$) δ 6.97 (s, 1H), 6.92 (s, 1H), 3.89 (s, 3H), 2.93-2.75 (m, 2H), 2.35-2.19 (m, 2H), 2.03-1.06 (m, 15H), 0.77 (s, 3H).

Preparation of 3-Vinyl-2-methoxyestra-1,3,5(10)-triene (Compound #52): Prepared as depicted in Scheme 4 using the representative procedures: $^1$H NMR (300 MHz, $CDCl_3$) δ 7.20 (s, 1H), 7.00 (dd, J=14.5, 11.2 Hz, 1H), 6.85 (s, 1H), 5.71 (d, J=17.7 Hz, 1H), 5.22 (d, J=11.3 Hz, 1H), 3.85 (s, 3H), 2.88-2.78 (m, 2H), 2.35-2.22 (m, 2H), 2.01-1.10 (m, 11H), 0.95 (t, J=7.54, 2H), 0.77 (s, 3H).

Preparation of (2-Methoxyestra-1,3,5(10)-trien-3-yl)-3-carboxamide (Compound #58): A 500 mL round-bottomed flask fitted with an overhead stirrer, a Claisen adaptor with a thermocouple probe and carbon monoxide inlet, and a vacuum inlet, was charged with 2-methoxyestra-1,3,5(10)-trien-3-yl-(trifluoromethyl)sulfonate (#49, 24 g, 57.35 mmol), anhydrous dimethylformamide (185 mL), palladium (II) chloride (0.500 g, 2.87 mmol), 1,3-bis(diphenylphospino)propane (2.37 g, 5.74 mmol), and 1,1,1,3,3,3-hexamethyldisilazane (48 mL, 229 mmol). The resulting yellow solution was stirred and evacuated, flushed with carbon monoxide (balloon) several times, then heated to 102° C. for 12 h. Additional palladium (II) chloride (0.500 g), 1,3-bis (diphenylphospino)propane (2.40 g), and hexamethyldisilazane (30 mL) were added and the mixture was re-evacuated, charged with carbon monoxide, and heated at 102° C. for an additional 12 h. Methanol (50 mL) was added and, after several minutes, the dark solution was partitioned with ethyl acetate (1000 mL) and 2 N sulfuric acid (1000 mL). The aqueous phase was extracted with ethyl acetate (2×250 mL), the combined organic extracts were washed with additional sulfuric acid (500 mL), and the aqueous phase was back-extracted with ethyl acetate (2×250 mL), and the total combined dark organic layers were washed with saturated aqueous sodium bicarbonate (500 mL) and dried over sodium sulfate (400 g). Suction-filtration through a plug of silica gel 60 (136 g) and concentration afforded 19 g of crude product as a red paste. This was purified by flash chromatography using 430 g of silica gel, and eluting with 10% ethyl acetate-dichloromethane. The product-containing fractions were concentrated, then taken up in acetone and re-concentrated (2×2000 mL). The yellow solid was then slurried in n-heptane (200 mL) overnight and isolated by suction-filtration. Removal of residual solvent, and drying to a constant weight over 3 h in a vacuum oven at 70° C. and 0.5 torr, afforded 5.07 g (28% overall) of #58 as an off-white powder. $^1$H NMR (300 MHz, $CDCl_3$) δ 10.82 (br s, 1H), 7.99 (s, 1H), 6.95 (s, 1 H), 4.05 (s, 3 H), 2.95 (dd, 2 H, J=5), 2.15 (m 2H,) 2.02-1.65 (m, 6 H), 1.55-1.15 (m, 8 H), 0.80 (s, 3 H). C NMR (125 MHz, $CDCl_3$) δ 167.6, 156.1, 147.1, 132.9, 130.0, 116.0, 108.7, 56.2, 54.0, 45.2, 41.2, 40.7, 39.0, 38.6, 28.8, 28.2, 26.7, 25.5, 20.8, 17.8.

Preparation of 3-amino-2-methoxyestra-1,3,5(10)-triene (Compound #61): Prepared as depicted in Scheme 4 using representative procedures. $^1$H NMR, ($CDCl_3$,) δ 6.80 (1H, s, aromatic), 6.48 (1H, s, aromatic), 3.87 (3H, s), 3.65 (2H, broad, $NH_2$), 2.75 (2H, dd, J=5.0, 3.0 Hz), 2.25 (2H, m), 1.97 (2H, m), 1.80-1.05 (11H, m), 0.80 (3H, s).

Preparation of 3-formamide-2-methoxyestra-1,3,5(10)-triene (Compound #64): Prepared as depicted in Scheme 4 using representative procedures. $^1$H NMR (300 MHz, $CDCl_3$) δ 8.70 (d, J=11.7 Hz, rotamer 2), 8.44 (d, J=1.7 Hz, rotamer 2) and 8.09 (s, rotamer 1, total 1H), 7.71 (br s, rotamer 1) and 7.62-7.53 (m, rotamer 2, total 1H), 6.90 (d, J=10.4 Hz, rotamer 1), 6.85 (s, 1H) (all protons from 8.70-6.85 total 4H), 3.88 (s, rotamer 1) and 3.86 (s, rotamer 2, total 3H), 2.91-2.77 (m, 2H), 2.33-2.18 (m, 2H), 2.00-1.08 (m, 13H), 0.77 (s, 3H).

Representative procedure for preparation of sulfamate derivatives: 17-methylene-3-sulfamate-2-methoxyestra-1,3, 5(10)-triene (Compound #70): Sodium hydride (268 mg, 11.2 mmol) was added to anhydrous DMF (40 mL) and cooled to 0° C., then 17-methylene-2-methoxyestra-1,3,5 (10)-triene-3-ol in anhydrous DMF (8 mL) was added drop wise. The mixture was stirred for 2 h at room temperature. Sulfamoyl chloride (prepared freshly as in Peterson et al *J. Med. Chem.* 1992, 35, 3991) was added in portions at 0° C. and stirred overnight at room temperature. The mixture was poured into water (100 mL) and washed with ethyl acetate (3×100 mL). The combined organic layers were washed with water (4×100 mL) and brine (100 mL). The organics were dried with $MgSO_4$, filtered and solvent was removed under reduced pressure to obtain a white solid. After drying under vacuo for 24 h, obtain 441 mg product (70% yield, 1.17 mmol). $^1$H NMR (300 MHz, $CDCl_3$) δ 7.07 (s, 1H), 6.98 (s, 1H), 4.96 (s, 2H), 4.71 (s, 2H), 3.91 (s, 3H), 2.93-2.73 (m, 2H), 2.65-1.15 (m, 13 H), 0.85 (s, 3H).

Preparation of 3-triflic-17-methylene-2-methoxyestra-1,3,5(10)-triene (Compound #73): Prepared as depicted in Scheme 5 using representative procedures. $^1$H NMR (300 MHz, CDCl$_3$) δ 6.98 (s, 1H), 6.93 (s, 1H), 4.73-4.68 (m, 2H), 3.90 (s, 3H), 2.88-2.78 (m, 2H), 2.64-2.50 (m, 1H), 2.41-1.18 (m, 13H), 0.85 (s, 3H).

Alternate preparation of 3-carboxamide estrane derivatives directly from triflate—Preparation of 2-Methoxy-17-methyleneestra-1,3,5(10)-triene-3-carboxamide (Compound #82): General procedure based on *Tetrahedron Letters*, 1998, 39, 2835-2838. A 250 mL three-necked flask equipped with an overhead stirrer, thermocouple, and nitrogen inlet, was charged with 2-Methoxy-17-methyleneestra-1,3,5(10)-trien-3-yl(trifluoromethyl)-sulfonate #73 (20.0 g, 46.5 mmol), palladium (II) chloride (0.41 g, 2.3 mmol), 1,3-bis(diphenylphosphino) propane (1.9 g, 4.6 mmol), 1,1,1,3,3,3-hexamethyldisilazane (38.8 mL, 186 mmol) and anhydrous dimethylformamide (150 mL). The resulting orange solution was evacuated and back-filled with nitrogen three times, then evacuated and back-filled with carbon monoxide three times. The reaction was warmed to 100° C. and stirred under a carbon monoxide atmosphere (balloon) for 18 hours, during which time the solution became dark red. The heat was removed, methanol (40 mL) was added, and the solution allowed to stir for 10 minutes. The solution was poured into ethyl acetate (1 L) and extracted with 2 N H$_2$SO$_4$ (1 L). The aqueous layer was extracted with ethyl acetate (3×500 mL). Each of the ethyl acetate extracts was washed with 2 N H$_2$SO$_4$ (500 mL). The combined organic phases were washed with saturated aqueous sodium bicarbonate (1 L) and dried over sodium sulfate (500 g). This suspension was suction-filtered through a bed of silica gel 60 (102 g), and the filtrate concentrated to dryness affording 16.02 g (106% recovery) of crude #82. The crude product was purified on silica gel 60 (500 g, flash column) eluting with methylene chloride (2 L) then 2% methanol-methylene chloride (4 L) then 4% methanol-methylene chloride (4 L). Chromatography failed to remove all impurities so fractions containing product were combined, concentrated to dryness, and repurified on silica gel 60 (500 g, flash column) eluting with methylene chloride (2 L) then 1:5 ethyl acetate-methylene chloride. Concentration of the pure fractions (TLC, 1:5 ethyl acetate-methylene chloride, R$_f$=0.3, UV detection) and drying in a vacuum oven at 80° C., afforded 12.3 g (81% overall) of compound #82 as a light-yellow solid with residual methylene chloride by NMR. The material was dissolved in 10:1 acetone/methanol (1.35 L), concentrated to dryness to remove residual solvents, and dried in vacuo to yield 11.36 g of compound #16 (75% overall yield) as a light-yellow solid. $^1$H-NMR (showed 0.09 wt % acetone present), $^{13}$C-NMR and Mass Spectral analysis were consistent with desired structure. $^1$H NMR (300 MHz, CDCl$_3$) δ 7.94 (s, 1H), 7.63 (br s, 1H), 6.95 (s, 1H), 5.70 (br s, 1H), 4.71 (s, 2H), 3.97 (s, 3H), 2.97-2.82 (m, 2H), 2.65-1.19 (m, 13H), 0.86 (s, 3H). $^{13}$C NMR (CDCL$_3$, 125 MHz) δ 167.2, 161.4, 155.8, 146.3, 132.6, 129.6, 118.0, 108.4, 100.9, 55.9, 53.5, 44.9, 44.2, 38.2, 35.6, 29.4, 28.4, 27.4, 26.4, 23.9, 18.5.

Preparation of 3-amino-17-methylene-2-methoxyestra-1,3,5(10)-triene (Compound #85): Prepared as depicted in Scheme 5 using representative procedures. $^1$H NMR (300 MHz, CDCl$_3$) δ 6.78 (s, 1H), 6.49 (s, 1H), 4.72-4.67 (m, 2H), 3.85 (s, 3H), 3.67 (br s, 2H), 2.83-2.71 (m, 2H), 2.63-2.48 (m, 1H), 2.41-1.14 (m, 13H), 0.85 (s, 3H).

Preparation of 3-amino-17-methylene-2-ethoxyestra-1,3,5(10)-triene (Compound #86): Prepared as depicted in Scheme 5 using representative procedures. $^1$H NMR (300 MHz, CDCl$_3$) δ 6.77 (s, 1H), 6.48 (s, 1H), 4.69 (s, 2H), 4.06 (q, J=7.0 Hz, 2H), 3.70 (br s, 2H), 2.87-2.65 (m, 2H), 2.63-2.48 (m, 1H), 2.40-2.11 (m, 2H), 2.03-1.17 (m, 10H), 1.43 (t, J=6.8 Hz, 3H), 0.84 (s, 3H).

Representative preparation of 3-formamide estrane derivatives: Preparation of 3-formamide-17-methylene-2-methoxyestra-1,3,5(10)-triene (Compound #88): 3-Amino-17-methylene-2-methoxyestra-1,3,5(10)-triene (293 mg, 0.99 mmol) was dissolved in chloroform (1 mL) and trimethylacetyl formic anhydride (170 mg, 1.30 mmol, prepared as in Vlietstra et al *Recueil*, 1982, 101, 460) was added. The mixture was stirred 40 min, after which, the solvent was removed under reduced pressure. The product was purified by titurating with hexanes and isolating the precipitate by decanting after the precipitate was centrifuged. Obtain 150 mg white powder (0.417 mmol, 42% yield). $^1$H NMR (300 MHz, CD$_3$OD) δ 8.27 (s, 1H), 7.88 (s, 1H), 6.94 (s, 1H), 4.72-4.67 (m, 2H), 3.88 (s, rotamer 1) and 3.86 (s, rotamer 2, total 3H), 2.87-2.76 (m, 2H), 2.66-1.19 (m, 13H), 0.87 (s, 3H).

Preparation of 3-formamide-17-methylene-2-ethoxyestra-1,3,5(10)-triene (Compound #89): Prepared as depicted in Scheme 5 using representative procedures. $^1$H NMR (300 MHz, CDCl$_3$) δ 8.73 (d, J=11.7 Hz, rotamer 2), 8.46 (d, J=1.88 Hz, rotamer 2) and 8.11 (s, total 1H), 7.75 (br s, rotamer 1) and 7.62 (br s, rotamer 2, exchangeable amide H), 6.90 (d, J=18 Hz, rotamer 1), 6.84 (s, all protons from 8.73-6.84 total 4H), 4.70 (s, 2H), 4.16-4.02 (m, 2H), 2.93-2.79 (m, 2H), 2.66-1.16 (m, 16H), 0.85 (s, 3H).

Preparation of 3-sulfamate-17-ethylene-2-methoxyestra-1,3,5(10)-triene (Compound #94): Prepared as depicted in Scheme 6 using representative procedures. $^1$H NMR (300 MHz, CDCl$_3$) δ 7.06 (s, 1H), 6.96 (s, 1H), 5.24-5.13 (m, 1H), 4.96 (s, 2H), 3.90 (s, 3H), 2.90-2.78 (m, 2H), 2.51-1.20 (m, 16H), 0.94 (s, Z isomer) and 0.80 (s, E isomer, total 3H, ratio 5:1 respectively).

Preparation of 3-amino-17-ethylene-2-methoxyestra-1,3,5(10)-triene (Compound #109): Prepared as depicted in Scheme 6 using representative procedures. $^1$H NMR (300 MHz, CDCl$_3$) δ 6.76 (s, 1H), 6.48 (s, 1H), 5.22-5.12 (m, 1H), 3.85 (s, 3H), 3.66 (br s, 2H), 2.86-2.66 (m, 2H), 2.53-2.16 (m, 4H), 2.00-1.20 (m, 12H), 0.93 (s, Z isomer) and 0.80 (s, E isomer, total 3H, ratio 5:1 respectively).

Preparation of 3-formamide-17-ethylene-2-methoxyestra-1,3,5(10)-triene (Compound #112): Prepared as depicted in Scheme 6 using representative procedures. $^1$H NMR (300 MHz, CDCl$_3$) δ 8.70 (d, J=11.7 Hz, rotamer 2), 8.44 (d, J=1.89 Hz, rotamer 1) and 8.09 (s, rotamer 2, total 1H), 7.72 (br s, rotamer 1) and 7.63-7.52 (m, rotamer 2, exchangable amide H), 6.90 (d, J=14.7 Hz, rotamer 1), 6.84 (s, 1H) (all protons from 8.70-6.84 total 4H), 5.24-5.14 (m, 1H), 3.89 (s, rotamer 1) and 3.86 (s, rotamer 2, total 3H), 2.90-2.78 (m, 2H), 2.53-2.18 (m, 5H), 2.03-1.23 (m, 11H), 0.93 (s, Z isomer) and 0.80 (s, E isomer, total 3H, ratio 5:1 respectively).

Preparation of 3-sulfamate-17-methyl-2-methoxyestra-1,3,5(10)-triene (Compound #118): Prepared as depicted in Scheme 7 using representative procedures. $^1$H NMR (300 MHz, CDCl$_3$) δ 7.06 (s, 1H), 6.97 (s, 1H), 4.95 (s, 2H), 3.90 (s, 3H), 2.89-2.74 (m, 2H), 2.35-2.15 (m, 2H), 1.99-1.12 (m, 12H), 0.91 (d, J=6.8 Hz, 3H), 0.62 (s, 3H).

Preparation of 3-sulfamate-17-methyl-2-ethoxyestra-1,3,5(10)-triene (Compound #119): Prepared as depicted in Scheme 7 using representative procedures. $^1$H NMR (300 MHz, CDCl$_3$) δ 7.042 (s, 1H), 6.96 (s, 1H), 4.99 (s, 2H), 4.21-4.06 (m, 2H), 2.87-2.74 (m, 2H), 2.32-1.12 (m, 17H), 0.90 (d, J=5.30 Hz, β isomer) and 0.79 (d, J=3.77 Hz, α isomer, total 3H, ratio 4:1 respectively), 0.61 (s, 3H).

Preparation of 3-amino-17-methyl-2-methoxyestra-1,3,5(10)-triene (Compound #133): Prepared as depicted in Scheme 7 using representative procedures. $^1$H NMR (300 MHz, CDCl$_3$) δ 6.77 (s, 1H), 6.48 (s, 1H), 3.85 (s, 3H), 2.87-2.66 (m, 2H), 2.33-2.14 (m, 2H), 1.95-1.11 (m, 14H), 0.89 (d, J=6.78 Hz, β isomer) and 0.79 (d, J=3.77 Hz, α isomer, total 3H, ratio 4:1 respectively), 0.61 (s, 3H).

Preparation of 3-formamide-17-methyl-2-methoxyestra-1,3,5(10)-triene (Compound #136): Prepared as depicted in Scheme 7 using representative procedures. $^1$H NMR (300 MHz, CDCl$_3$) δ 8.70 (d, J=11.7 Hz, rotamer 2), 8.43 (d, J=1.89 Hz, rotamer 1) and 8.09 (s, rotamer 2, total 1H), 7.72 (br s) and 7.61-7.52 (m, exchangeable H), 6.90 (d, J=10.9 Hz, rotamer 1), 6.85 (s, 1H) (all protons from 8.70-6.85 total 4H), 3.88 (s, rotamer 1) and 3.86(s, rotamer 2, total 3H), 2.93-2.73 (μ, 2H), 2.34-1.10 (μ, 14H), 0.90 (d, J=6.78 Hz, β isomer) and 0.79 (d, J=3.7 Hz, α isomer, total 3H, ratio 4:1 respectively), 0.61 (s, 3H).

Example 2

Determination of in vitro anti-proliferative activity of substituted estradiol analogs: In vitro anti-proliferative or anti-mitogenic activity was determined using a commercially available cell-based assay in 96-well tissue culture plates with assessment of proliferation by evaluating DNA synthesis through incorporation into DNA of immuno-reactive (BrdU) nucleotides. The cell types used are commercially available (MDA-MB-231: breast cancer; U87-MG: glioblastoma; PC3: prostate cancer; HUVEC: non-transformed early passage human umbilical vein endothelial cells). These assays, and the many assay variations possible to determine in vitro anti-proliferative or anti-mitogenic activity, are well known to those skilled in the art. The concentration which causes 50% inhibition of proliferation (IC$_{50}$) was estimated from a dose-response curve generally carried out with a range of concentrations from ≧100 microg/mL to ≦0.01 microg/mL. The results of the tests are shown below in Table IV.

TABLE IV

| Compound # | IC$_{50}$ for MDA-MB-231 (μM) | IC$_{50}$ for U87-MG (μM) | IC$_{50}$ for PC3 (μM) | IC$_{50}$ for HUVEC (μM) |
|---|---|---|---|---|
| 1 | 0.69 ± 0.14 | 1.48 ± 0.62 | 1.08 ± 0.50 | 0.68 ± 0.15 |
| 2 | 0.650 ± 0.23 | | | 0.14 ± 0.07 |
| 3 | 3.99 ± 1.12 | 2.68 ± 0.22 | 2.22 ± 0.13 | 0.52 ± 0.14 |
| 4 | 11.7 | 10.5 | 13.7 | 12.6 |
| 7 | 2.20 ± 0.52 | 7.35 ± 0.43 | 8.49 ± 2.49 | 1.32 ± 0.56 |
| 10 | 0.58 ± 0.31 | | | 0.26 ± 0.23 |
| 13 | 2.63 ± 0.20 | 2.37 ± 0.34 | 1.15 ± 0.40 | 0.37 ± 0.08 |
| 16 | 3.33 ± 0.23 | 9.39 ± 0.43 | 6.46 ± 2.31 | 2.40 ± 0.45 |
| 19 | 0.60 ± 0.43 | 0.80 ± 0.23 | 0.51 ± 0.24 | 0.18 ± 0.04 |
| 20 | 7.52 ± 2.04 | 19.82 ± 2.32 | 8.93 ± 0.61 | 2.59 ± 0.25 |
| 25 | 2.57 ± 0.29 | 2.20 ± 0.06 | 1.43 ± 0.40 | 0.58 ± 0.01 |
| 25a | 8.93 ± 0.61 | 7.81 ± 1.30 | 6.34 ± 0.08 | 1.96 ± 0.05 |
| 28 | >100 ± 0 | >100 ± 0 | >100 ± 0 | >100 ± 0 |
| 31 | 0.7 ± 0.12 | 1.07 ± 0.15 | 0.7 ± 0.03 | 0.79 ± 0.20 |
| 34 | 46.91 ± 8.15 | 81.54 ± 20.37 | >100 | 23.42 ± 4.14 |
| 35 | 10.64 ± 2.98 | 26.05 ± 1.40 | 9.25 ± 1.58 | 16.46 ± 2.02 |
| 37 | 2.48 ± 0.50 | 10.83 ± 1.04 | 9.79 ± 1.93 | 2.32 ± 0.38 |
| 40 | 2.94 ± 0.80 | 25.98 ± 3.38 | 9.26 ± 0.73 | 2.10 ± 0.23 |
| 43 | 0.78 ± 0.01 | 2.70 ± 0.22 | 1.34 ± 0.02 | 0.07 ± 0.02 |
| 43A | 1.22 ± 0.60 | 0.94 ± 0.09 | 0.61 ± 0.27 | 0.53 ± 0.22 |
| 44A | 24.87 ± 5.63 | 21.10 | 27.70 ± 0.62 | 13.17 ± 2.20 |
| 46 | 0.38 ± 0.15 | 0.72 ± 0.04 | 0.38 ± 0.21 | 0.21 ± 0.15 |
| 52 | 1.86 ± 0.22 | 3.14 ± 0.52 | 2.12 ± 0.64 | 0.58 ± 0.04 |
| 58 | 5.23 ± 1.95 | 4.52 ± 1.3 | 2.58 ± 0.36 | 1.42 ± 0.41 |
| 61 | 7.62 ± 0.43 | 10.20 ± 3.78 | 8.63 ± 0.18 | 6.43 ± 1.32 |
| 64 | 8.29 ± 1.64 | 23.24 ± 2.0 | 9.24 ± 0.59 | 5.80 ± 0.73 |
| 70 | 0.56 ± 0.02 | 0.70 ± 0.06 | 0.91 ± 0.32 | 0.58 ± 0.03 |
| 73 | >100 | >100 | >100 | >100 |
| 82 | 0.19 ± 0.08 | 0.25 ± 0.02 | 0.25 ± 0.01 | 0.12 ± 0.06 |
| 85 | 2.11 ± 0.57 | 5.51 ± 0.46 | 2.40 ± 0.39 | 1.00 ± 0.19 |
| 86 | 2.13 ± 0.12 | 7.29 ± 2.26 | 2.75 ± 0.22 | 2.31 ± 0.05 |
| 88 | 0.30 ± 0.08 | 0.53 ± 0.24 | 0.24 ± 0.06 | 0.22 ± 0.03 |
| 89 | 2.41 ± 0.13 | 7.73 | 1.59 ± 0.19 | 2.10 ± 0.02 |
| 94 | 0.58 ± 0.02 | 0.64 ± 0.09 | 0.66 ± 0.05 | 0.59 ± 0.00 |
| 109 | 1.94 ± 0.27 | 2.35 ± 0.41 | 0.92 ± 0.11 | 0.72 ± 0.10 |
| 112 | 0.56 ± 0.02 | 0.77 ± 0.06 | 0.74 ± 0.01 | 0.58 ± 0.00 |
| 113 | 11.98 | 19.13 | 20.64 | 7.08 |
| 118 | 0.66 ± 0.10 | 0.64 ± 0.01 | 0.82 ± 0.06 | 0.59 ± 0.1 |
| 119 | 1.55 ± 0.39 | 6.41 | 0.83 | 0.91 ± 0.09 |
| 133 | 7.31 ± 0.58 | 14.87 ± 0.01 | 7.16 ± 1.42 | 2.65 ± 0.77 |
| 136 | 0.61 ± 0.00 | 0.64 ± 0.01 | 0.70 ± 0.10 | 0.59 ± 0.00 |

All of the publications mentioned herein are hereby incorporated by reference in their entireties. The above examples are merely demonstrative of the present invention, and are not intended to limit the scope of the appended claims.

The invention claimed is:

1. A compound of the general formula:

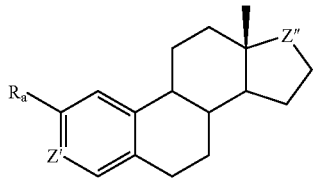

wherein $R_a$ is selected from —OCH$_3$; —OCH$_2$CH$_3$; or —CCCH$_3$; Z' is selected from >C—F, >C—NH$_2$, >CCONH$_2$, >C—NHCOH, >C—OSO$_2$NH$_2$, or >C—CHCH$_2$, and Z" is selected from >C(H$_2$), >C(H)—CH$_3$, >C=CH$_2$, >C=CHCH$_3$, or >C=O; provided that when Z' is >C—OSO$_2$NH$_2$ and Z" is >C(H$_2$), >C(H)—CH$_3$, >C=O, >C=CH$_2$ or >C=CHCH$_3$, $R_a$ is neither —OCH$_3$ nor —OCH$_2$CH$_3$, and when Z' is >C—NH$_2$, Z" is not >C=O and provided that Z' is not >C—NH$_2$ when $R_a$ is —OCH$_3$ or —OCH$_2$CH$_3$ and Z" is >C(H$_2$).

2. The compound of claim 1, wherein the compound is:

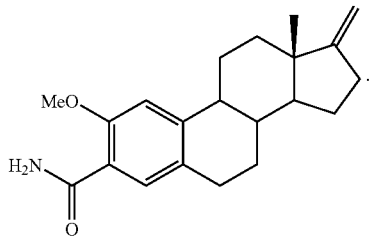

3. The compound of claim 1, wherein the compound is:

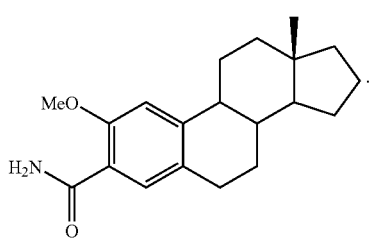

4. The compound of claim 1, wherein the compound is

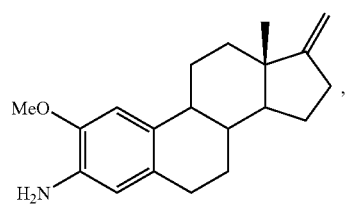

-continued

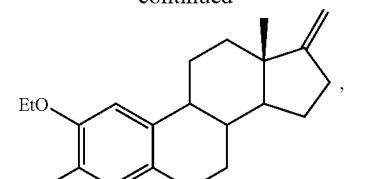

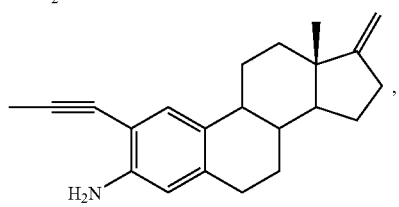

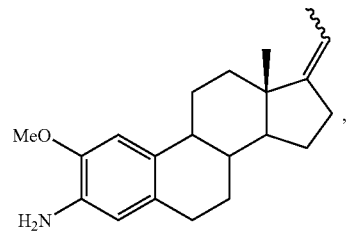

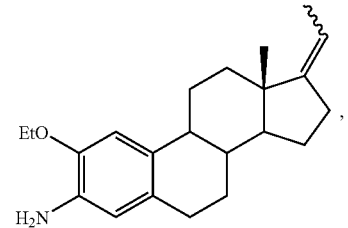

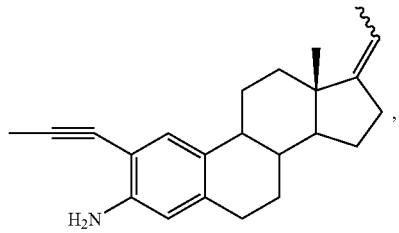

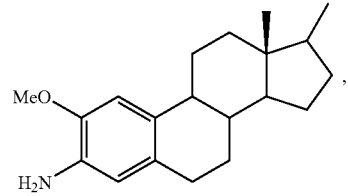

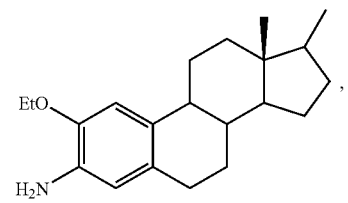

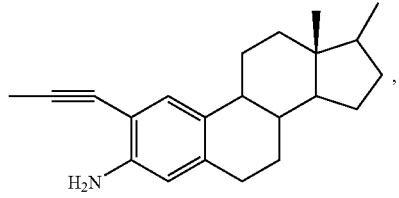

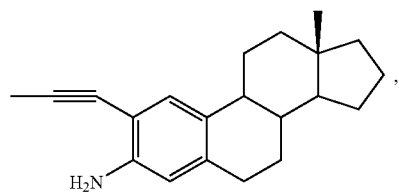,
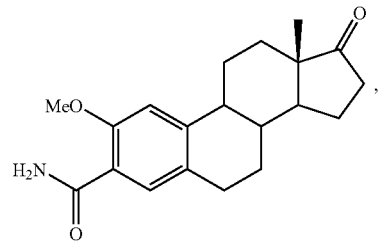,
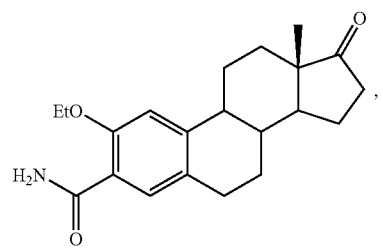,
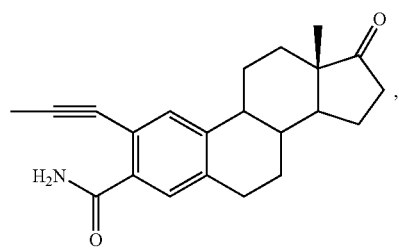,
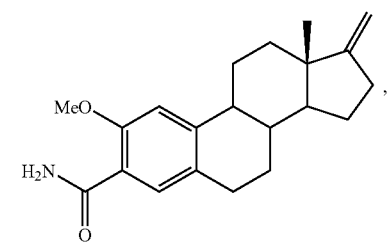,
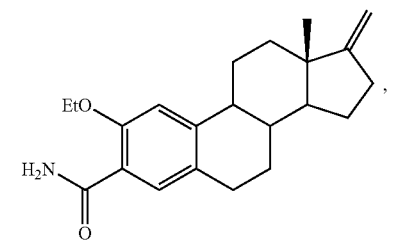,
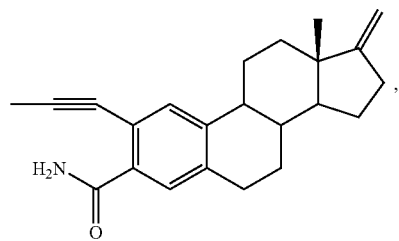,
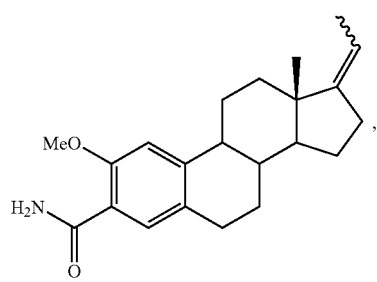,
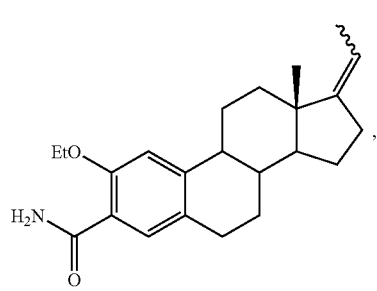,
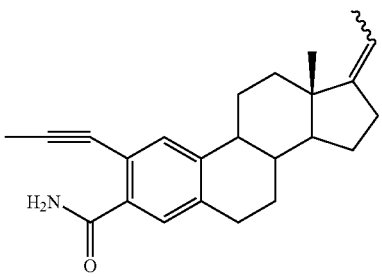,
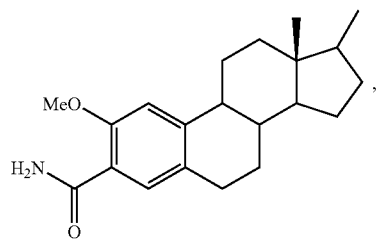,
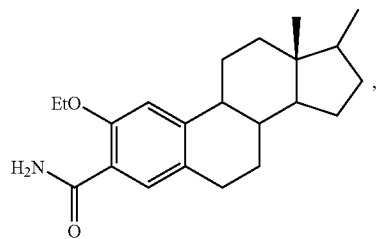,
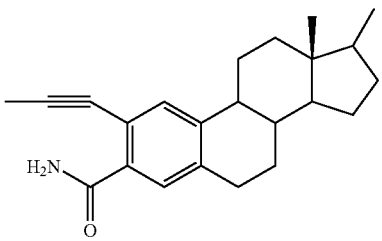, -continued
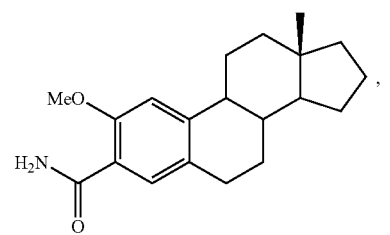
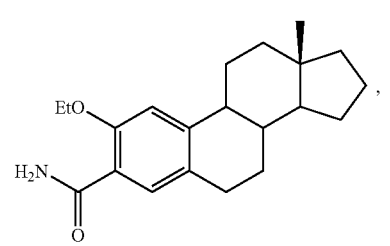
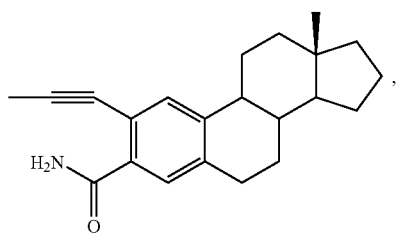
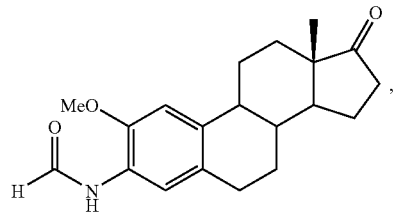
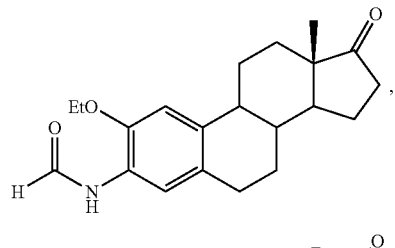
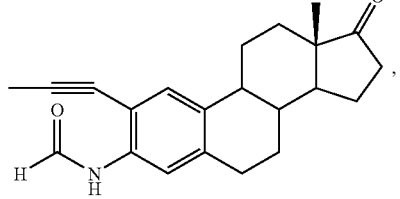
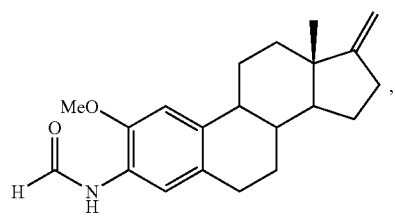
-continued
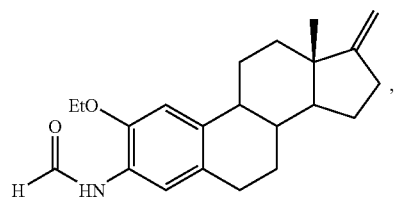
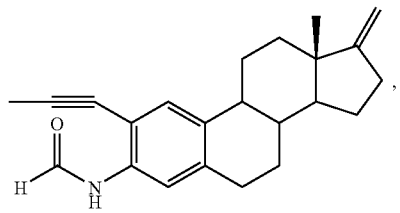
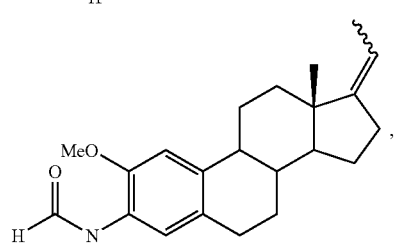
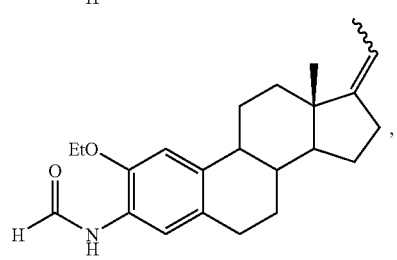
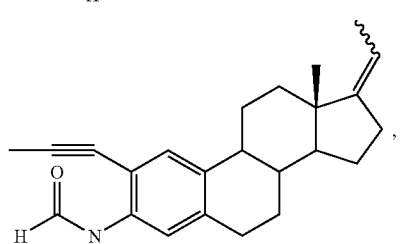
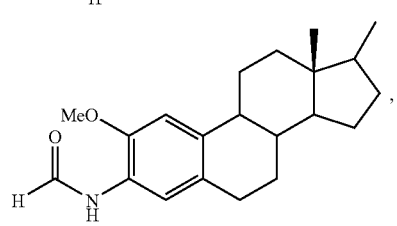
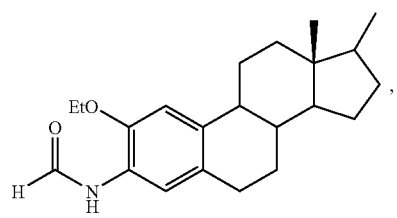

-continued
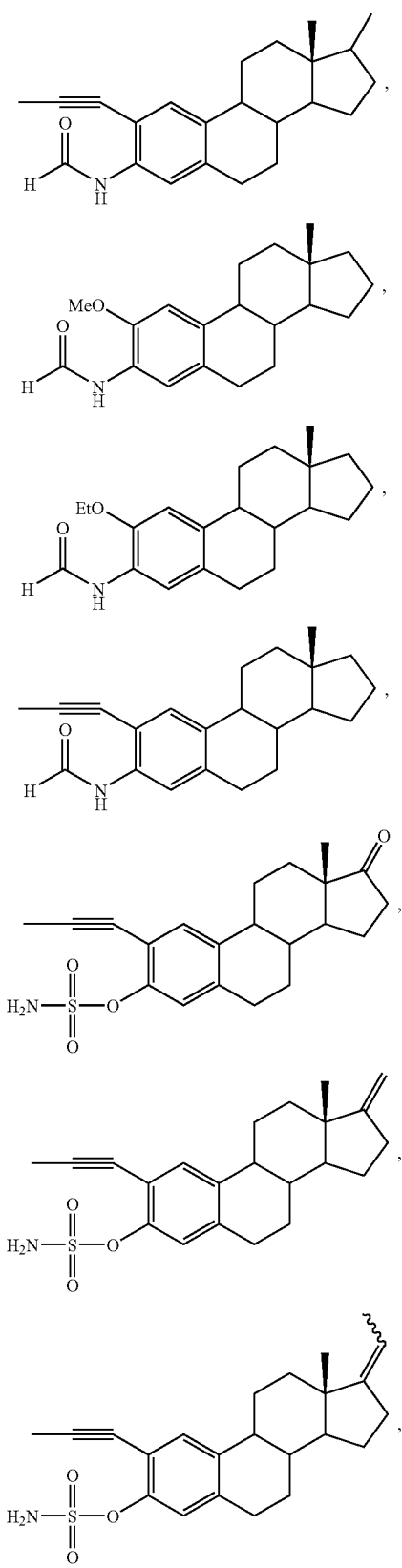
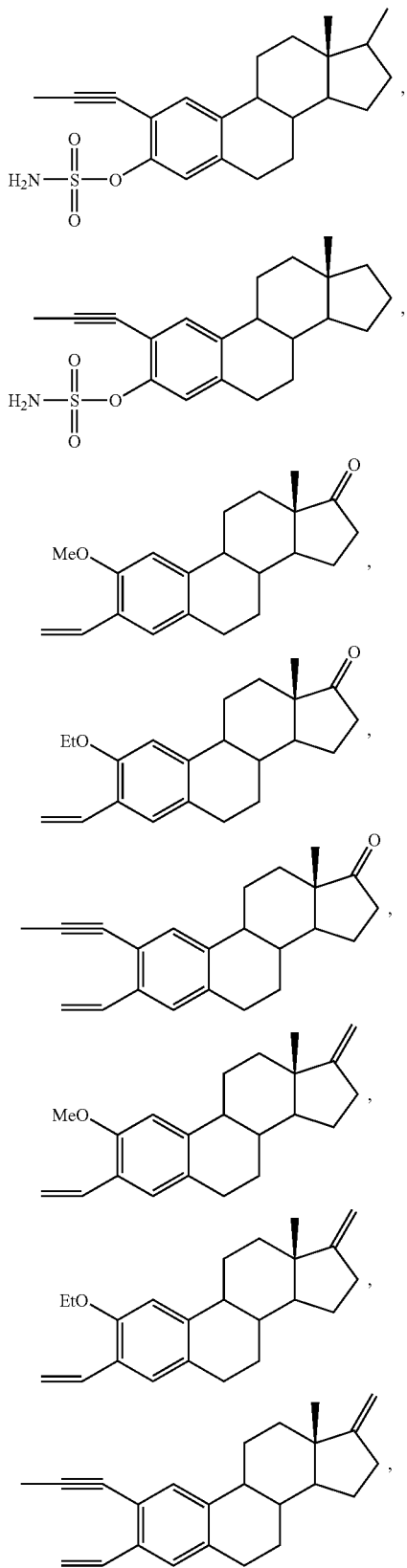

-continued
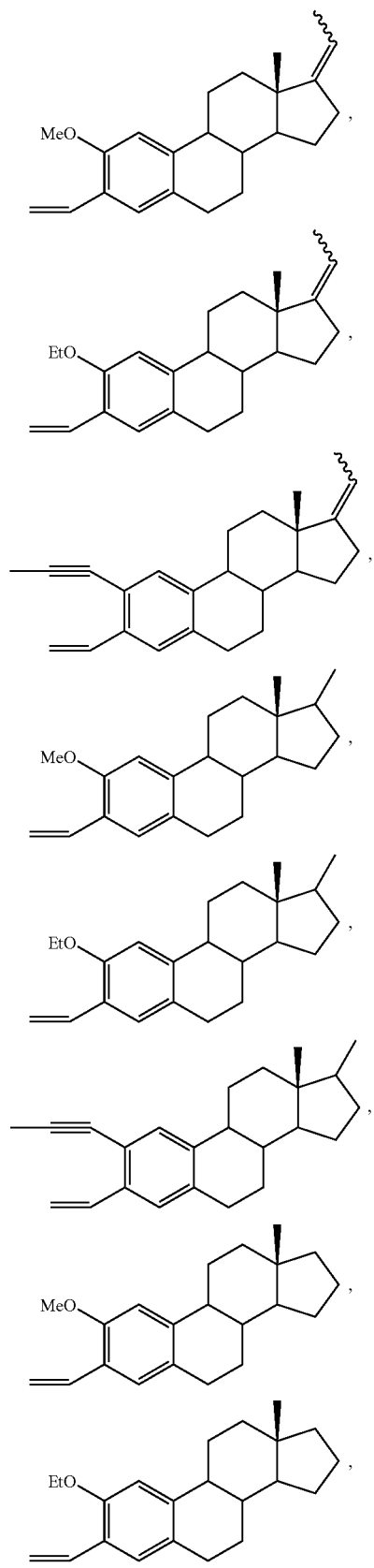
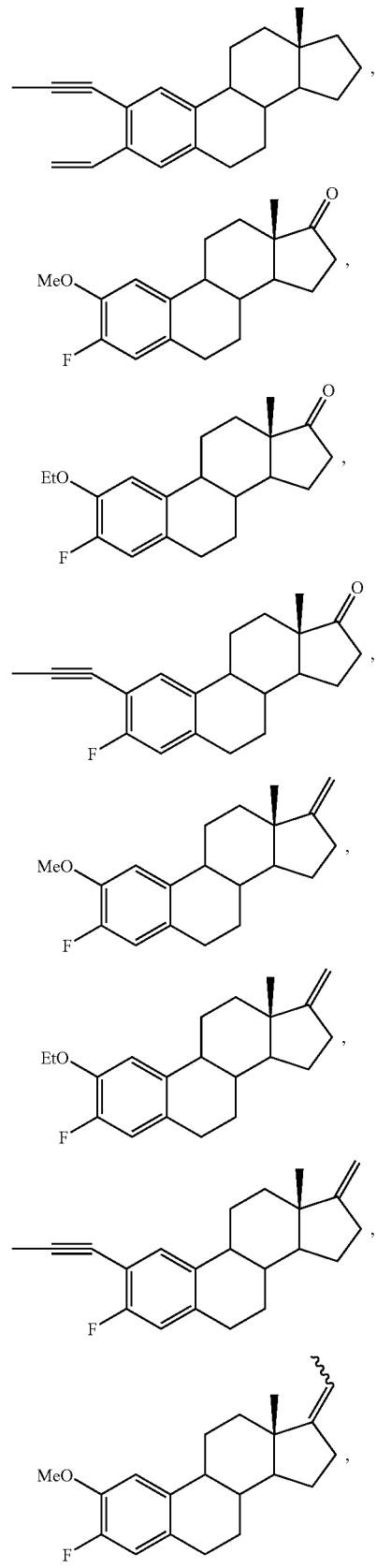

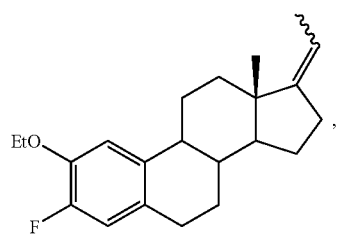

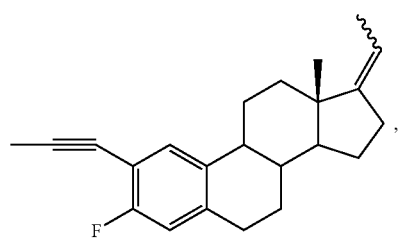

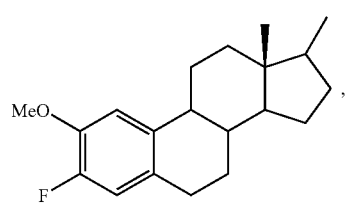

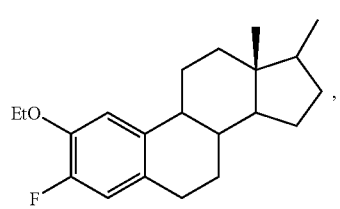

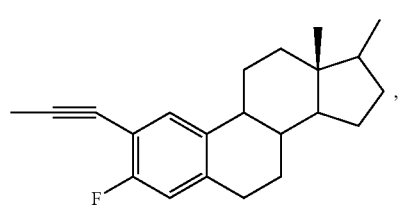

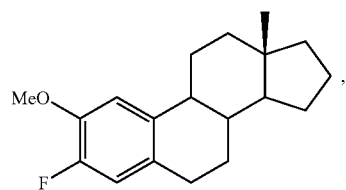

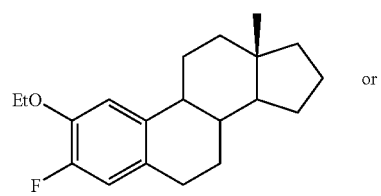 or

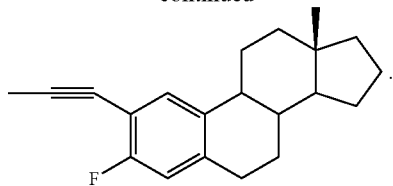

5. A pharmaceutical composition comprising:
a pharmaceutical carrier or excipient; and
a compound having the formula

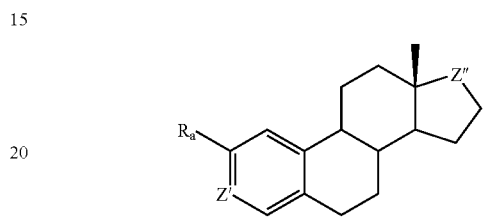

wherein $R_a$ is selected from —OCH$_3$, —OCH$_2$CH$_3$ or —CCCH$_3$;

Z' is selected from >C—F, >C—NH$_2$, >CCONH$_2$, >C—NHCOH, >C—OSO$_2$NH$_2$ or >C—CHCH$_2$; and Z" is selected from >C(H$_2$), >C(H)—CH$_3$, >C=CH$_2$, >C=CHCH$_3$ or >C=O, provided that when Z' is >C—OSO$_2$NH$_2$ and Z" is >C(H$_2$), >C(H)—CH$_3$, >C=O, >C=CH$_2$ or >C=CHCH$_3$, $R_a$ is neither —OCH$_3$ nor —OCH$_2$CH$_3$, and when Z' is >C—NH$_2$, Z" is not >C=O and provided that Z' is not >C—NH$_2$ when $R_a$ is —OCH$_3$ or —OCH$_2$CH$_3$ and Z" is >C(H$_2$), in an effective amount upon administration in a daily dose, a daily sub-dose, or an appropriate fraction thereof to a human or an animal.

6. A pharmaceutical composition comprising:
a pharmaceutical carrier or excipient; and
a compound selected from

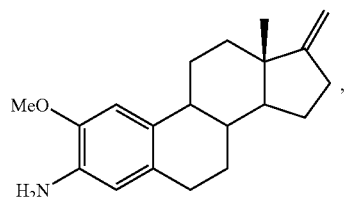

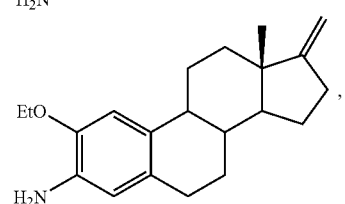

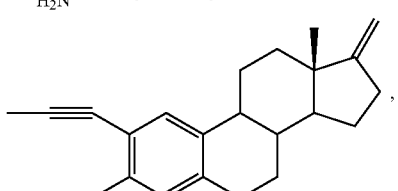

-continued
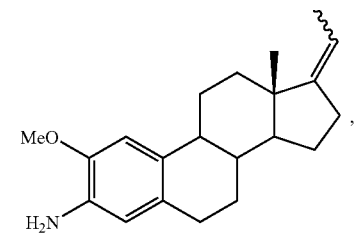
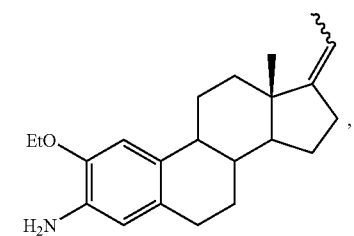
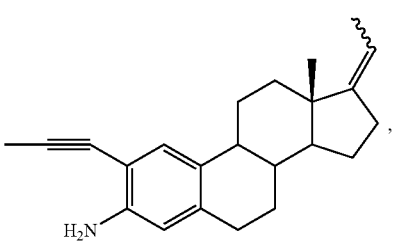
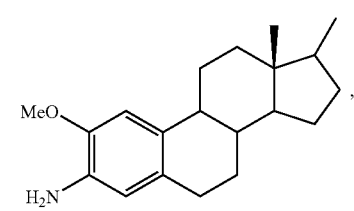
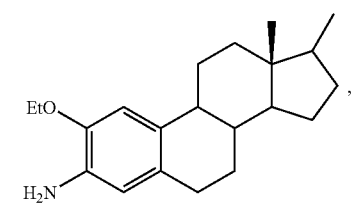
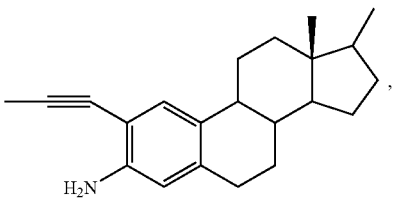
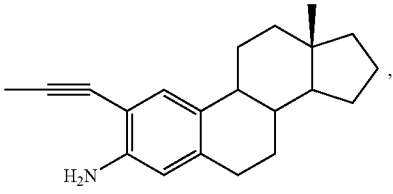
-continued
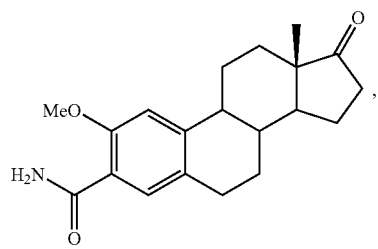
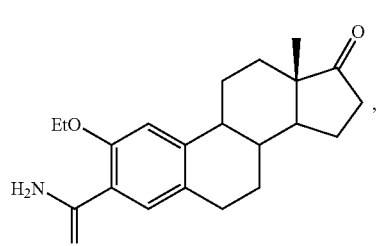
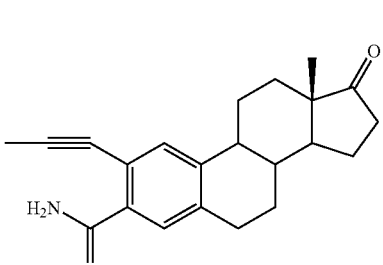
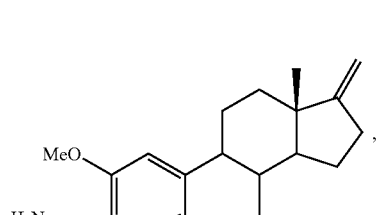
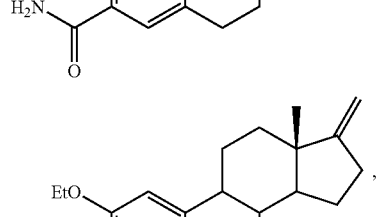
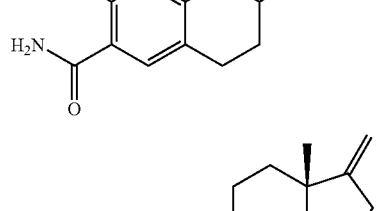
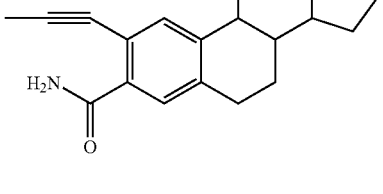

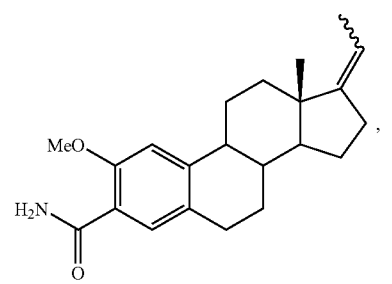
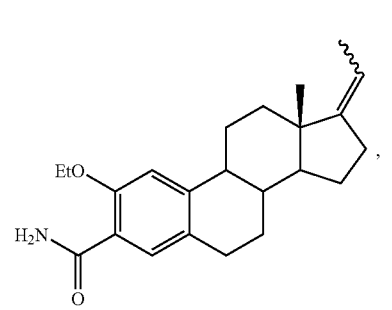
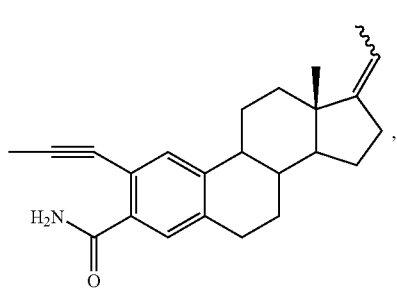
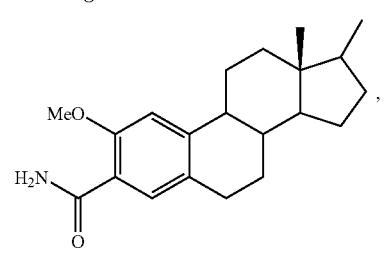
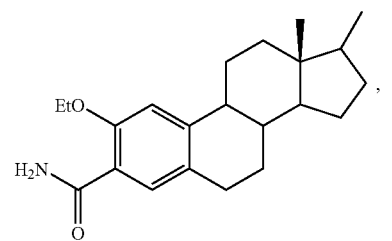
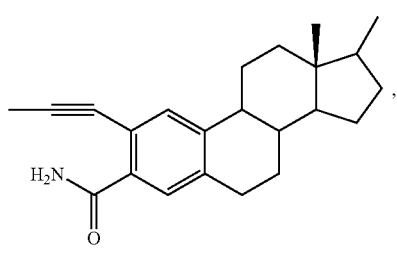
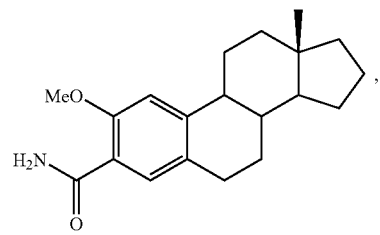
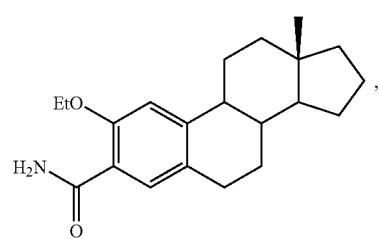
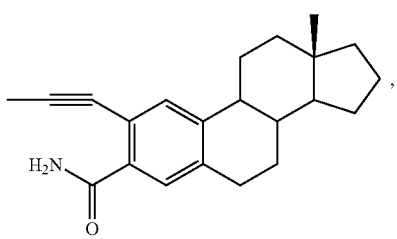
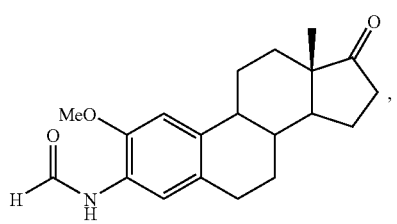
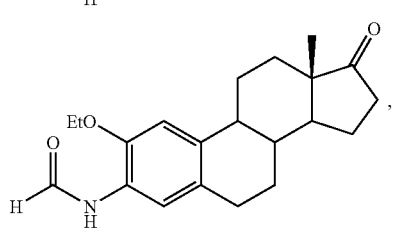
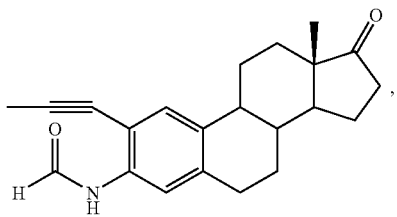
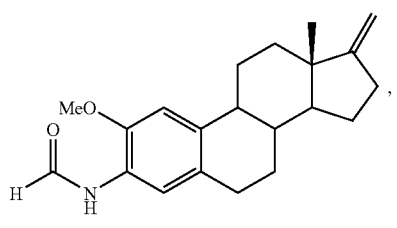

-continued
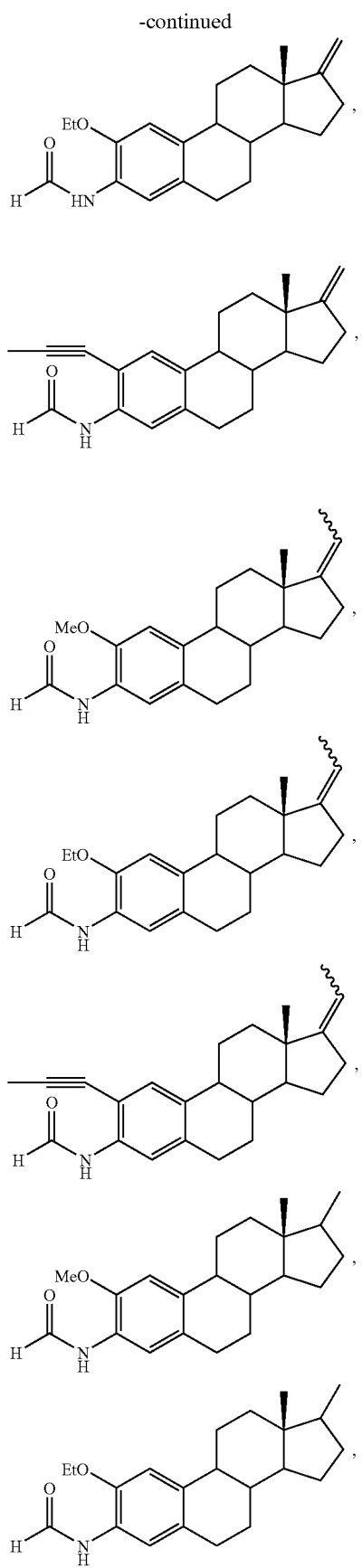
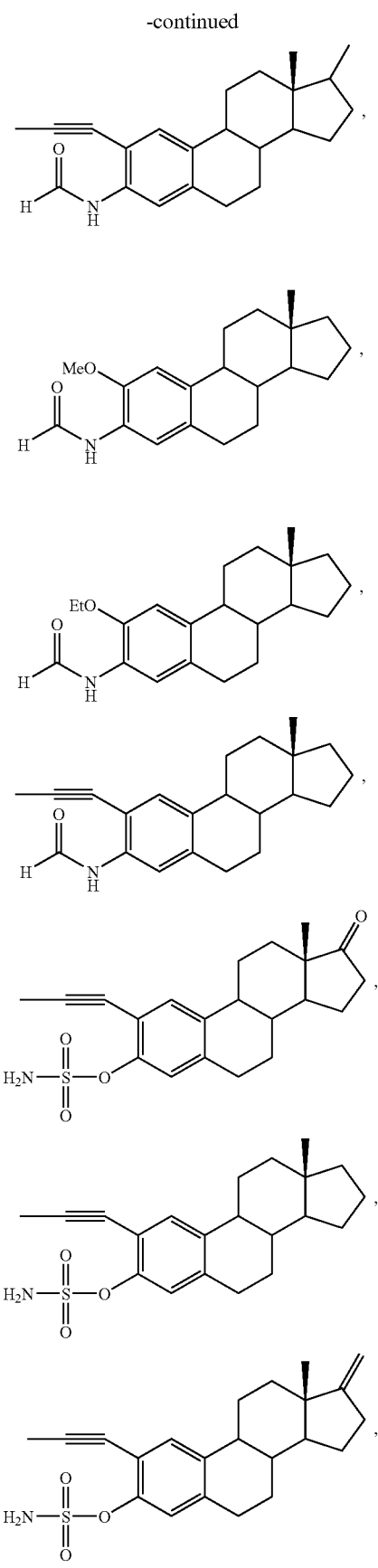

-continued
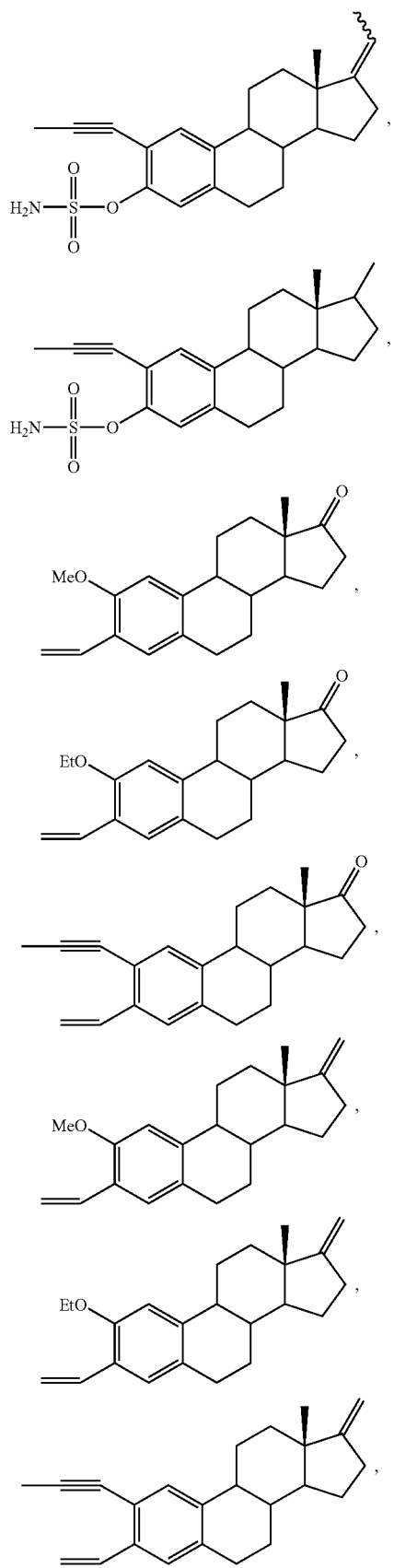
-continued
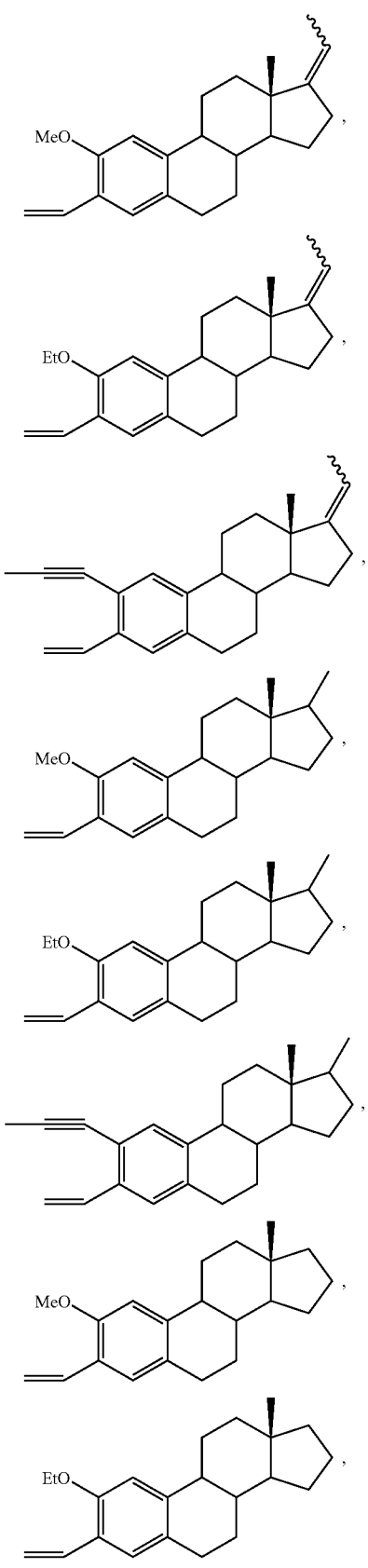

-continued
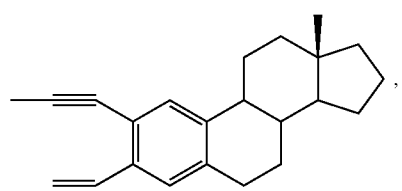,
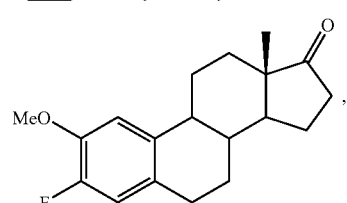,
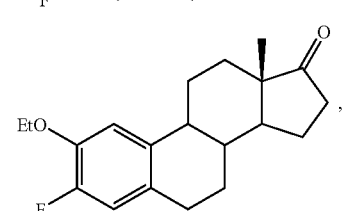,
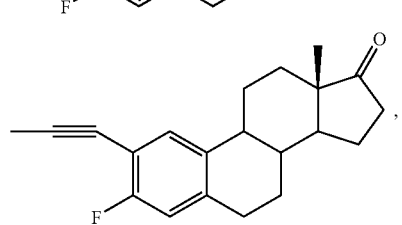,
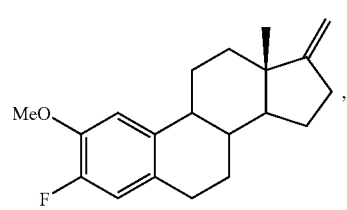,
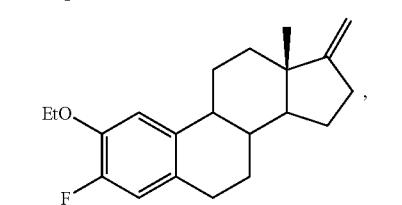,
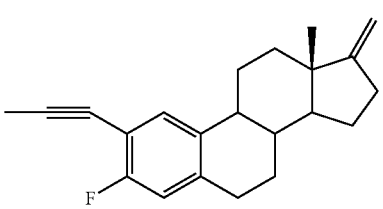,
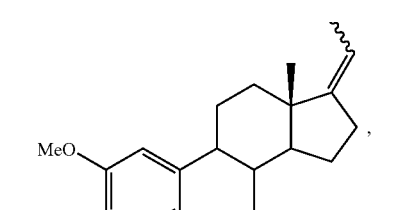,
-continued
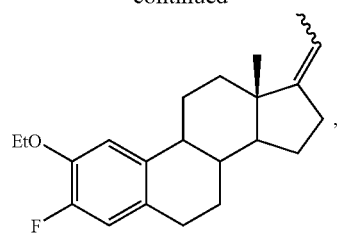,
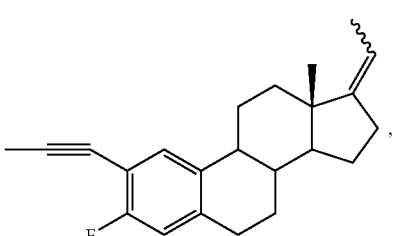,
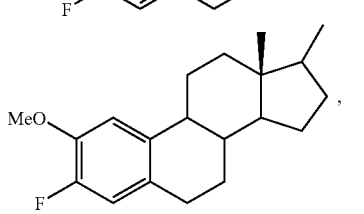,
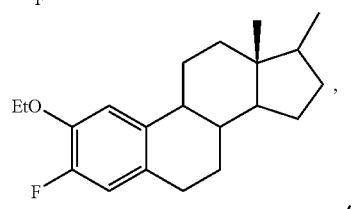,
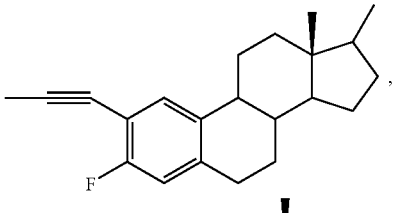,
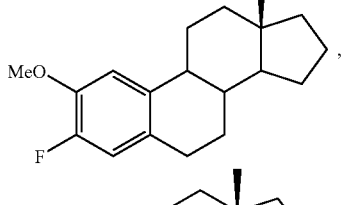, or
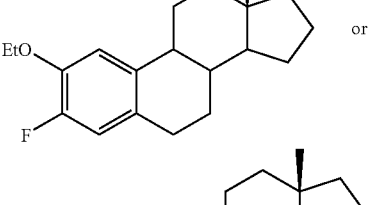
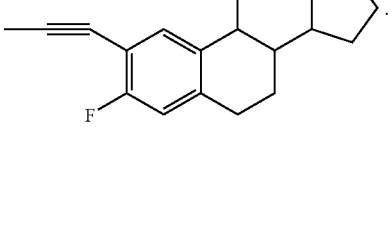.

7. The pharmaceutical composition of claim 6, wherein the compound is:
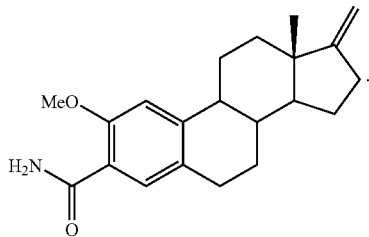
8. The pharmaceutical composition of claim 6, wherein the compound is:
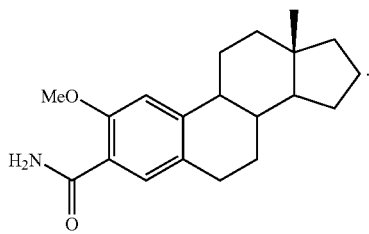
9. A method of treating a solid tumor in a human or an animal comprising administering to the human or animal a compound having the formula
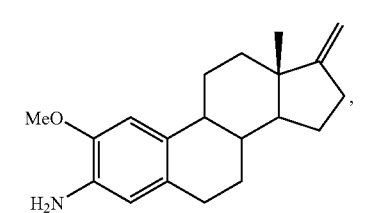
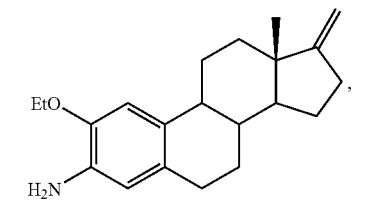
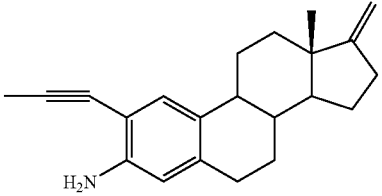
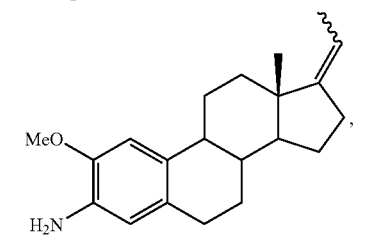
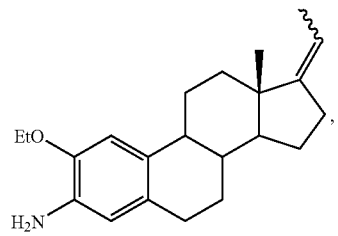
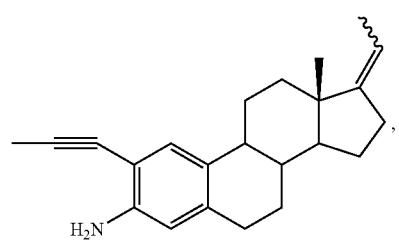
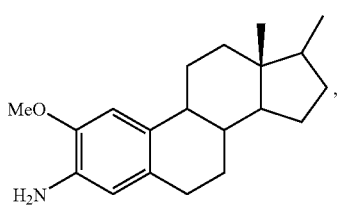
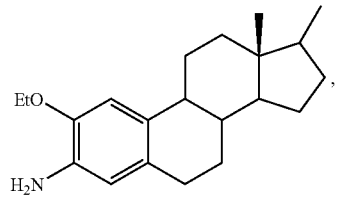
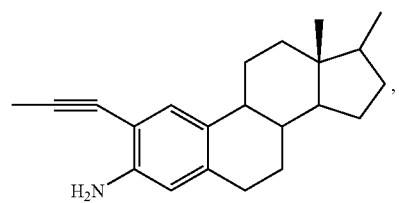
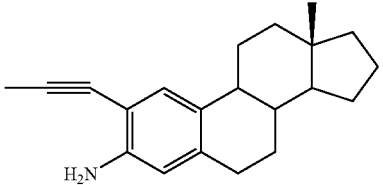
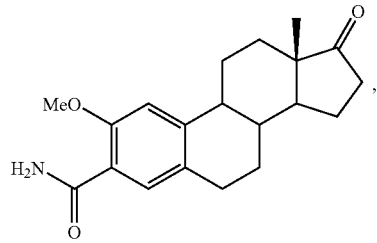

-continued
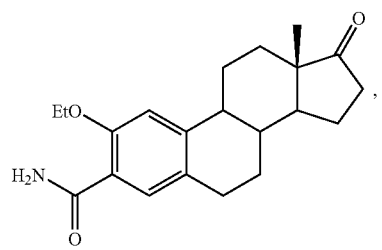
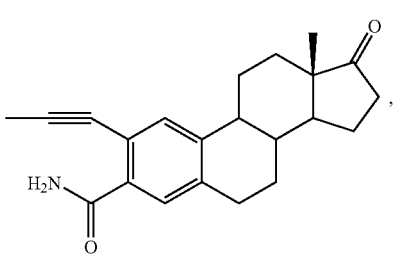
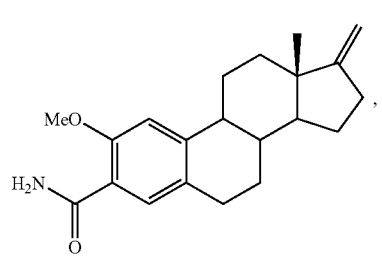
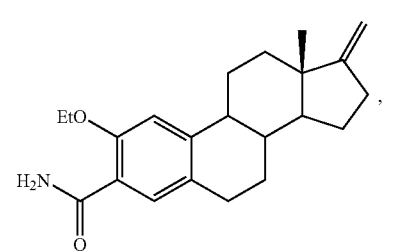
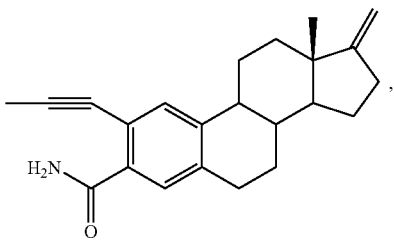
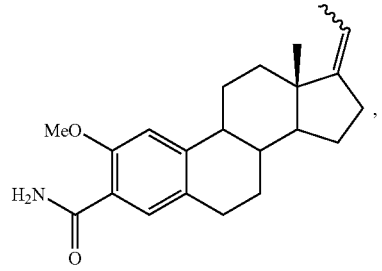
-continued
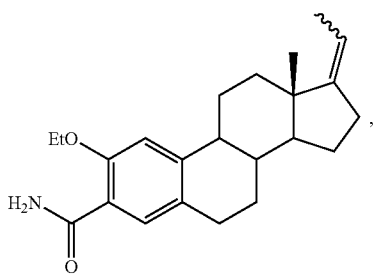
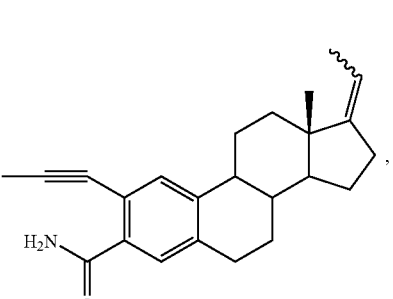
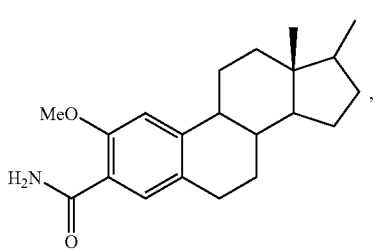
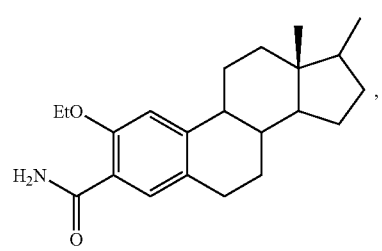
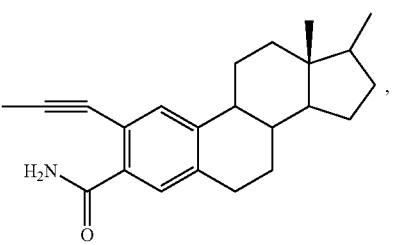
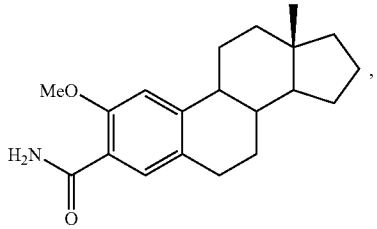

95
-continued
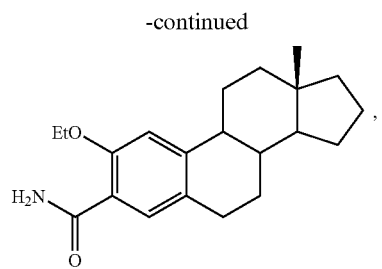
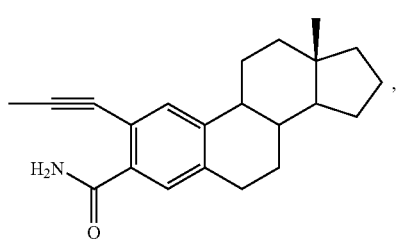
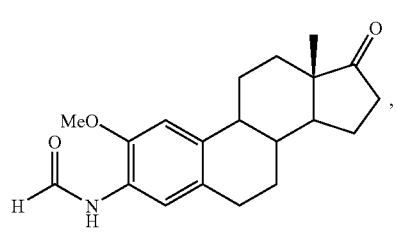
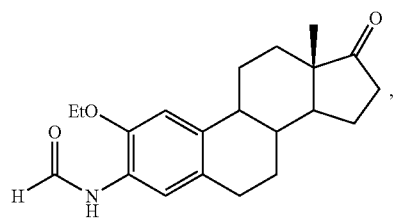
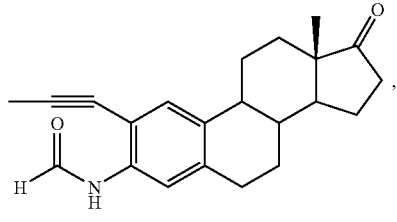
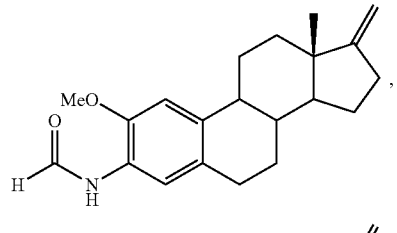
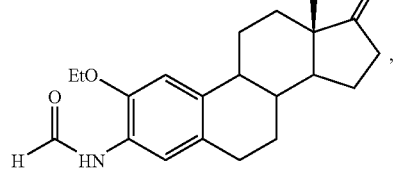
96
-continued
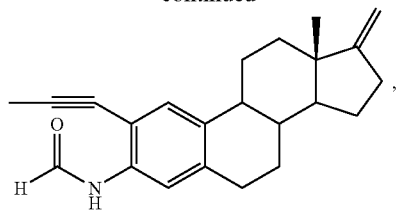
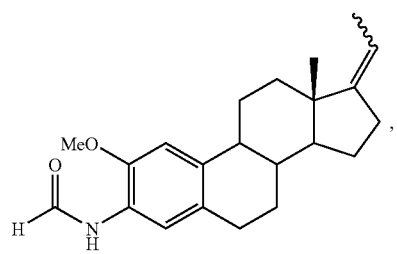
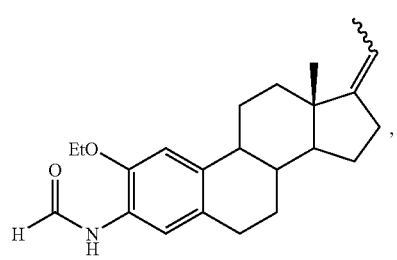
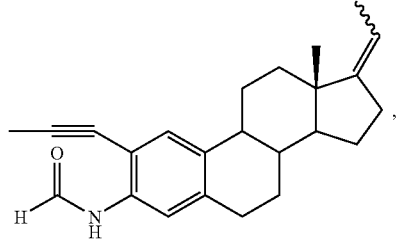
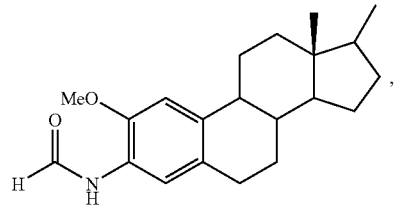
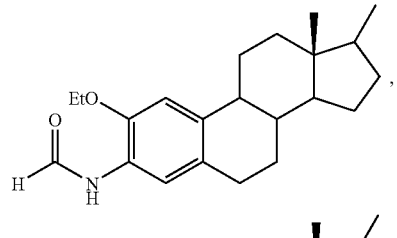
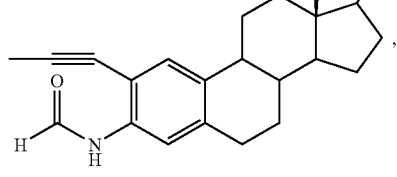

97
-continued
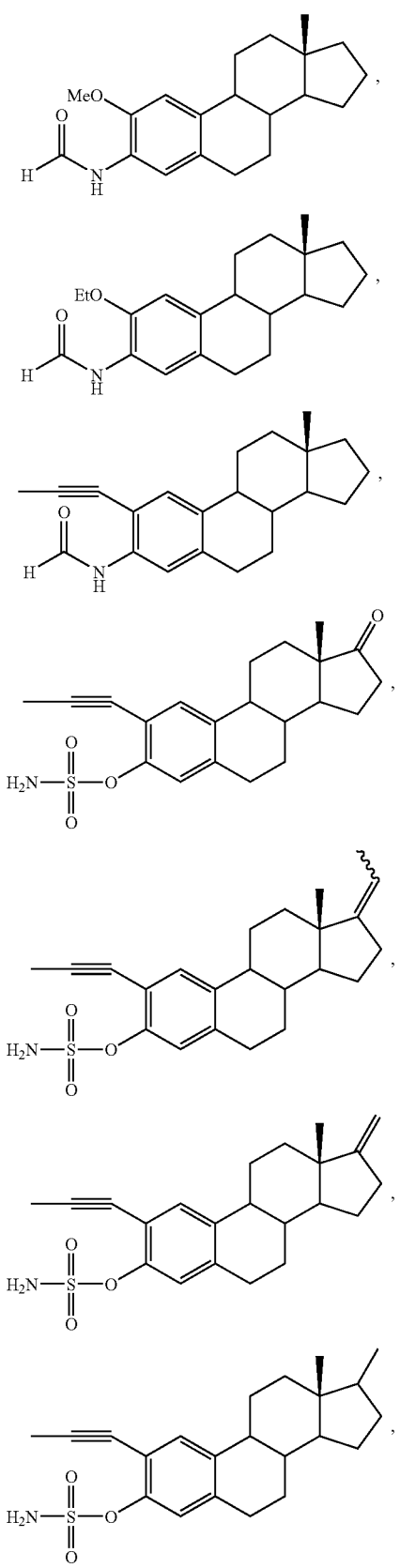
98
-continued
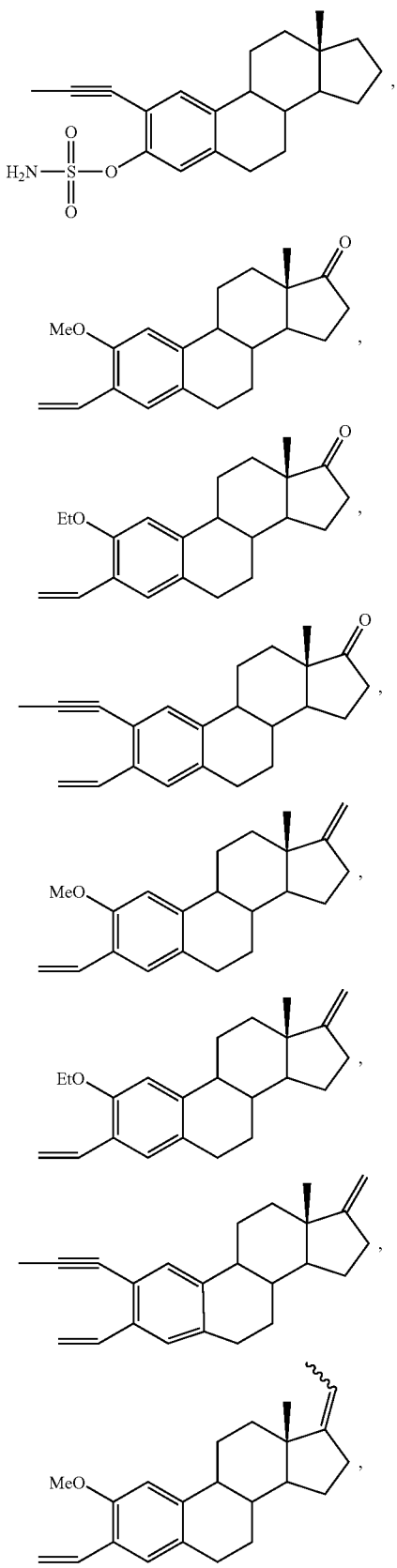

-continued
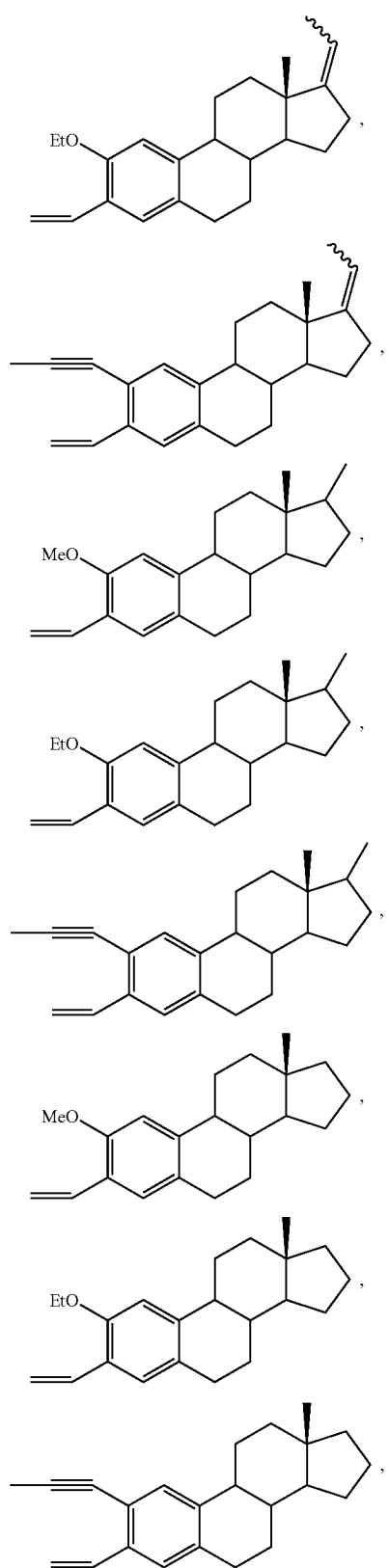
-continued
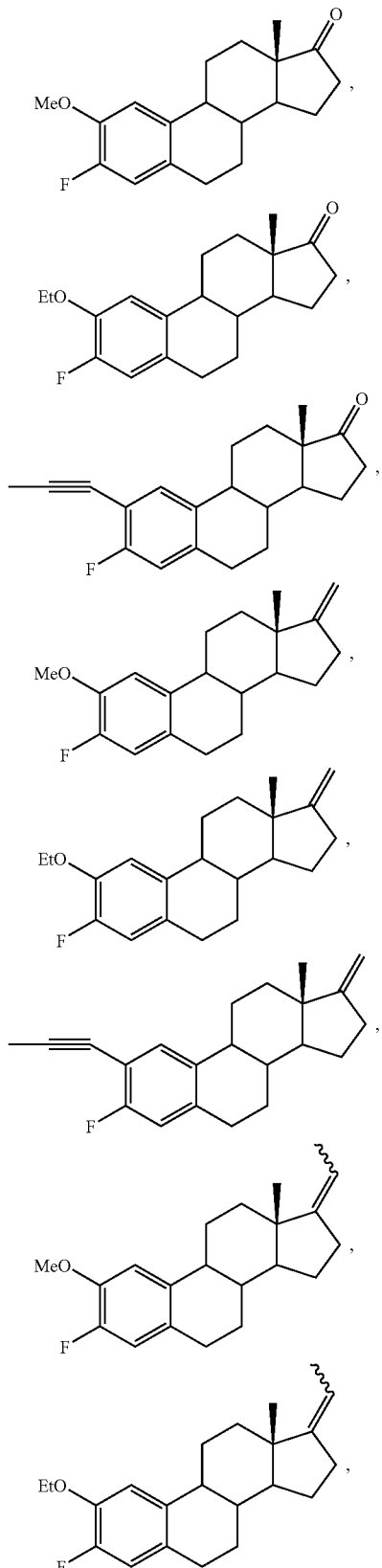

-continued
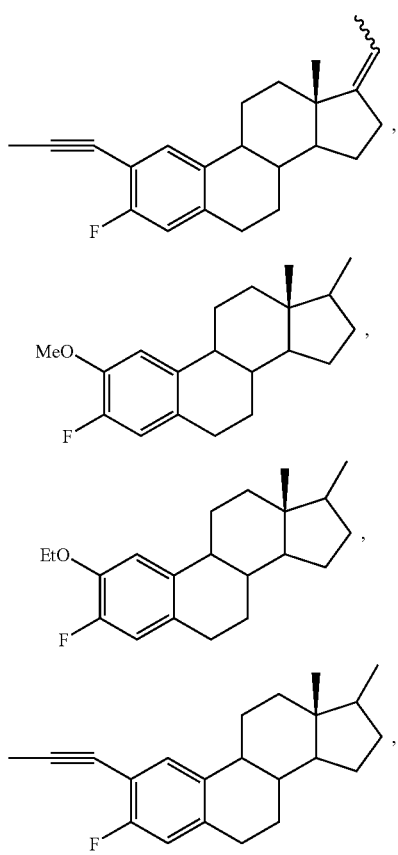
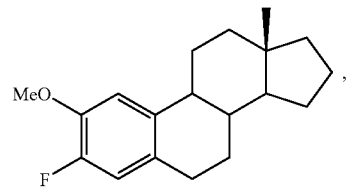
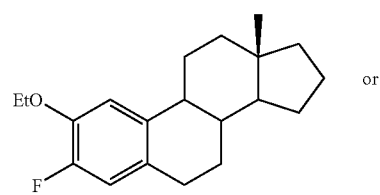
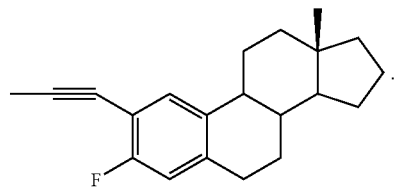
* * * * *